(12) United States Patent
Porter et al.

(10) Patent No.: US 11,738,087 B2
(45) Date of Patent: *Aug. 29, 2023

(54) LYMPH DIRECTING PRODRUGS

(71) Applicant: Monash University, Clayton (AU)

(72) Inventors: Chris Porter, South Melbourne (AU); Jamie Simpson, Boston, MA (US); Natalie Trevaskis, Newington (AU); Tim Quach, Southbank (AU); Sifei Han, Bundoora (AU); Luojuan Hu, Bundoora (AU)

(73) Assignee: Monash University, Clayton (AU)

( * ) Notice: Subject to any disclaimer, the term of this patent is extended or adjusted under 35 U.S.C. 154(b) by 175 days.

This patent is subject to a terminal disclaimer.

(21) Appl. No.: 15/758,633

(22) PCT Filed: Sep. 8, 2016

(86) PCT No.: PCT/AU2016/050845
§ 371 (c)(1),
(2) Date: Mar. 8, 2018

(87) PCT Pub. No.: WO2017/041139
PCT Pub. Date: Mar. 16, 2017

(65) Prior Publication Data
US 2018/0243425 A1  Aug. 30, 2018

(30) Foreign Application Priority Data

Sep. 8, 2015 (AU) .................................. 2015903661

(51) Int. Cl.
*A61K 47/54* (2017.01)
*A61K 31/568* (2006.01)
*A61K 31/27* (2006.01)
*A61K 31/365* (2006.01)
*A61K 31/485* (2006.01)
*A61K 31/222* (2006.01)
*A61K 31/165* (2006.01)
*A61K 31/138* (2006.01)
*A61K 31/167* (2006.01)
*C07C 219/06* (2006.01)
*C07C 235/36* (2006.01)
*C07D 307/88* (2006.01)
*C07C 271/24* (2006.01)
*C07D 489/12* (2006.01)
*C07J 1/00* (2006.01)
*A61K 9/00* (2006.01)
*A61K 45/06* (2006.01)

(52) U.S. Cl.
CPC .......... *A61K 47/542* (2017.08); *A61K 9/0053* (2013.01); *A61K 31/138* (2013.01); *A61K 31/165* (2013.01); *A61K 31/167* (2013.01); *A61K 31/222* (2013.01); *A61K 31/27* (2013.01); *A61K 31/365* (2013.01); *A61K 31/485* (2013.01); *A61K 31/568* (2013.01);

*A61K 45/06* (2013.01); *C07C 219/06* (2013.01); *C07C 235/36* (2013.01); *C07C 271/24* (2013.01); *C07D 307/88* (2013.01); *C07D 489/12* (2013.01); *C07J 1/0025* (2013.01); *C07J 1/0029* (2013.01); *C07C 2602/26* (2017.05)

(58) Field of Classification Search
CPC .................................................. A61K 47/542
See application file for complete search history.

(56) References Cited

U.S. PATENT DOCUMENTS

| | | | |
|---|---|---|---|
| 4,587,262 A | 5/1986 | Arnould et al. | |
| 4,958,046 A | 9/1990 | Rosenberg et al. | |
| 5,962,440 A | 10/1999 | Sulsky | |
| 6,013,665 A | 1/2000 | DeMichele et al. | |
| 6,054,591 A | 4/2000 | Aono et al. | |
| 6,417,191 B1 | 7/2002 | Barry et al. | |
| 6,552,065 B2 | 4/2003 | Remiszewski et al. | |
| 7,390,799 B2 | 6/2008 | Bruncko et al. | |
| 7,557,210 B2 | 7/2009 | Singh et al. | |
| 7,635,690 B2 | 12/2009 | Schinazi et al. | |
| 8,138,347 B2 | 3/2012 | Adams et al. | |
| 8,338,439 B2 | 12/2012 | Singh et al. | |
| 8,455,510 B2 | 6/2013 | Nan et al. | |
| 11,311,512 B2 | 4/2022 | Porter et al. | |
| 2004/0204472 A1 | 10/2004 | Briggs et al. | |
| 2007/0191415 A1 | 8/2007 | Kumar et al. | |
| 2009/0023805 A1 | 1/2009 | Marrast et al. | |
| 2009/0297533 A1 | 12/2009 | Lichter et al. | |
| 2010/0298560 A1 | 11/2010 | Choi et al. | |
| 2011/0213028 A1 | 9/2011 | Milne et al. | |

(Continued)

FOREIGN PATENT DOCUMENTS

JP  2003012691    1/2003
WO  WO-1994009010 A1  4/1994

(Continued)

OTHER PUBLICATIONS

Alouane et al., "Self-Immolative Spacers: Kinetic Aspects, Structure-Property Relationships, and Applications," Angewandte Reviews, vol. 54, 2015 (pp. 7492-7509).

(Continued)

*Primary Examiner* — Alicia L Otton

(74) *Attorney, Agent, or Firm* — WOMBLE BOND DICKINSON (US) LLP; Danielle L. Herritt; Matthew J. Powers

(57) ABSTRACT

The present invention relates to compounds and their uses, in particular, compounds in the form of prodrugs that promote transport of a pharmaceutical agent to the lymphatic system and subsequently enhance release of the parent drug.

26 Claims, 10 Drawing Sheets

(56) References Cited

U.S. PATENT DOCUMENTS

| | | |
|---|---|---|
| 2011/0243884 A1 | 10/2011 | O'Shea |
| 2013/0030007 A1 | 1/2013 | Penninger et al. |
| 2014/0081016 A1 | 3/2014 | Felzmann et al. |
| 2014/0234418 A1 | 8/2014 | Coulter et al. |
| 2014/0328793 A1 | 11/2014 | Gavegnano et al. |
| 2017/0326103 A1 | 11/2017 | Porter et al. |
| 2018/0243425 A1 | 8/2018 | Forter et al. |
| 2018/0258094 A1 | 9/2018 | Long et al. |
| 2018/0318318 A1 | 11/2018 | Wang et al. |
| 2019/0105299 A1 | 4/2019 | Porter et al. |
| 2022/0211664 A1 | 7/2022 | Porter et al. |

FOREIGN PATENT DOCUMENTS

| | | |
|---|---|---|
| WO | WO-97/35843 A1 | 10/1997 |
| WO | WO-2001042246 A2 | 6/2001 |
| WO | WO-2002088112 | 11/2002 |
| WO | WO-2003063794 A2 | 8/2003 |
| WO | WO-2004019973 | 3/2004 |
| WO | WO-2004089925 | 10/2004 |
| WO | WO-2004106328 | 12/2004 |
| WO | WO-2005007623 | 1/2005 |
| WO | WO-2005112919 | 12/2005 |
| WO | WO-2005113554 | 12/2005 |
| WO | WO-2006078846 | 7/2006 |
| WO | WO-2006122806 | 11/2006 |
| WO | WO-2007016176 | 2/2007 |
| WO | WO-2007044729 | 4/2007 |
| WO | WO-2007053452 | 5/2007 |
| WO | WO-2007070514 | 6/2007 |
| WO | WO-2007084786 | 7/2007 |
| WO | WO-2007129161 | 11/2007 |
| WO | WO-2008039218 | 4/2008 |
| WO | WO-2008048611 A1 | 4/2008 |
| WO | WO-2008109943 | 9/2008 |
| WO | WO-2008118802 | 10/2008 |
| WO | WO-2009114512 | 9/2009 |
| WO | WO-2009143295 | 11/2009 |
| WO | WO-2011051967 A2 | 5/2011 |
| WO | WO-2011090760 A1 | 7/2011 |
| WO | WO-2011120044 A1 | 9/2011 |
| WO | WO-2015116904 | 8/2015 |
| WO | WO-2016023082 | 2/2016 |
| WO | WO-2017041139 A1 | 3/2017 |
| WO | WO-2017049245 A2 | 3/2017 |
| WO | WO-2018237282 A1 | 12/2018 |
| WO | WO-2019046478 A1 | 3/2019 |
| WO | WO-2019046491 A1 | 3/2019 |

OTHER PUBLICATIONS

Alouane et al., "Self-Immolative Spacers: Kinetic Aspects, Structure-Property Relationships, and Applications," Supporting Information, Angewandte Reviews, 2015 (10 pages).

Amsberry et al., "Amine Prodrugs Which Utilize Hydroxy Amide Lactonization. II. A Potential Esterase-Sensitive Amide Prodrug," Pharmceutical Research, vol. 8, No. 4, 1991 (pp. 455-461).

Blencowe et al., "Self-immolative linkers in polymeric delivery systems," Polymer Chemistry, vol. 2, No. 4, 2011 (pp. 773-790).

Bourgeois et al., "Application of thermal analysis to the study of lipidic prodrug incorporation into nanocarriers," Journal of Thermal Analysis and Calorimetry, vol. 98, No. 1, 2009 (pp. 65-71).

Charette et al. "Practical and Highly Regio- and Stereoselective Synthesis of 2-Substituted Dihydropyridines and Piperidines: Application to the Synthesis of (−)-Coniine," Journal of the American Chemical Society, vol. 123, No. 47, 2001 (pp. 11829-11830).

Chowdhury et al., "Highly Regio- and Enantioselective Organocatalytic Conjugate Addition of Alkyl Methyl Ketones to a β-Silylmethylene Malonate," Organic Letters, vol. 11, No. 15, 2009 (pp. 3270-3273).

Cyr, P. et al., "Recent progress on nuclear receptor RORγ modulators," Bioorganic & Medicinal Chemistry Letters, vol. 26, No. 18, 2016 (pp. 4387-4393).

Deverre et al., "In-vitro evaluation of filaricidal activity of GABA and 1,3-dipalmitoyl-2-(4-aminobutyryl)glycerol HCl: a diglyceride prodrug," Journal of Pharmacy and Pharmacology, vol. 41, No. 3, 1989 (pp. 191-193).

Dommerholt et al., "Readily Accessible Bicyclononynes for Bioorthogonal Labeling and Three-Dimensional Imaging of Living Cells," Angewandte Chemie International Edition, vol. 49, 2010 (pp. 9422-9425).

Edwards et al., "Animal models for the study of intestinal lymphatic drug transport," Advanced Drug Delivery Reviews, vol. 50, No. 1, 2001 (pp. 45-60).

Garzon-Aburbeh et al., "A lymphotropic prodrug of L-dopa: synthesis, pharmacological properties and pharmacokinetic behavior of 1,3-dihexadecanoyl-2-[(S)-2-amino-3-(3,4-dihydroxyphenyl)propanoyl]propane-1,2,3-triol," Journal of Medicinal Chemistry, vol. 29, No. 5, 1986 (pp. 687-669).

Garzon-Aburbeh et al., "1,3-Dipalmitoylglycerol ester of chlorambucil as a lymphotropic, orally administrable antineoplastic agent," Journal of Medicinal Chemistry, vol. 26, No. 8, 1983 (pp. 1200-1203).

Gossauer et al., "Synthesen von Gallenfarbstoffen, V. Stereospezifische Totalsynthesen diastereomerer Mesobilirhodine und Isomesobilirhodine," European Journal of Organic Chemistry, vol. 1977, No. 4, 1977 (pp. 664-686).

Han et al., "Targeted delivery of a model immunomodulator to the lymphatic system: comparison of alkyl ester versus triglyceride mimetic lipid prodrug strategies," Journal of Controlled Release, vol. 177, 2014 (pp. 1-10).

Han et al., "Lymphatic Transport and Lymphocyte Targeting of a Triglyceride Mimetic Prodrug Is Enhanced in a Large Animal Model: Studies in Greyhound Dogs," Molecular Pharmaceutics, vol. 13, No. 10, 2016 (pp. 3351-3361).

Hu et al., "Glyceride-Mimetic Prodrugs Incorporating Self-Immolative Spacers Promote Lymphatic Transport, Avoid First-Pass Metabolism, and Enhance Oral Bioavailability," Angewandte Chemie International Edition, vol. 55, No. 44, 2016 (pp. 13700-13705); Supplementary Information (pp. 1-43).

Huvelle et al., "Syntheses and kinetic studies of cyclisation-based self-immolative spacers," Organic and Biomolecular Chemistry, vol. 15, 2017 (pp. 3435-3443).

International Search Report and Written Opinion issued by the Australian Patent Office as International Searching Authority for International Patent Application No. PCT/AU2015/050460, dated Oct. 15, 2015 (10 pages).

International Search Report and Written Opinion issued by the Australian Patent Office as International Searching Authority for International Patent Application No. PCT/AU2016/050845, dated Oct. 27, 2016 (12 pages).

International Search Report and Written Opinion issued by the United States Patent and Trademark Office as International Searching Authority for International Patent Application No. PCT/US2018/048642, dated Dec. 11, 2018 (10 pages).

Janossy et al., "Lymphocyte activation: I. Response of T and B lymphocytes to phytomitogens," Clinical & Experimental Immunology vol. 9, No. 4, 1971 (pp. 483-498).

Jew et al., "Asymmetric synthesis of (R)-(+)-etomoxir," Tetrahedron: Asymmetry, vol. 8, No. 8, 1997 (pp. 1187-1192).

Jewett et al., "Rapid Cu-Free Click Chemistry with Readily Synthesized Biarylazacyclooctynones," Journal of the American Chemical Society, vol. 132, No. 11, 2010 (pp. 3688-3690).

Kai et al., "Structure-activity relationship study of flowering-inducer FN against Lemna paucicostata," Tetrahedron, vol. 64, No. 28, 2008 (pp. 6760-6769).

Kihel et al., "Synthesis and Evaluation of the Anti-Inflammatory Effects of Niflumic Acid Lipophilic Prodrugs in Brain Edema," Arzneimittelforschung, vol. 46, No. 11, 1996 (pp. 1040-1044).

Kim et al., "Convenient Synthesis of Electron Deficient Dienes via Pd(0) Catalyzed Coupling," Synlett, vol. 10, 1988 (pp. 1059-1060).

Kratz et al., "Prodrug strategies in anticancer chemotherapy," ChemMedChem, vol. 3, No. 1, 2008 (pp. 20-53).

Lalanne et al., "Metabolism evaluation of biomimetic prodrugs by in vitro models and mass spectrometry," International Journal of Pharmaceutics, vol. 379, No. 2, 2009 (pp. 235-243).

(56) References Cited

OTHER PUBLICATIONS

Lalanne et al., "Synthesis and biological evaluation of two glycerolipidic prodrugs of didanosine for direct lymphatic delivery against HIV," Bioorganic & Medicinal Chemistry Letters, vol. 17, No. 8, 2007 (pp. 2237-2240).
Levine et al., "Trimethyl lock: a trigger for molecular release in chemistry, biology, and pharmacology," Chemical Science, No. 8, 2012 (pp. 2412-2420).
Lienard et al., "Structural basis for the broad-spectrum inhibition of metallo-beta-lactamases by thiols," Organic and Biomolecular Chemistry, vol. 6, No. 13, 2008 (pp. 2282-2294).
Louiseau et al. "Lymphotropic antifilarial agents derived from Closantel and Cholorambucil," International Journal for Parasitology, vol. 27, 1997 (pp. 443-447).
Mergen et al., "Antiepileptic activity of 1,3-dihexadecanoylamino-2-valproyl-propan-2-ol, a prodrug of valproic acid endowed with a tropism for the central nervous system," Journal of Pharmacy and Pharmacology, vol. 43, No. 11, 1991 (pp. 815-816).
Paris et al., "Glycerides as prodrugs. 1. Synthesis and anti-inflammatory activity of 1,3-bis(alkanoyl)-2-(O-acetylsalicyloyl)glycerides (aspirin triglycerides)," Journal of Medicinal Chemistry, vol. 22, No. 6, 1979 (pp. 683-687).
Paris et al., "Glycerides as Prodrugs. 2. 1,3 Dialkanoyl1-2-(2-methyl-4-oxo-1,3-benzodioxan-2-yl) glycerides (Cyclic Aspirin Triglycerides) as Anti-inflammatory Agents," Journal of Medicinal Chemistry, 1980, vol. 23, No. 1, 1980 (pp. 79-82).
Paris et al., "Glycerides as Prodrugs. 3. Synthesis and Anti-inflammatory Activity of [10(p-Chlorobenzoyl)-5-methoxy-2-methylindole-3-acetyl]gycertides (Indomethacin Glycerides)," Journal of Medicinal Chemistry, vol. 23, No. 1, 1980 (pp. 9-13).
Pouton, C.W., "Formulation of poorly water-soluble for oral administration: physicochemical and physiological issues and the lipid formulation classification system," European Journal of Pharmaceutical Sciences, vol. 29, Nos. 3-4, 2006 (pp. 278-287).
Pouton, C. W., "Lipid formulations for oral administration of drugs: non-emulsifying, self-emulsifying and 'self-microemulsifying' drug delivery systems," European Journal of Pharmaceutical Sciences, vol. 11, supp. 2, 2000 (pp. S93-S98).
Scriba et al., "Bioavailability of Phenytoin Following Oral Administration of Phenytoin-lipid Conjugates to Rats," Journal of Pharmacy and Pharmacology, vol. 47, No. 11, 1995 (pp. 945-948).
Scriba et al., "Synthesis and in Vitro Degradation of Testosterone-Lipid Conjugates," Archiv der Pharmazie—Chemistry in Life Science, vol. 328, 1995 (pp. 271-276).
Silverman, R. B., "'Chapter 8—Prodrugs and Drug Delivery Systems" in The Organic Chemistry of Drug Design and Drug Action (Second Edition), 2004 (pp. 497-557, 520-525).
Silverman, R. B., "Chapter 9—Prodrugs and Drug Delivery Systems" in The Organic Chemistry of Drug Design and Drug Action (Third Edition), 2014 (pp. 423-468).
Skanji et al., "A new nanomedicine based on didanosine glycerolipidic prodrug enhances the long term accumulation of a drug in a HIV sanctuary," International Journal of Pharmaceutics, vol. 414, Nos. 1-2, 2011 (pp. 285-297).
Sobczak "Synthesis and characterization of polyester conjugates of ciprofloxacin," European Journal of Medicinal Chemistry vol. 45, No. 9, 2010 (pp. 3844-3849).
Subba Reddy et al., "A Concise and Convergent Total Synthesis of Two Novel Cytotoxic Hydroquinones, Lanneaquinol and (R)-2'-Hydroxylanneaquinol," Helvetica Chimica Acta, vol. 96, No. 10, 2013 (pp. 1983-1990).
Sugihara et al., "Studies on intestinal lymphatic absorption of drugs. I. Lymphatic absorption of alkyl ester derivatives and alpha-monoglyceride derivatives of drugs," Journal of Pharmacobio-Dynamics, vol. 11, No. 5, 1988 (pp. 369-376).
Sugihara et al., "Studies on intestinal lymphatic absorption of drugs. II. Glyceride prodrugs for improving lymphatic absorption of naproxen and nicotinic-acid," Journal of Pharmacobio-Dynamics, vol. 11, No. 8, 1988 (pp. 555-562).

Takada et al., "Conversion of a Novel 5-fluorouracil (5-FU) Derivative to 5-FU in Rats," Research and Communications in Chemical Pathology and Pharmacology, vol. 40, No. 1, 1983 (pp. 99-108).
Takagi et al., "The synthesis of enantiomerically pure novel liquid crystal compounds containing the bis(trifluoromethyl)alkanediol moiety," Tetrahedron: Asymmetry, vol. 15, No. 17, 2004 (pp. 2591-2594).
Tranoy-Opalinsky et al., "Design of Self-Immolative Linkers for Tumour-Activated Prodrug Therapy," Anti-Cancer Agents in Medicinal Chemistry, vol. 8, No. 6, 2008 (pp. 618-637).
Trevaskis et al., "Bile increases intestinal lymphatic drug transport in the fasted rat," Pharmaceutical Research, vol. 22, No. 11, 2005 (pp. 1863-1870).
U.S. Appl. No. 16/209,600, filed Dec. 4, 2018 (143 pages).
Warren et al., "Evaluation of the Structural Determinants of Polymeric Precipitation Inhibitors Using Solvent Shift Methods and Principle Component Analysis," Molecular Pharmaceutics, vol. 10, No. 8, 2013 (pp. 2823-2848).
Wittman et al., "Synthesis and antitumor activity of novel paclitaxel-chlorambucil hybrids," Bioorganic and Medicinal Chemistry Letters, vol. 11, No. 6, 2001 (pp. 811-814).
Wolbers et al., "Viability study of HL60 cells in contact with commonly used microchip materials," Electrophoresis, vol. 27, No. 24, 2006 (pp. 5073-5080).
Young et al., "Total Synthesis of (+)-Nakadomarin A," Journal of the American Chemical Society, vol. 129, No. 5, 2007 (pp. 1465-1469).
Zgair et al., "Oral administration of cannabis with lipids leads to high levels of cannabinoids in the intestinal lymphatic system and prominent immunomodulation," Scientific Reports 7, Article No. 14542, 2017 (pp. 1-12).
Amory et al., "Oral testosterone-triglyceride conjugate in rabbits: single-dose pharmacokinetics and comparison with oral testosterone undecanoate," J. Androl. 2003;24(5):716-20.
Andréen et al., "Sex steroid induced negative mood may be explained by the paradoxical effect mediated by GABAA modulators," Psychoneuroendocrinology. 2009;34(8):1121-32.
Bitran et al., "Anxiolytic effect of progesterone is mediated by the neurosteroid allopregnanolone at brain GABAA receptors," J. Neuroendocrinol. 1995;7(3):171-7.
Braile-Fabris et al., "Controlled clinical trial of IV cyclophosphamide versus IV methylprednisolone in severe neurological manifestations in systemic lupus erythematosus," Ann. Rheum. Dis. 2005;64(4):620-25.
Brand et al., "Collagen-induced arthritis," Nat. Protoc. 2007;2(5):1269-75.
Codelli et al., "Second-Generation Difluorinated Cyclooctynes for Copper-Free Click Chemistry," J. Am. Chem. Soc. 2008; 130(34):11486-11493.
Coutinho and Chapman, "The anti-inflamatory and immunosuppressive effects of glucocorticoids, recent developments and mechanistic insights," Mol. Cell. Endrocrinol. 2011;335(1):2-13.
D'yakova et al., "Lymphotropic prodrugs based on 2',3'-didehydro-3'-deoxythymidine. Synthesis and sensitivity to hydrolysis," Russian Journal of Bioorganic Chemistry. 2011;47(10):1588-1593.
DeWolf and Sykes, "Alloimmune T cells in transplantation ," J. Clin. Invest. 2017;127(7):2473-2481.
Freitag et al., "Gliadin-primed CD4+CD45RBlowCD25– T cells drive gluten-dependent small intestinal damage after adoptive transfer into lymphopenic mice," Gut. 2009;58(12):1597-605.
Frye and Duncan, "Progesterone metabolites, effective at the GABAA receptor complex, attenuate pain sensitivity in rats," Brain Res. 1994:643(1-2):194-203.
Frye and Walf, "Changes in progesterone metabolites in the hippocampus can modulate open field and forced swim test behavior of proestrous rats," Horm. Behav. 2002;41(3):306-15.
Goodin, "Glucocorticoid treatment of multiple sclerosis," Handb. Clin. Neurol. 2014;122:455-64.
Grainge et al., "Case series reporting the effectiveness of mycophenolate mofetil in treatment-resistant asthma," Eur. Respir. J. 2013;42(4):1134-7.

(56) References Cited

OTHER PUBLICATIONS

Griffin et al., "Niemann-Pick type C disease involves disrupted neurosteroidogenesis and responds to allopregnanolone," Nat. Med. 2004;10(7):704-11.
Guo et al., "Rheumatoid arthritis: pathological mechanisms and modern pharmacologic therapies," Bone Res. 2018;6:15.
Gupta et al., "Dexamethasone cyclophosphamide pulse therapy in systemic lupus erythematosus: a case report," J. Dermatolg. Treat. 2009;20(1):55-8.
Irwin and Diaz Brinton, "Allopregnanolone as regenerative therapeutic for Alzheimer's disease: translational development and clinical promise," Prog. Neurobiol. 2014;113:40-55.
Irwin et al., "Frontiers in therapeutic development of allopregnanolone for Alzheimer's disease and other neurological disorders," Front. Cell. Neurosci. 2014;8:203.
Iwaszkiewicz-Grzes et al., "Synthesis and biological activity of mycophenolic acid-amino acid derivatives," Eur. J. Med. Chem. 2013;69:863-71.
Jeong et al., "Dose optimization of tacrolimus for improving survival time of PEGylated islets in a rat-to-mouse xenograft model," Macromolecular Research. 2016;24(12):1047-1054.
Kanes et al., "Brexanolone (SAGE-547 injection) in post-partum depression: a randomised controlled trial," Lancet. 2017;390(10093):480-489.
Kim et al., "The Anti-Inflammatory Effects of Oral-Formulated Tacrolimus in Mice with Experimental Autoimmune Encephalomyelitis," J. Korean Med. Sci. 2017;32(9):1502-1507.
Koboziev et al., "Gut-associated lymphoid tissue, T cell trafficking, and chronic intestinal inflammation," Ann. NY. Acad. Sci. 2010;1207(Suppl 1):E86-E93.
Li et al., "Mycophenolate mofetil or tacrolimus compared with intravenous cyclophosphamide in the induction treatment for active lupus nephritis," Nephrol. Dial. Transplant. 2012;27(4):1467-72.
Ling and Luster, "Allergen-Specific CD4+ T Cells in Human Asthma," Ann. Am. Thorac. Soc. 2016;13(Suppl 1):S25-S30.
Ling et al., C1q restrains autoimmunity and viral infection by regulating CD8+ T cell metabolism; Science. May 4, 2018;360(6388):558-563.
Lonshakov et al., "Synthesis and properties of 3'-azido-3'-deoxythymidine derivatives of glycerolipids," Pharm. Chem. J. 2011;44(10):557-563.
Lui et al., "Effect of mycophenolate mofetil on severity of nephritis and nitric oxide production in lupus-prone MRL/lpr mice," Lupus. 2002;11(7):411-8.
Lv et al., "Mycophenolate Mofetil Modulates Differentiation of Th1/Th2 and the Secretion of Cytokines in an Active Crohn's Disease Mouse Model," Int. J. Mol. Sci. 2015;16(11):26654-66.
Maria and Davidson, "Emerging areas for therapeutic discovery in SLE," Curr. Opin. Immunol. 2018;55:1-8.
Mattarei et al., "Novel lipid-mimetic prodrugs delivering active compounds to adipose tissue," Eur. J. Med. Chem. 2017;135:77-88.
Meliambro et al., "Therapy for Proliferative Lupus Nephritis," Rheum. Dis. Clin. North Am. 2018;44(4):545-560.
Michel et al., "Mycophenolate mofetil in multiple sclerosis: a multicentre retrospective study on 344 patients," J. Neurol. Neurosurg. Psychiatry. 2014;85(3):279-83.
Miller and Karpus, "Experimental autoimmune encephalomyelitis in the mouse," Curr. Protoc. Immunol. 2007;Chapter 15:Unit 15.1.
Minard-Colin et al., "Lymphoma depletion during CD20 immunotherapy in mice is mediated by macrophage FcγRI, FcγRIII, and FcγRIV," Blood. 2008;112(4):1205-1213.
Miyamoto et al., "A novel prodrug strategy for extremely hydrophobic agents: conjugation to symmetrically branched glycerol trimer improves pharmacological and pharmacokinetic properties of fenofibrate," Mol. Pharm. 2013;10(7):2723-9.
Mok, "Mycophenolate mofetil for lupus nephritis: an update," Expert Rev. Clin. Immunol. 2015;11(12):1353-64.
Nakajima, et al., "Effectiveness of tacrolimus in comparison with methotrexate or biologics in propensity score-matched patients with rheumatoid arthritis," Mod. Rheumatol. 2016;26(6):836-843.
Nash et al., "Phase 3 study comparing methotrexate and tacrolimus with methotrexate and cyclosporine for prophylaxis of acute graft-versus-host disease after marrow transplantation from unrelated donors," Blood. 2000;96:2062-2068.
Negi and Das, "CNS: Not an immunoprivilaged site anymore but a virtual secondary lymphoid organ," Int. Rev.Immunol. 2018;37(1):57-68.
Nieschlag et al., "Testosterone replacement therapy: current trends and future directions," Hum. Reprod. Update. 2004;10(5):409-19.
Ning et al., "Visualizing metabolically labeled glycoconjugates of living cells by copper-free and fast huisgen cycloadditions," Angew. Chem. Int. Ed. Engl. 2008; 47(12):2253-5.
Okayama et al., "Mast cells are involved in the pathogenesis of indomethacin-induced rat enteritis," J. Gastroenterol. 2009;44(Suppl 19):35-9.
Osborne et al., "Lower allopregnanolone during pregnancy predicts postpartum depression: An exploratory study," Psychoneuroendocrinology. 2017;79:116-121.
Pallet et al., "Impact of Immunosuppressive Drugs on the Metabolism of T Cells ," Int. Rev. Cell. Mol. Biol. 2018;341:169-200.
PCT International Search Report and Written Opinion from PCT/US2018/066580 dated Apr. 24, 2019.
PCT International Search Report and Written Opinion from PCT/US2018/066585 dated Apr. 30, 2019.
PCT International Search Report and Written Opinion from PCT/US2019/044877 dated Oct. 24, 2019.
PCT International Search Report and Written Opinion from PCT/US2020/020387 dated Jun. 24, 2020.
PCT International Search Report and Written Opinion from PCT/US2020/020398 dated Jul. 20, 2020.
PCT International Search Report and Written Opinion from PCT/US2020/020433 dated Jun. 26, 2020.
Perché et al., "Prenatal testosterone treatment potentiates the aggression-inhibiting effect of the neurosteroid dehydroepiandrosterone in female mice," Agress. Behav. 2001;27(2):130-8.
Pesu et al., "Jak3, severe combined immunodeficiency, and a new class of immunosuppressive drugs," Immunol. Rev. 2005;203:127-42.
Ple et al., "Natural killer cells accumulate in lung-draining lymph nodes and regulate airway eosinophilia in a murine model of asthma," Scand. J. Immunol. 2010;72(2):118-27.
Pond and Tozer, "First-pass elimination. Basic concepts and clinical consequences," Clin. Pharmacokinet. 1984;9(1):1-25.
Powell et al., "The immunomodulatory drugs cyclosporin A, mycophenolate mofetil, and sirolimus (rapamycin) inhibit allergen-induced proliferation and IL-5 production by PBMCs from atopic asthmatic patients," 2001;108(6):915-7.
Pubmed Compound Summary for CID 132121512, '1-O-[3R,5S,8S,9S,10S,13S,14S,17S)-17-Acetyl-10,13-dimethyl-11-oxo-1,2,3,4,5,6,7,8,9,12,14,15,16,17-tetradecahydrocyclopenta[a]phenanthren-3-yl] 3-O-[1,3-di(hexadecanoyloxy)propan-2-yl]propanedioate', U.S. National Library of Medicine, Jan. 29, 2018 (https://pubchem.ncbi.nlm.nih.gov/compound/132131512).
Renna et al., "Optimization of the treatment with immunosuppressants and biologics in inflammatory bowel disease," World J. Gastroenterol. 2014;20(29):9675-9690.
Rodriguez-Lago et al., "Previous exposure to biologics and C-reactive protein are associated with the response to tacrolimus in inflammatory bowel disease," Rev. Esp. Enferm. Dig. 2016;108(9):550-7.
Rogawski et al., "Neuroactive steroids for the treatment of status epilepticus," Epilepsia. 2013;54(Suppl 6):93-8.
Rupprecht, "Neuroactive steroids: mechanisms of action and neuropsychopharmacological properties," Psychoneuroendocrinology. 2003;20(2):139-68.
Sagiv-Barfi et al., "Ibrutinib enhances the antitumor immune response induced by intratumoral injection of a TLR9 ligand in mouse lymphoma," Blood. 2015;125(13):2079-86.
Schüle et al., "The role of allopregnanolone in depression and anxiety," Prog. Neurobiol. 2014;113:79-87.

(56) References Cited

OTHER PUBLICATIONS

Shastina et al., "Synthesis, properties, and Anti-HIV activity of new lipophilic 3'-azido-3'-deoxythymidine conjugates containing functional phosphoric linkages," Russian Journal of Bioorganic Chemistry. 2013;39:161-169.
Siebert et al., "New Analogues of Mycophenolic Acid," Mini Rev. Med. Chem. 2017;17(9):734-745.
Smith and Cooper, "Mycophenolate mofetil therapy in the management of inflammatory bowel disease—a retrospective case series and review," J. Crohns Colitis. 2014;8(8):890-7.
Smith et al., "Modular assembly of macrocyclic organo-peptide hybrids using synthetic and genetically encoded precursors," Angew. Chem. Int. Ed. Engl. 2011;50(22):5075-80.
Stadnyk et al., "Neutrophil migration into indomethacin induced rat small intestinal injury is CD11a/CD18 and CD11b/CD18 co-dependent," Gut. 2002;50(5):629-635.
Stump et al., "Lymphatic Changes in Respiratory Diseases: More than Just Remodeling of the Lung?" Am. J. Respir. Cell Mol. Biol. 2017;57(3):272-279.
Tan and Lawrence, "Use of mycophenolate mofetil in inflammatory bowel disease," World J. Gastroenterol. 2009;15(13):1594-1599.
Tanaka et al., "Structure of FK506, a novel immunosuppressant isolated from Streptomyces," J. Am. Chem. Soc. 1987;109(16):5031-5033.
Taniguchi et al., "A Case of Severe Bronchial Asthma Controlled with Tacrolimus," J. Allergy (Cairo). 2011;201:479129.
Taylor and Ryan, "Understanding mechanisms of hypertension in systemic lupus erythematosus," Ther. Adv. Cardiovasc. Dis. 2017;11(1):20-32.
Tohda et al., "Establishment of a novel B-cell lymphoma cell line with suppressed growth by gamma-secretase inhibitors," Leuk. Res. 2006;30(11):1385-90.
Trevaskis et al., "From sewer to saviour—targeting the lymphatic system to promote drug exposure and activity," Nature Review Drug Discovery. 2015;14:781-803.
Van Bruggen et al., "Attenuation of murine lupus nephritis by mycophenolate mofetil," J. Am. Soc. Nephrol. 1998;9(8):1407-15.
Van Dieren et al., "Local application of tacrolimus in distal colitis: feasible and safe," Inflamm. Bowel Dis. 2009;15(2):193-8.
Wagner et al., "Selective epimerization and skeletal resection in the ascomycin framework: A study of the biological consequences of lactam rotamer selection," Tetrahedron. 1996;52(29):9643-9654.
Weyand and Goronzy, "Immunometabolism in early and late stages of rheumatoid arthritis," Nat. Rev. Rheumatol. 2017;13(5):291-301.
Wiebe and Kavaliers, "Analgesic effects of the putative FSH-suppressing gonadal steroid, 3 alpha-hydroxy-4-pregnen-20-one: possible modes of action," Brain Res. 1988;461(1):150-7.
Wirtz et al., "Chemically induced mouse models of acute and chronic intestinal inflammation," Nat. Protoc. 2017;12(7):1295-1309.
Hsieh, P.-S. et al., "Selective COX2 inhibition improves whole body and muscular insulin resistance in fructose-fed rats", European Journal of Clinical Investigation, vol. 38(11):812-819 (2008).
Nieschlag et al., Testosterone replacement therapy: current trends and future directions, Human Reproduction Update, European Society of Human Reproductionand Embryology, Jan. 11, 2004.
Cammack et al., "substituent." Oxford Dictionary Biochemistry and Molecular Biology Revised Edition (2000). Oxford University Press.
Daintith, "substituent." Oxford Dictionary of Chemistry 6th Edition (2008). Oxford University Press.
IUPAC, Commission on Nomenclature of Organic Chemistry. A Guide to IUPAC Nomenclature of Organic Compounds (Recommendations 1993), 1993, Blackwell Scientific publications, Copyright 1993 IUPAC; Downloaded May 6, 2020 fromhttps://www.acdlabs.com/iupac/nomenclature/93/r93_125.htm.
IUPAC, Compendium of Chemical Terminology, 2nd ed. (the "Gold Book"). Compiled by A. D. McNaught and A. Wilkinson. Blackwell Scientific Publications, Oxford (1997). Online version (2019) created by S. J. Chalk. ISBN 0-9678550-9-8.https://doi.org/10.1351/goldbook; Downloaded May 5, 2020.
Wikipedia contributors. (Feb. 11, 2015). Substitution reaction. In Wikipedia, The Free Encyclopedia. Archived May 9, 2015, 8:42:39, at https://web.archive.org/web/20150509084239/https://en.wikipedia.org/wiki/- Substitution_reaction.

LYMPH DIRECTING PRODRUGS

CROSS-REFERENCE TO RELATED APPLICATIONS

This application claims the benefit of and priority under 35 U.S.C. § 371 to Patent Cooperation Treaty application PCT/AU2016/050845, filed Sep. 8, 2016, which claims the benefit of Australian Patent Application No. 2015903661, filed Sep. 8, 2015, the entire contents of both disclosures, which are incorporated herein by reference.

FIELD OF THE INVENTION

The present invention relates to compounds in the form of prodrugs, in particular, compounds that promote transport of a pharmaceutical agent to the lymphatic system and subsequently enhance release of the parent drug.

BACKGROUND OF THE INVENTION

The lymphatic system consists of a specialised network of vessels, nodes and lymphoid tissues that are distributed throughout the body in close proximity to the vascular system. The lymphatic system plays a number of key roles in immune response, fluid balance, nutrient absorption, lipid homeostasis, and tumour metastasis. Due to the unique anatomical and physiological characteristics of the lymphatic system, targeted drug delivery to and through the lymphatic system has been suggested as a means to improve both pharmacokinetic and pharmacodynamic profiles. Lymphatic drug transport has the potential to enhance oral bioavailability through avoidance of first pass metabolism, to alter systemic drug disposition, and to enhance efficacy against lymph or lymphocyte mediated pathologies such as lymphoma, leukemia, lymphatic tumour metastasis, autoimmune disease, lymph resident infections and transplant rejection.

In order for drugs to access the intestinal lymph, they must first associate with intestinal lymph lipoproteins that are assembled in intestinal absorptive cells (enterocytes) in response to lipid absorption. Association with these lipoproteins subsequently promotes drug transport into the lymph since their size precludes ready diffusion across the vascular endothelium lining the blood capillaries that drain the small intestine. Instead, these large colloidal structures enter the lymphatic capillaries since the lymphatic endothelium is considerably more permeable than that of the vascular endothelium. Historically, drugs with high lymphatic transport have been highly lipophilic in order to promote physical association with lipoproteins (usually, but not exclusively, log D>5 and solubility in long chain triglyceride of >50 mg/g). Therefore, highly lipophilic analogues of drugs have been envisaged as one way to promote lymphatic drug transport. However, chemical modification of a parent drug can result in a reduction in potency and in many cases, significant increases in lipophilicity have been correlated with increases in toxicity.

Compounds in the form of lipophilic prodrugs provide a means to temporarily increase lipophilicity and lipoprotein affinity of a pharmaceutical compound, thereby increasing lymphatic targeting. Having been transported via the lymphatic system, the prodrug ultimately reverts to the parent drug in order to be active at its target site.

There have been several studies to explore the potential for simple aliphatic esters of drugs to be used as lymph directing prodrugs. Testosterone undecanoate provides one example of a marketed compound for which this approach has been taken. After oral administration, testosterone is almost entirely metabolised on its first pass through the liver, and consequently, it has minimal bioavailability. The undecanoate ester of testosterone redirects a small proportion of the absorbed dose into the lymphatic system, thereby avoiding hepatic first pass metabolism and increasing the oral bioavailability of testosterone. However, this process is still very inefficient, and the bioavailability of testosterone after oral administration of the undecanoate ester is thought to be <5%.

Another mechanism of promoting lymphatic drug transport is to employ prodrugs that incorporate into endogenous pathways associated with the absorption, transport and disposition of dietary lipids. One example of a dietary lipid utilised as a prodrug is triglyceride. Examples of drug-lipid conjugates have been documented in a number of previous publications where the parent drug contains an available carboxylic acid group and has been directly conjugated to a glyceride backbone (Paris, G. Y. et al., J. Med. Chem. 1979, 22, (6), 683-687; Garzon Aburbeh, A. et al., J. Med. Chem. 1983, 26, (8), 1200-1203; Deverre, J. R.; et al., J. Pharm. Pharmacol. 1989, 41, (3), 191-193; Mergen, F. et al., J. Pharm. Pharmacol. 1991, 43, (11), 815-816; Garzon Aburbeh, A. et al., J. Med. Chem. 1986, 29, (5), 687-69; and Han, S. et al. J. Control. Release 2014, 177, 1-10).

In other examples, a short linker has been used to facilitate drug-triglyceride conjugation where the drug does not contain an available carboxylic acid (Scriba, G. K. E., Arch. Pharm. (Weinheim). 1995, 328, (3), 271-276; and Scriba, G. K. E. et al., J. Pharm. Pharmacol. 1995, 47, (11), 945-948). These drug-lipid conjugates employ succinic acid to facilitate conjugation to an available hydroxyl functionality. However, the literature teaches that this structure is not at all useful, for example, Scriba examined the in vitro hydrolysis of a testosterone-succinic acid-glyceride lipid conjugate and concluded that "testosterone is released only very slowly from the prodrugs by chemical, plasma esterase-catalysed and lipase-mediated hydrolysis in the present study . . . . Thus, testosterone conjugates appear to be poor prodrugs for the delivery of the steroid."

Others have employed an ether linkage to the glyceride, and an ester linkage to the drug (Sugihara, J. et al., J. Pharmacobiodyn. 1988, 11, (5), 369-376; and Sugihara, J. et al., J. Pharmacobiodyn. 1988, 11, (8), 555-562). The authors of these articles state explicitly that the ether bond between glycerol and an n-alkyl chain, and the ester bond between an n-alkyl chain and a drug seem to be necessary for chemical modification of drugs. However, the present inventors have found that an ether linkage is, in fact, counterproductive and does not allow significant lymphatic transport.

Accordingly, there exists a need to develop novel lipid-pharmaceutical agent conjugates that facilitate stable transport of the pharmaceutical agent to the intestinal lymph and that readily revert to the parent agent in order to be active.

SUMMARY OF THE INVENTION

It has now been found that the use of a self-immolative group and certain linkers to join the pharmaceutical agent to the triglyceride unit provide optimal pharmacokinetic profiles for the resultant lipid-pharmaceutical agent conjugate.

Accordingly, in one aspect the present invention provides a compound of the formula (I):

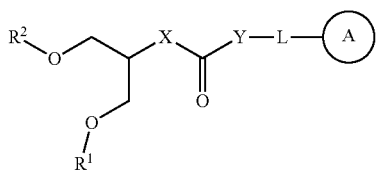

(I)

wherein
$R^1$ and $R^2$ independently represent H, or a residue of a $C_2$-$C_{28}$ fatty acid;
—X— is selected from —O—, —NH— and —S—;

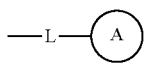

represents a residue of a pharmaceutical agent;
-L- is —OC(O)— or —X'—;
—Y— represents an optionally substituted —$C_1$-$C_{20}$alkylC(O)OCH$_2$—, —$C_2$-$C_{20}$alkenylC(O)OCH$_2$— or —$C_2$-$C_{20}$alkynylC(O)OCH$_2$— group when -L- is —OC(O)—; wherein one or more of the carbon atoms in the alkyl, alkenyl or alkynyl group may be replaced with NH, S, O, a $C_5$-$C_8$ aromatic or aliphatic cyclic group or a $C_5$-$C_8$ aromatic or aliphatic heterocyclic group, provided that the alkyl, alkenyl or alkynyl group does not exceed a length equivalent to a linear $C_{20}$alkyl group; or
—Y— represents an optionally substituted —$C_1$-$C_2$alkylC(O)$R^3$— group or a $C_2$alkenylC(O)$R^3$— or —$C_2$alkynylC(O)$R^3$— group when -L- is —X'—;
$R^3$ is a self-immolative group;
X' is O, S, N($R^4$) or N(H)S(O)$_2$;
$R^4$ is H or $C_1$-$C_4$alkyl; or
pharmaceutically acceptable salts thereof.

In a further aspect the present invention provides a compound of formula (I) represented by the formula (V):

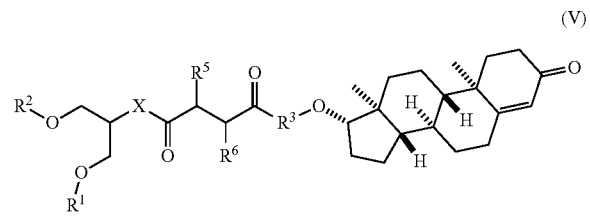

(V)

wherein $R^1$, $R^2$ and —X— are as defined for formula (I);
$R^5$ and $R^6$ are individually selected from hydrogen and $C_1$-$C_4$alkyl; and
$R^3$ is a self-immolative group; or
pharmaceutically acceptable salts thereof.

In another aspect, the present invention provides a method of treating or preventing a disease or disorder in which increased testosterone levels are beneficial, comprising administering to the subject in need thereof a therapeutically effective amount of a compound of the formula (V).

In a further aspect, the present invention provides the use of a compound of the formula (V) in the manufacture of a medicament for the treatment or prevention of a disease or disorder in which increased testosterone levels are beneficial.

In another aspect, the present invention provides a compound of the formula (V) for use in the treatment or prevention of a disease or disorder in which increased testosterone levels are beneficial.

In another aspect, the present invention provides a method of promoting lymphatic transport and systemic release of a pharmaceutical agent comprising conjugating to the pharmaceutical agent a prodrug residue of the formula (VI):

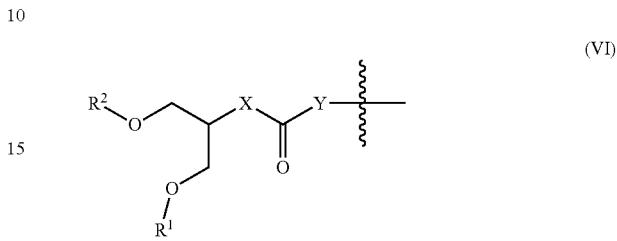

(VI)

wherein
$R^1$ and $R^2$ independently represent H or a residue of a $C_2$-$C_{28}$ fatty acid;
—X— is selected from —O—, —NH— and —S—;
—Y— represents an optionally substituted —$C_1$-$C_2$alkylC(O)$R^3$— group or a —$C_2$alkenylC(O)$R^3$— or —$C_2$alkynylC(O)$R^3$— group when -L- is —X'—;
$R^3$ is a self-immolative group; and
〰 denotes the point where the linker is conjugated to the pharmaceutically active agent; or
pharmaceutically acceptable salts thereof.

These and other aspects of the present invention will become more apparent to the skilled addressee upon reading the following detailed description in connection with the accompanying examples and claims.

DETAILED DESCRIPTION OF THE INVENTION

Figure 1:
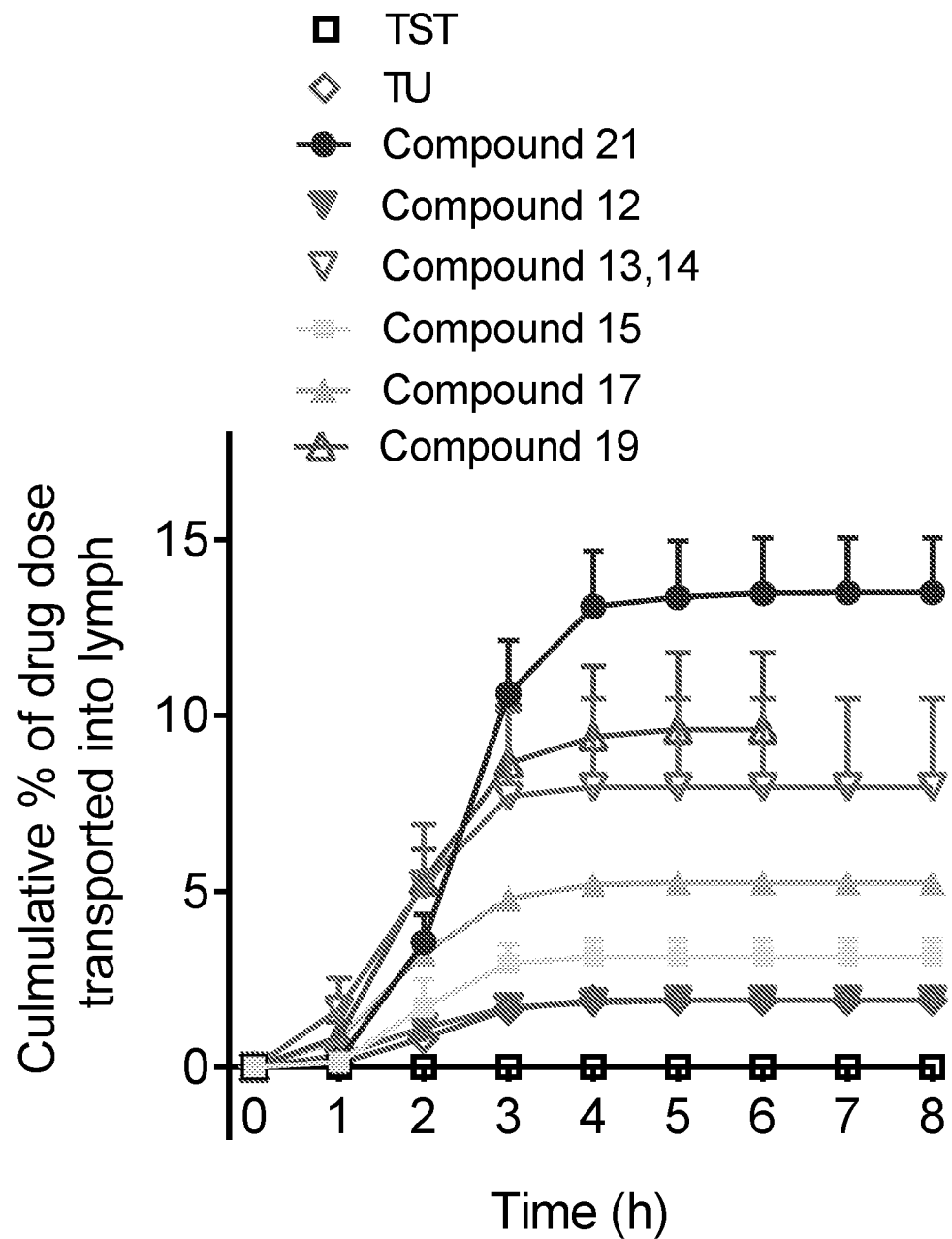
FIG. 1: Graphical representation of the cumulative lymphatic transport of total testosterone related derivatives (% of administered dose) versus time in anaesthetised, mesenteric lymph duct cannulated female SD rats following intraduodenal infusion of testosterone, testosterone undecanoate (TU), Compound 21, Compound 12, Compounds 13/14, Compound 15, Compound 17 and Compound 19.

When prodrug strategies are employed in the field of drug development to improve pharmacokinetic properties, prodrugs are usually expected to revert to the parent compound via non-specific degradation or enzyme-mediated biotransformation, prior to exhibiting biological activity. The current invention discloses modified glyceride based compounds that are able to promote lymphatic transport of the pharmaceutical agent and improve reversion of the compound to the active pharmaceutical agent.

Dietary lipids, such as triglycerides use a unique metabolic pathway to gain access to the lymph (and ultimately the systemic circulation) that is entirely distinct from that of other nutrients such as proteins and carbohydrates. After ingestion, dietary triglycerides are hydrolysed by luminal lipases to release one monoglyceride and two fatty acids for each molecule of triglyceride. The monoglyceride and two fatty acids are subsequently absorbed into enterocytes, where they are re-esterified to triglycerides.

Resynthesised triglycerides are assembled into intestinal lipoproteins (primarily chylomicrons) and the chylomicrons so formed are exocytosed from enterocytes and subsequently gain preferential access to the intestinal lymphatics. Within the lymphatics, lipids in the form of chylomicrons, drain through a series of capillaries, nodes and ducts, finally emptying into the systemic circulation at the junction of the left subclavian vein and internal jugular vein. Following entry into blood circulation, triglycerides in chylomicrons are preferentially and efficiently taken up by tissues with high expression of lipoprotein lipases such as adipose tissue, the liver and potentially certain types of tumour tissues.

Lipid mimetic compounds are expected to behave similarly to natural triglycerides and to be transported to and through the lymphatic system before reaching the systemic circulation. In this way, the pharmacokinetic and pharmacodynamic profiles of the parent pharmaceutical agent may be manipulated to enhance access to the lymph and lymphoid tissues, thereby promoting oral bioavailability via avoidance of first pass metabolism (and potentially intestinal efflux). Lipid mimetic compounds may also promote drug-targeting to sites within the lymph, lymph nodes and lymphoid tissues, and to sites of high lipid utilisation and lipoprotein lipase expression such as adipose tissue, liver and some tumours.

Lipidated prodrugs that readily convert to parent drug after transport via the systemic circulation reduce free drug concentrations in the gastrointestinal (GI) tract, which may provide benefits in reducing gastrointestinal irritation, in taste masking, in promoting drug solubilisation in intestinal bile salt micelles (due to similarities to endogenous monoglycerides) and in enhancing passive membrane permeability (by increasing lipophilicity). Lipidated prodrugs also promote solubility in lipid vehicles comprising either lipids alone or mixtures of lipids with surfactants and/or cosolvents, and in doing so allow larger doses to be administered with the drug in solution than might be possible for parent drug.

The present inventors have surprisingly found that the portion of the drug-glyceride conjugate linking the pharmaceutical agent to the glyceride unit can be modified to improve stability of the drug-glyceride conjugate in the GI tract, promote transport to the intestinal lymph and ultimately, promote release of the pharmaceutical agent from the pharmaceutical agent-glyceride prodrug. Accordingly, by altering the "linker" joining the pharmaceutical agent to the glyceride unit, optimal pharmacokinetic profiles can be achieved for the resultant compound.

The present inventors have found that incorporation of a self-immolative group in the linker between the pharmaceutical agent and the glyceride unit, even when the linker is a short chain linker (i.e., succinic acid as previously reported) results in improved systemic release of the drug and systemic exposure. Incorporation of the self-immolative group enhances release of the pharmaceutical agent in the systemic circulation. While the self-immolative group may reduce lymphatic drug transport, it has been found for the first time that, even in the face of reduced lymphatic transport, systemic drug exposure is enhanced, likely by virtue of enhanced drug release in the systemic circulation. It was further found that methyl substitution of the carbon atoms in the linker between the self-immolative group and the glyceride unit may be employed to increase stability in the GI tract, increase lymphatic transport, and yet retain good conversion in the systemic circulation.

In this specification a number of terms are used which are well known to a skilled addressee. Nevertheless, for the purposes of clarity a number of terms will be defined.

In this specification, unless otherwise defined, the term "optionally substituted" is taken to mean that a group may or may not be further substituted with one or more groups selected from hydroxyl, alkyl, alkoxy, alkoxycarbonyl, alkenyl, alkenyloxy, alkynyl, alkynyloxy, amino, aminoacyl, thio, arylalkyl, arylalkoxy, aryl, aryloxy, acylamino, carboxy, cyano, halogen, nitro, sulfo, phosphono, phosphorylamino, phosphinyl, heteroaryl, heteroaryloxy, heterocyclyl, heterocycloxy, trihalomethyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclyl, amino, and unsymmetric di-substituted amines having different substituents selected from alkyl, aryl, heteroaryl and heterocyclyl.

As used herein, the term "alkyl", used either alone or in compound words, denotes straight chain or branched alkyl. Prefixes such as "$C_2$-$C_{20}$" are used to denote the number of carbon atoms within the alkyl group (from 2 to 20 in this case). Examples of straight chain and branched alkyl include methyl, ethyl, n-propyl, isopropyl, n-butyl, sec-butyl, t-butyl, n-pentyl, hexyl, heptyl, 5-methylheptyl, 5-methylhexyl, octyl, nonyl, decyl, undecyl, dodecyl and docosyl ($C_{22}$).

As used herein, the term "alkenyl", used either alone or in compound words, denotes straight chain or branched hydrocarbon residues containing at least one carbon to carbon double bond including ethylenically mono-, di- or polyunsaturated alkyl groups as previously defined. Preferably the alkenyl group is a straight chain alkenyl group. Prefixes such as "$C_2$-$C_{20}$" are used to denote the number of carbon atoms within the alkenyl group (from 2 to 20 in this case). Examples of alkenyl include vinyl, allyl, 1-methylvinyl, butenyl, iso-butenyl, 3-methyl-2-butenyl, 1-pentenyl, 1-hexenyl, 3-hexenyl, 1-heptenyl, 3-heptenyl, 1-octenyl, 1-nonenyl, 2-nonenyl, 3-nonenyl, 1-decenyl, 3-decenyl, 1,3-butadienyl, 1,4-pentadienyl, 1,3-hexadienyl, 1,4-hexadienyl and 5-docosenyl ($C_{22}$).

As used herein, the term "alkynyl", used either alone or in compound words, denotes straight chain or branched hydrocarbon residues containing at least one carbon to carbon triple bond. Preferably the alkynyl group is a straight chain alkynyl group. Prefixes such as "$C_2$-$C_{20}$" are used to denote the number of carbon atoms within the alkenyl group (from 2 to 20 in this case).

As used herein, terms such as "heterocycle" or "heterocyclic group", used either alone or in compound words, denotes a saturated, partially unsaturated or fully unsaturated monocyclic, bicyclic or fused polycyclic ring systems containing at least one heteroatom selected from the group consisting of nitrogen, sulfur and oxygen. Prefixes such as "$C_5$-$C_8$" are used to denote the number of carbon atoms within the cyclic portion of the group (from 5 to 8 in this case). Examples of suitable heterocyclic substituents include, but are not limited to, pyrrole, furan, benzofuran, benzothiazole, imidazole, benzimidazole, imidazoline, pyrazole, pyrazoline, triazole, oxazole, oxazoline, isoxazole, isoxazoline, furazan, oxadiazole, piperidine, pyridine, pyrimidine, pyridazine and pyrazine, each of which may be further substituted with 1 to 3 substituents.

As used herein, terms such as "aryl" or "aromatic cyclic group" denotes any single- or polynuclear, conjugated or fused residues of aromatic hydrocarbon ring systems. Prefixes such as "$C_5$-$C_8$" are used to denote the number of carbon atoms within the cyclic portion of the aryl group (from 5 to 8 in this case). Examples of aryl include phenyl (single nuclear), naphthyl (fused polynuclear), biphenyl (conjugated polynuclear) and tetrahydronaphthyl (fused polynuclear).

As used here in, the term "linker" denotes the portion of the compound spanning from "X" to "L" for compounds of the formula (I) as described herein, joining the pharmaceutical agent to the glyceride unit.

As used herein, the term "self-immolative group" defines a chemical moiety that forms a scissile bond with the linker and a stable bond with the pharmaceutical agent, wherein the bond with the pharmaceutical agent becomes labile upon cleavage of the linker. Examples of self-immolative groups include, but are not limited to acetal self-immolative groups, carboxyacetal self-immolative groups, carboxy(methylacetal) self-immolative groups, para-hydroxybenzyl carbonyl self-immolative groups, flipped ester self-immolative groups and trimethyl lock self-immolative groups. A number of other suitable self-immolative groups are known in the art as described, for example, in C. A. Blencowe et al., Polym. Chem. 2011, 2, 773-790 and F. Kratz et al., ChemMedChem. 2008, 3(1), 20-53.

As used here in, the term "pharmaceutical agent" denotes any pharmaceutically active agent or imaging (contrasting) agent which would benefit from transport via the intestinal lymphatic system, for example, to avoid first pass metabolism or for targeted delivery within the lymphatic system.

Examples of suitable pharmaceutically active agents include, but are not limited to, testosterone, mycophenolic acid (MPA), buprenorphine, oestrogens (estrogen), opiates such as morphine, tetrahydrocannabinol (THC), cannabidiol, metoprolol, raloxifene, alphaxolone, statins such as atorvastatin, pentazocine, propranolol, L-DOPA, lidocaine, chlorpromazine, sertraline, amitriptyline, nortriptyline, pentazocine, glyceryl trinitrate, oxprenolol, labetalol, salbutamol, epitiostanol, melphalan, lovastatin, non-steroidal anti-inflammatory medications (NSAIDS, such as aspirin, ibuprofen, naproxen), COX-2 inhibitors (such as celecoxib), corticosteroid anti-inflammatory medications (such as prednisolone, prednisone, dexamethasone), anti-malarial medications (such as hydroxychloroquine), nitrosoureas, methotrexate, dactinomycin, anthracyclines (such as daunorubicin), mitomycin C, bleomycin, mithramycin, drugs acting on immunophilins (such as cyclosporin, tacrolimus, sirolimus), sulfasalazine, leflunomide, mycophenolate, opioids, fingolimod, myriocin, chlorambucil, doxorubicin, nelarabine, cortisone, dexamethasone, prednisone, pralatrexate, vinblastine, bortezomib, nelarabine, daunorubicin hydrochloride, clofarabine, cytarabine, dasatinib, imatinibmesylate, ponatinib hydrochloride, vincristine sulfate, bendamustine hydrochloride, fludarabine phosphate, bosutinib, nilotinib, omacetaxine mepesuccinate, capecitabine, paclitaxel, gemcitabine, fulvestrant, tamoxifen, lapatinib, toremifene, ixabepilone, eribulin, albendazole, ivermectin, diethylcarbamazine, albendazole, doxycycline, closantel, maraviroc, enfuvirtide, deoxythymidine, zidovudine, stavudine, didanosine, zalcitabine, abacavir, lamivudine, emtricitabine, tenofovir, delavirdine, rilpivirine, raltegravir, elvitegravir, lopinavir, indinavir, nelfinavir, amprenavir, ritonavir, acyclovir and pharmaceutically active peptides.

Examples of suitable imaging agents include, but are not limited to, fluorophores such as the Alexa Fluor series of optical imaging probes for fluorescence microscopy or where the fluorophore has emission spectra in the infra-red range, for in vivo imaging; gamma emitters that can be used for positron emission tomography (PET), such as fluorodeoxyglucose, or chelating agents in order to chelate magnetic resonance imaging probes such as gadolinium or iron.

For the avoidance of any doubt, reference to "a length equivalent to a linear $C_{20}$alkyl group" refers to the length that 20 singularly bonded carbon atoms would theoretically span.

In some preferred embodiments of the invention, and with reference to the general formula (I) or (II), one or more of the following definitions apply:
a) $R^1$ and $R^2$ independently represent H, or a residue of a $C_2$-$C_{28}$ fatty acid.
b) $R^1$ represents H and $R^2$ represents a residue of a $C_2$-$C_{28}$ fatty acid.
c) $R^2$ represents H and $R^1$ represents a residue of a $C_2$-$C_{28}$ fatty acid.
d) $R^1$ and $R^2$ each represent palmitic acid.
e) —X— is —O—.
f) —X— is —NH—.
g) —X— is —S—.
h) -L- is —OC(O)—.
i) —Y— represents an optionally substituted —$C_1$-$C_{20}$alkylC(O)OCH$_2$—, —$C_2$-$C_{20}$alkenylC(O)OCH$_2$— or —$C_2$-$C_{20}$alkynylC(O)OCH$_2$— group when -L- is —OC(O)—; wherein one or more of the carbon atoms in the alkyl, alkenyl or alkynyl group may be replaced with NH, S, O, a $C_5$-$C_8$ aromatic or aliphatic cyclic group or a $C_5$-$C_8$ aromatic or aliphatic heterocyclic group, provided that the alkyl, alkenyl or alkynyl group does not exceed a length equivalent to a linear $C_{20}$alkyl group.

j) —Y— represents a —C$_1$-C$_{20}$alkylC(O)OCH$_2$—, —C$_2$-C$_{20}$alkenylC(O)OCH$_2$— or —C$_2$-C$_{20}$alkynylC(O)OCH$_2$— group optionally substituted with alkyl.

k) —Y— represents a —C$_1$-C$_{20}$alkylC(O)OCH$_2$—, —C$_2$-C$_{20}$alkenylC(O)OCH$_2$— or —C$_2$-C$_{20}$alkynylC(O)OCH$_2$— group optionally substituted with methyl.

l) -L- is —X'—.

m) —Y— represents an optionally substituted —C$_1$-C$_2$alkylC(O)R$^3$— group or a —C$_2$alkenylC(O)R$^3$— or —C$_2$alkynylC(O)R$^3$— group.

n) —Y— represents a —C$_1$-C$_2$alkylC(O)R$^3$— group optionally substituted with alkyl.

o) —Y— represents a —C$_1$-C$_2$alkylC(O)R$^3$— group optionally substituted with methyl.

p) R$^3$ is a self-immolative group selected from an acetal, carboxyacetal, carboxy(methylacetal), trimethyl lock, p-hydroxybenzylcarbonyl or flipped-ester self-immolative group.

n) X' is O.

o) X' is S.

p) X' is N(R$^4$).

q) X' is N(H)S(O)$_2$.

r) R$^4$ is H.

s) R$^4$ is C$_1$-C$_1$alkyl.

t) R$^4$ is methyl.

In one embodiment, L is X' and —Y— represents optionally substituted —C$_1$alkylC(O)R$^3$—.

Accordingly, in another embodiment, the present invention provides compounds of the formula (I) represented by the formula (II):

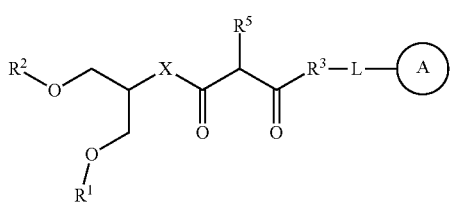

wherein
R$^1$, R$^2$, and —X—, are as defined for formula (I);
R$^3$ is a self-immolative group;

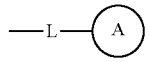

represents a residue of a pharmaceutical agent;
L- is —X'—;
X' is O, S, N(R$^4$) or N(H)S(O)$_2$;
R$^4$ is H or C$_1$-C$_1$alkyl;
R$^5$ is selected from hydrogen and C$_1$-C$_1$alkyl; or
pharmaceutically acceptable salts thereof.

In another embodiment, L is X' and —Y— represents an optionally substituted —C$_2$alkylC(O)R$^3$—.

Accordingly, in a further embodiment, the present invention provides compounds of the formula (I) represented by the formula (III):

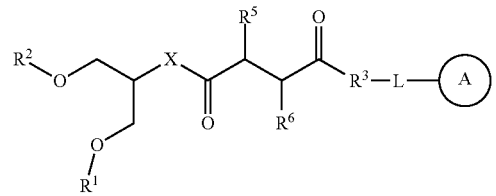

wherein
R$^1$, R$^2$, and —X—, are as defined for formula (I);
R$^3$ is a self-immolative group;

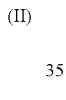

represents a residue of a pharmaceutical agent;
L- is —X'—;
X' is O, S, N(R$^4$) or N(H)S(O)$_2$;
R$^4$ is H or C$_1$-C$_4$alkyl;
R$^5$ and R$^6$ are individually selected from hydrogen and C$_1$-C$_4$alkyl; or
pharmaceutically acceptable salts thereof.

In another embodiment compounds of the formula (III) are selected from those compounds listed in Table 1.

TABLE 1

Compounds of formula (III):

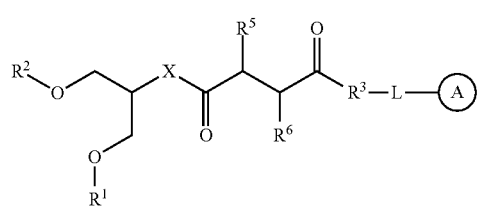

| Compound No. | R$^1$ & R$^2$ | X | R$^5$ | R$^6$ | R$^3$ | L | A |
|---|---|---|---|---|---|---|---|
| 1 | C(O)C$_{15}$H$_{31}$ | O | H | H | CASI[1] | NMethyl | Sertraline |
| 2 | C(O)C$_{15}$H$_{31}$ | O | H | H | CMSI[2] | NMethyl | Sertraline |
| 3 | C(O)C$_{15}$H$_{31}$ | O | H | H | TML[3] | NMethyl | Sertraline |
| 4 | C(O)C$_{15}$H$_{31}$ | O | H | H | CAST | O | Buprenorphine |
| 5 | C(O)C$_{15}$H$_{31}$ | O | H | H | CMSI | O | Buprenorphine |
| 6 | C(O)C$_{15}$H$_{31}$ | O | H | H | TML | O | Buprenorphine |
| 7 | C(O)C$_{15}$H$_{31}$ | O | H | H | FSI-5[4] | O | Buprenorphine |

TABLE 1-continued

Compounds of formula (III):

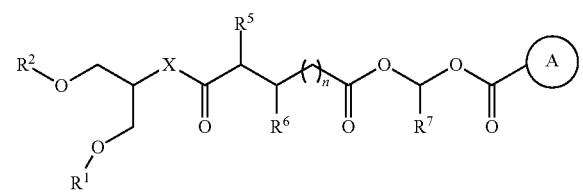

(III)

| Compound No. | R¹ & R² | X | R⁵ | R⁶ | R³ | L | A |
|---|---|---|---|---|---|---|---|
| 8 | $C(O)C_{15}H_{31}$ | O | Methyl | H | FSI-5 | O | Buprenorphine |
| 9 | $C(O)C_{15}H_{31}$ | O | H | H | FSI-5 | O | Metoprolol |

[1]CASI = a carboxyacetal self-immolative group;
[2]CMSI = a carboxy(methylacetal) self-immolative group;
[3]TML = a trimethyl lock self-immolative group;
[4]FSI-5 = a flipped ester self-immolative group liberating pharmaceutical agent A via loss of a 5-carbon lactone.

In another embodiment, L is —OC(O)— and —Y— represents optionally substituted —$C_1$-$C_{20}$alkylC(O)OCH$_2$—, —$C_2$-$C_{20}$alkenylC(O)OCH$_2$— or —$C_2$-$C_{20}$alkynylC(O)OCH$_2$— group; wherein one or more of the carbon atoms in the alkyl, alkenyl or alkynyl group may be replaced with NH, S, O, a $C_5$-$C_8$ aromatic or aliphatic cyclic group or a $C_5$-$C_8$ aromatic or aliphatic heterocyclic group, provided that the alkyl, alkenyl or alkynyl group does not exceed a length equivalent to a linear $C_{20}$alkyl group.

Accordingly, in another embodiment, the present invention provides compounds of the formula (I) represented by the formula (IV):

(IV)

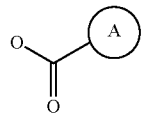

wherein
R¹, R² and —X—, are as defined for formula (I);

represents a residue of a pharmaceutical agent;
R⁵ and R⁶ are individually selected from hydrogen and $C_1$-$C_4$alkyl;
R⁷ is hydrogen or $C_1$-$C_4$alkyl; and
n is from 0 to 18; or
pharmaceutically acceptable salts thereof.

In another embodiment compounds of the formula (IV) are selected from those compounds listed in Table 2.

TABLE 2

Compounds of formula (IV):

(IV)

| Compound No. | R¹ & R² | X | R⁵ | R⁶ | R⁷ | A | n |
|---|---|---|---|---|---|---|---|
| 10 | $C(O)C_{15}H_{31}$ | O | H | Methyl | H | MPA | 1 |
| 11 | $C(O)C_{15}H_{31}$ | O | H | Methyl | Methyl | MPA | 1 |

In one embodiment, the pharmaceutical agent is testosterone or a derivative or analogue thereof. Testosterone replacement therapy (TRT) is commonly used for patients with hypogonadism (a disorder characterised by abnormally low serum testosterone levels) to restore their serum testosterone levels to the normal range and thus relieve many of the symptoms of hypogonadism such as mood disturbance, sexual dysfunction and so on.

Accordingly, in one embodiment, the present invention provides compounds of the formula (I) represented by the formula (V):

(V)

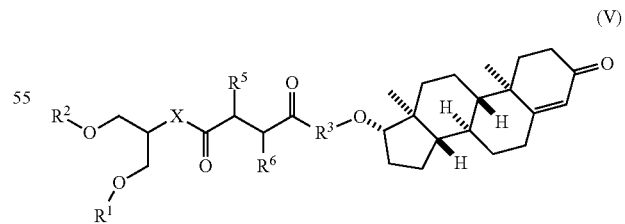

wherein R¹, R² and —X— are as defined for formula (I);
R⁵ and R⁶ are individually selected from hydrogen and $C_1$-$C_4$alkyl; and
R³ is a self-immolative group; or
pharmaceutically acceptable salts thereof.

In another embodiment compounds of the formula (V) are selected from those compounds listed in Table 3.

TABLE 3

Compounds of formula (V):

![Formula V structure]

| Compound No. | $R^1$ | $R^2$ | X | $R^5$ | $R^6$ | $R^3$ |
|---|---|---|---|---|---|---|
| 12 | $C(O)C_{15}H_{31}$ | $C(O)C_{15}H_{31}$ | O | H | H | ASI[1] |
| 13 | $C(O)C_{15}H_{31}$ | $C(O)C_{15}H_{31}$ | O | Methyl | H | ASI |
| 14 | $C(O)C_{15}H_{31}$ | $C(O)C_{15}H_{31}$ | O | H | Methyl | ASI |
| 15 | $C(O)C_{15}H_{31}$ | $C(O)C_{15}H_{31}$ | O | H | H | TML[2] |
| 16 | $C(O)C_{15}H_{31}$ | $C(O)C_{15}H_{31}$ | O | H | H | PHB[3] |
| 17 | $C(O)C_{15}H_{31}$ | $C(O)C_{15}H_{31}$ | O | H | H | FSI-4[4] |
| 18 | $C(O)C_{15}H_{31}$ | $C(O)C_{15}H_{31}$ | O | H | H | FSI-5[5] |
| 19 | $C(O)C_{15}H_{31}$ | $C(O)C_{15}H_{31}$ | O | Methyl | H | FSI-5 |
| 20 | $C(O)C_{15}H_{31}$ | $C(O)C_{15}H_{31}$ | O | H | H | CMSI[6] |

[1]ASI = an acetal self-immolative group;
[2]TML = a trimethyl lock self-immolative group;
[3]PHB = a p-hydroxybenzylcarbonyl self-immolative group;
[4]FSI-4 = a flipped ester self-immolative group liberating pharmaceutical agent A via loss of a 4-carbon lactone;
[5]FSI-5 = a flipped ester self-immolative group liberating pharmaceutical agent A via loss of a 5-carbon lactone;
[6]CMSI = a carboxy(methylacetal) self-immolative group.

In another embodiment, the present invention provides a method of treating or preventing a disease or disorder in which increased testosterone levels are beneficial, comprising administering to the subject in need thereof a therapeutically effective amount of a compound according to formula (V).

In a further embodiment, the present invention provides the use of a compound according to the formula (V) in the manufacture of a medicament for treating or preventing a disease or disorder in which increased testosterone levels are beneficial.

In yet another embodiment, the present invention provides a compound of formula (V) for use in the treatment or prevention of a disease or disorder in which increased testosterone levels are beneficial.

Diseases and disorders in which increased testosterone levels may be beneficial include, but are not limited to, hypogonadism, anaemia due to bone marrow failure, anaemia due to renal failure, chronic respiratory failure, chronic cardiac failure, steroid-dependent autoimmune disorders, AIDS wasting, hereditary angioedema or urticaria, terminal breast cancer or menopause.

In another embodiment, the present invention provides a method of promoting lymphatic transport and systemic release of a pharmaceutical agent comprising conjugating to the pharmaceutical compound a prodrug residue of the formula (VI):

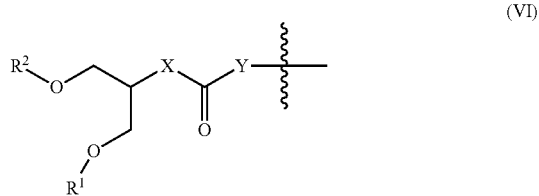

(VI)

wherein
$R^1$ and $R^2$ independently represent H or a residue of a $C_2$-$C_{28}$ fatty acid;
—X— is selected from —O—, —NH— and —S—;
—Y— represents an optionally substituted —$C_1$-$C_2$alkylC(O)$R^3$— group or a —$C_2$alkenylC(O)$R^3$— or —$C_2$alkynylC(O)$R^3$— group;
$R^3$ is a self-immolative group; and
∼∼∼ denotes the point where the linker is conjugated to the pharmaceutically active agent; or
pharmaceutically acceptable salts thereof.

In one embodiment the linker comprising "Y" and "$R^3$" for the compounds as hereinbefore defined will be selected to facilitate stable transport of the pharmaceutical agent to the intestinal lymph. In another embodiment Y and $R^3$ will be selected to facilitate release of the pharmaceutical agent in the lymph, lymphocytes, lymphoid tissues, tissues with high lipase activity such as adipose tissue, certain cancers, the liver or in the systemic circulation. In yet another embodiment Y and $R^3$ are selected to both facilitate stable transport of the pharmaceutical agent to the intestinal lymph and to facilitate release of the pharmaceutical agent in the lymph, lymphocytes, lymphoid tissues, tissues with high lipase activity such as adipose tissue, certain cancers, the liver or in the systemic circulation.

Compounds of the present invention are useful for the stable transport of pharmaceutical agents to the intestinal lymph and release of the pharmaceutical agents in the lymph, lymphocytes, lymphoid tissues, tissues with high lipase activity such as adipose tissue, certain cancers, the liver or in the systemic circulation. Compounds of the present invention are particularity useful for the transport and release of pharmaceutical agents that benefit from avoidance of first pass metabolism, for example, compounds that exhibit greater than 50% first pass metabolism. In one embodiment, it is envisaged that the pharmaceutical agent will exhibit greater than 60% first pass metabolism. In another embodiment, the pharmaceutical agent will exhibit greater than 70% first pass metabolism. In a further embodiment, the pharmaceutical agent will exhibit greater than 80% first pass metabolism. In yet another embodiment, the pharmaceutical agent will exhibit greater than 90% first pass metabolism.

Pharmaceutical agents that may benefit from the stable transport to the intestinal lymph and release in the lymph, lymphocytes, lymphoid tissues, tissues with high lipase activity such as adipose tissue, certain cancers, the liver or in the systemic circulation include, but are not limited to, testosterone, mycophenolic acid, oestrogens (estrogen), morphine, tetrahydrocannabinol, cannabidiol, metoprolol, raloxifene, alphaxolone, statins such as atorvastatin, pentazocine, propranolol, L-DOPA, buprenorphine, midazolam, lidocaine, chlorpromazine, amitriptyline, nortriptyline, pentazocine, isosorbidedinitrate, glyceryl trinitrate, oxprenolol, labetalol, verapamil, salbutamol, epitiostanol, melphalan, lovastatin and pharmaceutically active peptides.

Compounds of the present invention are also useful for the targeted release of the pharmaceutical agent within the lymphatic system, for example, in the lymph, lymphocytes and lymphoid tissues, as well as in tissues with high lipase activity such as adipose tissue, certain cancers, or the liver.

Pharmaceutical agents that may benefit from targeted release within the lymphatic system or in adipose tissue include, but are not limited to, non-steroidal anti-inflammatory medications (NSAIDS, such as aspirin, ibuprofen, naproxen), COX-2 inhibitors (such ascelecoxib), corticosteroid anti-inflammatory medications (such as prednisolone, dexamethasone), anti-malarial medications (such as hydroxychloroquine), cyclophosphamide, PPAR agonists (such as the fibrates), nitrosoureas, platinum, methotrexate, azathioprine, mercaptopurine, fluorouracil, dactinomycin, anthracyclines, mitomycin C, bleomycin, mithramycin, drugs acting on immunophilins (such as ciclosporin, tacrolimus, sirolimus), sulfasalazine, leflunomide, mycophenolate, opioids, fingolimod, myriocin, chlorambucil, doxorubicin, nelarabine, cortisone, dexamethasone, prednisone, pralatrexate, vinblastine, bortezomib, thiotepa, nelarabine, daunorubicin hydrochloride, clofarabine, cytarabine, dasatinib, imatinibmesylate, ponatinib hydrochloride, vincristine sulfate, bendamustine hydrochloride, fludarabine phosphate, bosutinib, nilotinib, omacetaxine, mepesuccinate, anastrozole, capecitabine, letrozole, paclitaxel, gemcitabine, fulvestrant, tamoxifen, lapatinib, toremifene, ixabepilone, eribulin, albendazole, ivermectin, diethylcarbamazine, doxycycline, closantel, maraviroc, enfuvirtide, deoxythymidine, zidovudine, stavudine, didanosine, zalcitabine, abacavir, lamivudine, emtricitabine, tenofovir, nevirapine, delavirdine, efavirenz, rilpivirine, raltegravir, elvitegravir, lopinavir, indinavir, nelfinavir, amprenavir, ritonavir, acyclovir and immunosuppressants such as mycophenolic acid, cyclosporine, tacrolimus and sirolimus.

As a general strategy, compounds of the present invention may be synthesised via one of the following routes:

Scheme 1. Synthesis of compounds of the general formula (II).

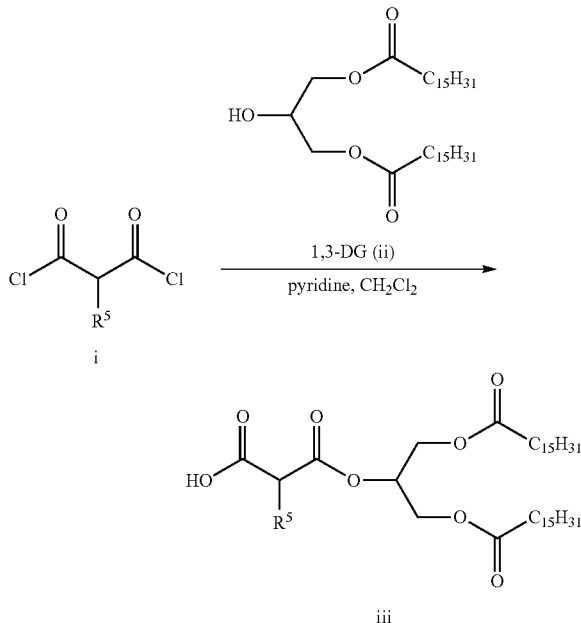

Diacid chlorides i, which are readily available from the corresponding malonic acids, can be reacted with diglyceride ii in the presence of pyridine to give acid-triglyceride (acid-TG) iii (see Scheme 1).

Scheme 2. Synthesis of compounds of the general formula (III).

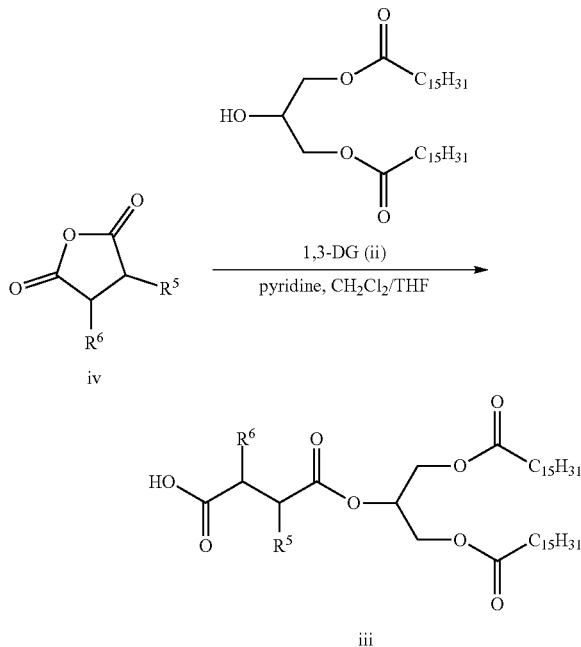

In cases where acid anhydride iv is available, acid-TG iii can be generated by ring-opening with diglyceride ii in the presence of pyridine (Scheme 2). This method works best when $R^5$ and $R^6$ of acid anhydride iv are identical, but will result in a regioisomeric mixture of acid-TG iii when $R^5$ and $R^6$ differ from each other. Consequently, other methods, such as that outlined in Scheme 3, should be employed in this circumstance.

Scheme 3. Synthesis of compounds of the formula (III) where $R^5$ = Me, $R^6$ = H.

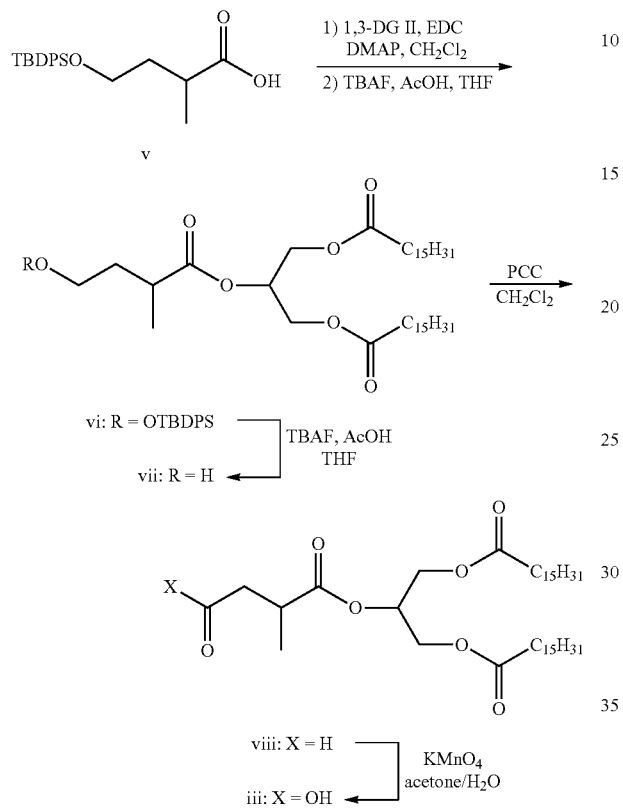

To obtain acid-TG iii as a single regioisomer in the specific example where $R^5$=Me and $R^6$=H, the known carboxylic acid v (Lienard, B. M. R. et al., Org. Biomol. Chem. 2008, 6, (13), 2282-2292) can be used as a starting point (see Scheme 3). Coupling of acid v with 1,3-DG ii under standard conditions produces TBDPS protected triglyceride vi, which can be treated with TBAF and AcOH to afford alcohol vii. A two-step oxidation process (PCC, then $KMnO_4$) can then be used to transform alcohol vii into the desired acid-TG iii via the intermediate aldehyde viii.

Scheme 4. Synthesis of compounds of the general formulae (III) wherein $R^3$ is an acetal self-immolative group and X′ = O.

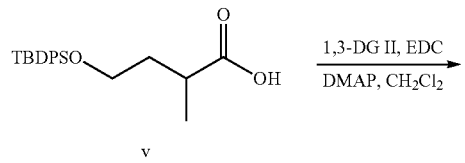

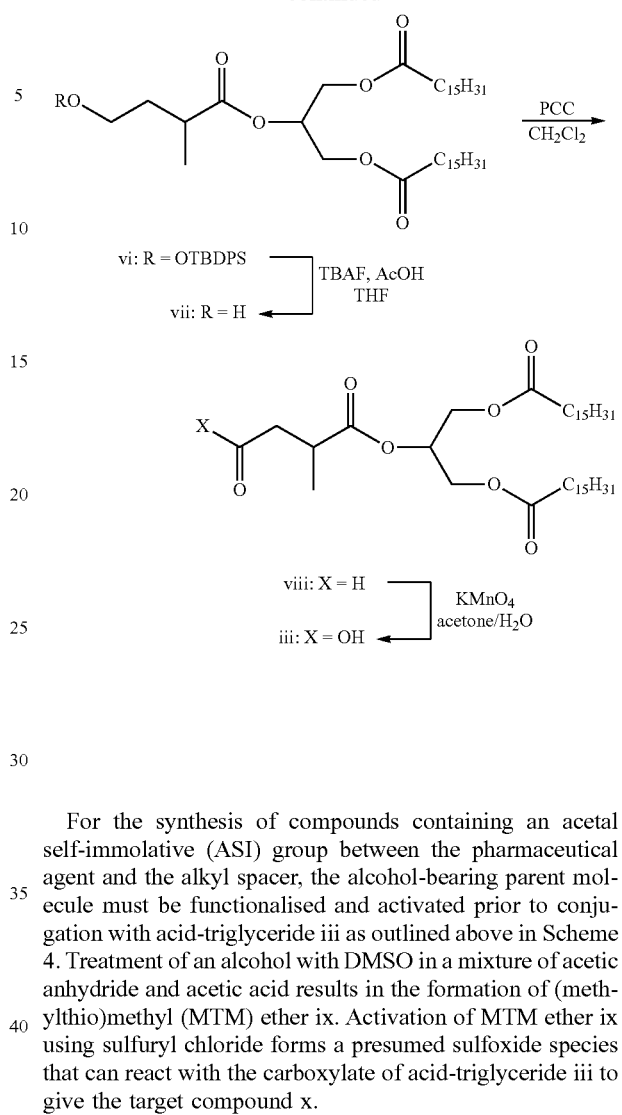

For the synthesis of compounds containing an acetal self-immolative (ASI) group between the pharmaceutical agent and the alkyl spacer, the alcohol-bearing parent molecule must be functionalised and activated prior to conjugation with acid-triglyceride iii as outlined above in Scheme 4. Treatment of an alcohol with DMSO in a mixture of acetic anhydride and acetic acid results in the formation of (methylthio)methyl (MTM) ether ix. Activation of MTM ether ix using sulfuryl chloride forms a presumed sulfoxide species that can react with the carboxylate of acid-triglyceride iii to give the target compound x.

Scheme 5. Synthesis of compounds of the formula (III) wherein $R^3$ is a carboxyacetal (CASI) or carboxy(methylacetal) (CMSI) self-immolative group and X′ is O or $N(R^4)$.

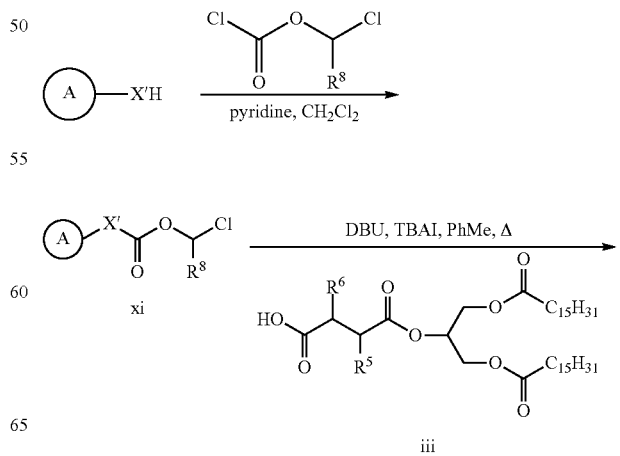

-continued

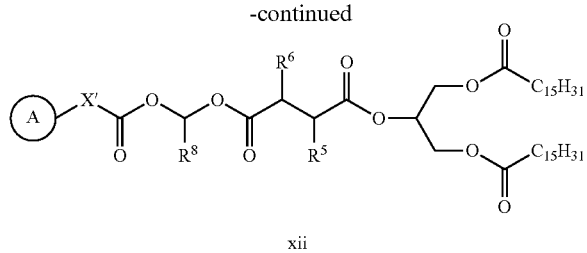

xii

In cases where the pharmaceutical agent contains an alcohol, phenol or amine (primary or secondary) functional group, a modified version of the acetal self-immolative group can be used where an additional carboxy group is included. Reaction of the parent drug with a chloroalkyl chloroformate gives chloroalkyl carbonates or carbamates xi (see Scheme 5). Displacement of the halide leaving group is then accomplished by treatment with the carboxylate derived from acid-TG iii in refluxing toluene to afford the target compound xii.

Scheme 6. Synthesis of compounds of the formula (III) wherein $R^3$ is a trimethyl-lock (TML) self-immolative group and $X' = O$, $NR^4$ or $S(O)_2NH$.

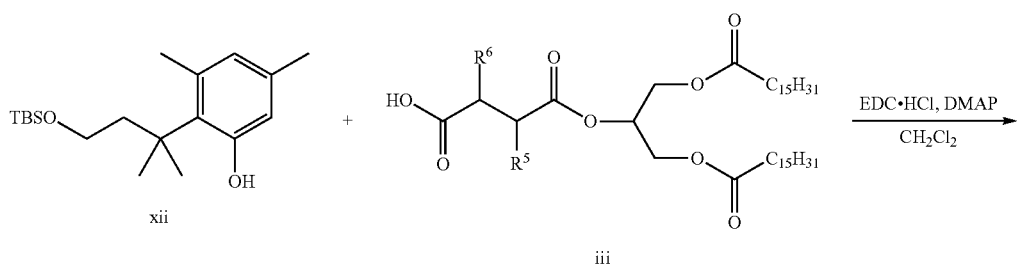

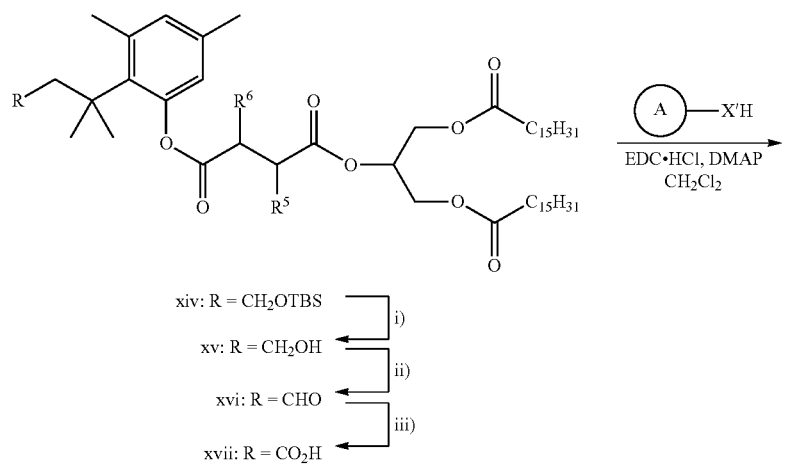

xiv: R = CH$_2$OTBS
xv: R = CH$_2$OH
xvi: R = CHO
xvii: R = CO$_2$H i)
ii)
iii)

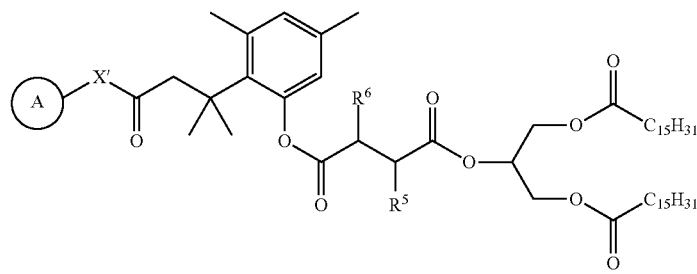

xxviii i) 10-CSA, CH$_2$Cl$_2$/MeOH; ii) PCC, CH$_2$Cl$_2$; iii) KMnO$_4$, acetone/H$_2$O.

For the synthesis of prodrugs containing a trimethyl lock (TML) self-immolative group (Levine, M. N.; Raines, R. T. *Chem. Sci.* 2012, 3, 2412-2420) between the pharmaceutical agent and the alkyl spacer to facilitate systemic release of the parent molecule, the acid-triglyceride iii must be functionalised with the TML moiety prior to conjugation with a pharmaceutical agent as outlined in Scheme 6. Coupling of acid-TG iii with TML phenol xiii under standard conditions gives triglyceride xiv, which can be deprotected under acidic conditions (10-camphorsulfonic acid) to give alcohol xv. Sequential oxidation of alcohol xv firstly to aldehyde xvi and then acid xvii, followed by coupling to either an alcohol, amine or sulfonamide-containing pharmaceutical agent under standard conditions can give the target compound xviii.

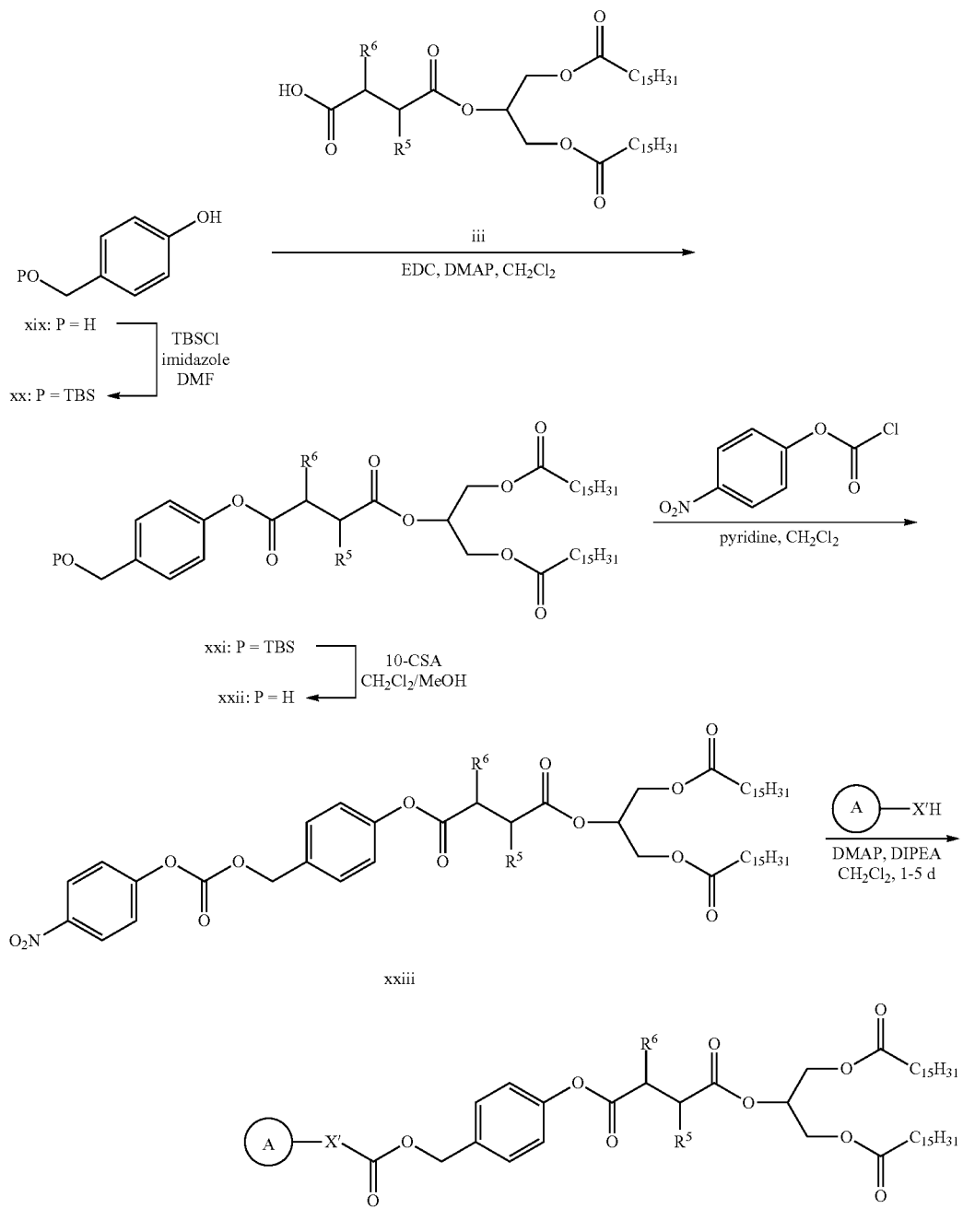

Scheme 7. Synthesis of compounds of the formula (III) wherein $R^3$ is a p-hydroxybenzyl carbonyl (PHB) self-immolative group and $X' = O$, S or $NR^4$.

For the synthesis of compounds containing a p-hydroxybenzyl (PHB) carbonyl self-immolative group, the primary hydroxyl group of p-hydroxybenzyl alcohol (xix) is first protected as a silyl ether and the free phenolic hydroxyl group coupled with acid-TG iii to give PHB triglyceride xxi (see Scheme 7). After removal of the silicon protecting group, primary alcohol xxii can be activated by treatment with p-nitrophenyl (PNP) chloroformate to give PNP carbonate xxiii. Displacement of the PNP group is then achieved by reaction with a pharmaceutical agent (A-X'H) under basic conditions to give the desired compound xxiv.

Scheme 9. Synthesis of compounds of the formula (V).

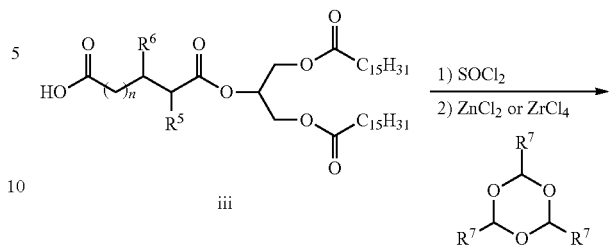

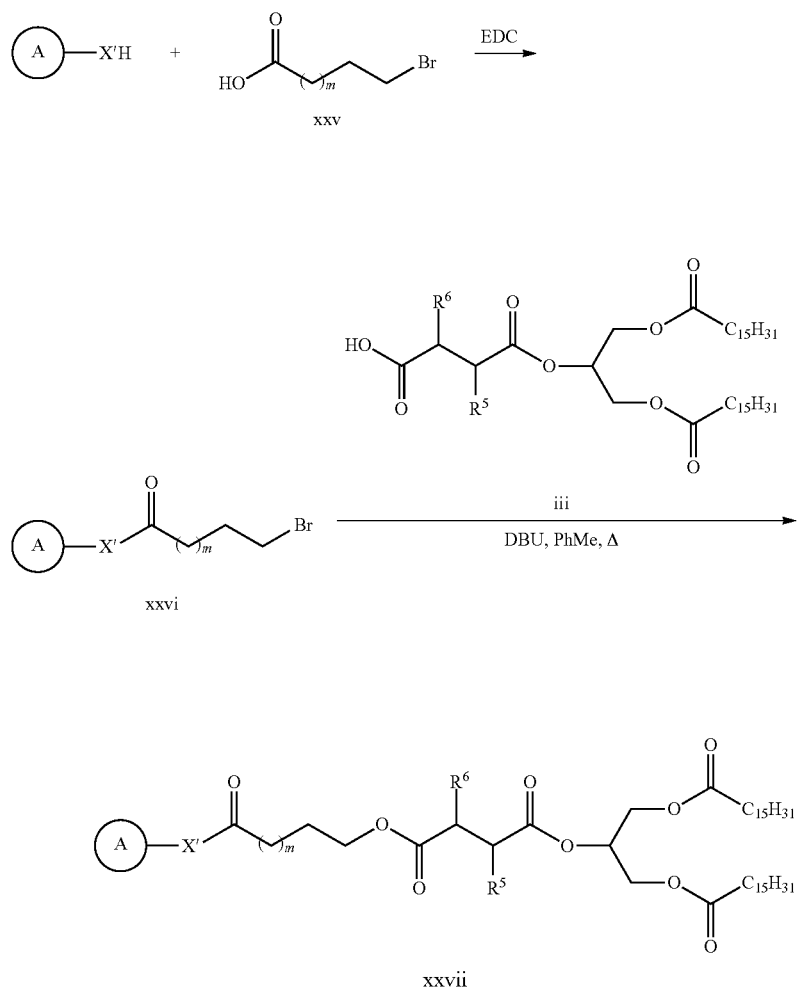

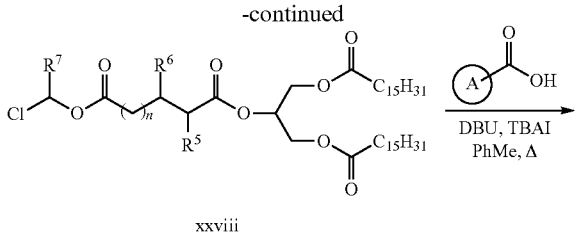

The flipped-ester self-immolative (FSI) group has been designed to liberate the free pharmaceutical agent by a cyclisation mechanism, resulting in loss of either a four-carbon (FSI-4) or five-carbon (FSI-5) lactone. FSI prodrugs can be synthesised by coupling the pharmaceutical agent (A-X'H) with either 4-bromobutyric acid (m=1) or 5-bromovaleric acid (m=2) (xxv) to give bromide xxvi (see Scheme 8). Displacement of bromide xxvi using the carboxylate derived from acid-TG iii generates the desired ester bond in target compound xxvii.

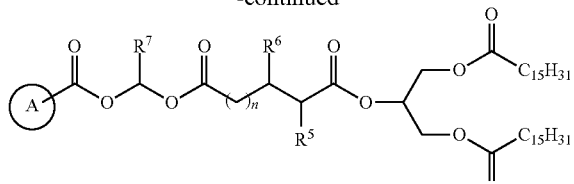

R⁸ = H, Me

In cases where the pharmaceutical agent contains a carboxylic acid, acid-TG iii must be converted to the corresponding acid chloride, and then treated with either trioxane ($R^7$=H) or paraldehyde ($R^7$=Me) in the presence of $ZrCl_4$ or $ZnCl_2$ to afford chloroalkyl ester xxviii (see Scheme 9). Displacement of the halide can then be achieved by reaction with the carboxylate derived from the parent drug, providing target compound xxix.

Where the compounds of the present invention require purification, techniques such as recrystallisation and chromatographic techniques including high-performance liquid chromatography (HPLC) and normal phase or reversed-phase silica gel chromatography may be used. The compounds may be characterised by nuclear magnetic resonance (NMR) mass spectrometry and/or other appropriate methods.

It will be understood that the compounds of the present invention may exist in one or more stereoisomeric forms (e.g. diastereomers). The present invention includes within its scope all of these stereoisomeric forms either isolated (in, for example, enantiomeric isolation), or in combination (including racemic mixtures and diastereomic mixtures).

The invention thus also relates to compounds in substantially pure stereoisomeric form, e.g., greater than about 90% de, such as about 95% to 97% de, or greater than 99% de, as well as mixtures, including racemic mixtures, thereof. Such diastereomers may be prepared by asymmetric synthesis, for example, using chiral intermediates, or mixtures may be resolved by conventional methods, e.g., chromatography, or use of a resolving agent.

Where the compound comprises one or more functional groups that may be protonated or deprotonated (for example at physiological pH) the compound may be prepared and/or isolated as a pharmaceutically acceptable salt. It will be appreciated that the compound may be zwitterionic at a given pH. As used herein the expression "pharmaceutically acceptable salt" refers to the salt of a given compound, wherein the salt is suitable for administration as a pharmaceutical. Such salts may be formed by the reaction of an acid or a base with an amine or a carboxylic acid group respectively.

Pharmaceutically acceptable acid addition salts may be prepared from inorganic and organic acids. Examples of inorganic acids include hydrochloric acid, hydrobromic acid, sulfuric acid, nitric acid, phosphoric acid and the like. Examples of organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Pharmaceutically acceptable base addition salts may be prepared from inorganic and organic bases. Corresponding counter ions derived from inorganic bases include the sodium, potassium, lithium, ammonium, calcium and magnesium salts. Organic bases include primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine.

Acid/base addition salts tend to be more soluble in aqueous solvents than the corresponding free acid/base forms.

The compounds of the invention may be in crystalline form or as solvates (e.g. hydrates) and it is intended that both forms are within the scope of the present invention. The term "solvate" is a complex of variable stoichiometry formed by a solute and a solvent. Such solvents should not interfere with the biological activity of the solute. Solvents may be, by way of example, water, ethanol or acetic acid. Methods of solvation are generally known within the art.

The route of administration for the compounds of the present invention is intended to include oral and enteral administration. Accordingly, the active compound may be formulated with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal or sublingual tablets, troches, capsules, elixirs, suspensions, syrups, wafers, and the like. The amount of active compound in such therapeutically useful compositions is such that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the compounds of the invention may be incorporated into sustained-release preparations and formulations, including those that allow specific delivery of the pharmaceutical agent to specific regions of the gut.

Liquid formulations may also be administered enterally via a stomach or oesophageal tube.

In one embodiment the compound(s) of the invention will be administered orally with food to promote transport to the intestinal lymph.

In another embodiment the compound(s) of the invention will be co-administered orally with a lipid based formulation to promote transport to the intestinal lymph with or without co-administration with food.

Lipid based formulations for oral delivery are known in the art and may include, for example, substantially non-aqueous vehicles which typically contain one or more lipid components. The lipid vehicles and resulting lipid formulations may be usefully classified as described below according to their shared common features according to the lipid formulation classification system (LFCS) (Pouton, C. W., *Eur. J. Pharm. Sci.* 11 (Supp 2), S93-S98, 2000; Pouton, C. W., *Eur. J. Pharm. Sci.* 29 278-287, 2006).

Thus lipid vehicles, and the resulting lipid formulations, may contain oil/lipids and/or surfactants, optionally with co-solvents. Type I formulations include oils or lipids which require digestion, such as mono, di and tri-glycerides and combinations thereof. Type II formulations are water-insoluble self emulsifying drug delivery systems (SEDDS) which contain lipids and oils used in Type I formulations, with additional water insoluble surfactants. Type III formulations are SEDDS or self-microemulsifying drug delivery systems (SMEDDS) which contain lipids and oils used in Type I formulations, with additional water-soluble surfactants and/or co-solvents (Type Ma) or a greater proportion of water-soluble components (Type Mb). Type IV formulations contain predominantly hydrophilic surfactants and co-solvents (e.g. PEG, propylene glycol and diethylene glycol monoethyl ether) and are useful for drugs which are poorly water soluble but not lipophilic. Any such lipid formulation (Type I-IV) is contemplated herein.

In some embodiments, the lipid vehicle contains one or more oils or lipids, without additional surfactants, co-surfactants or co-emulsifiers, or co-solvents, that is to say consists essentially of one or more oils or lipids. In some further embodiments the lipid vehicle contains one or more oils or lipids together with one or more water-insoluble surfactants, optionally together with one or more co-solvents. In some further embodiments, the lipid vehicle contains one or more oils or lipids together with one or more water-soluble surfactants, optionally together with one or more co-solvents. In some embodiments, the lipid vehicle contains a mixture of oil/lipid, surfactant and co-solvent. In some embodiments, the lipid vehicle consists essentially of one or more surfactants/co-surfactants/co-emulsifiers, and/or solvents/co-solvents.

Examples of oils or lipids which may be used in the present invention include almond oil, babassu oil, blackcurrant seed oil, borage oil, canola oil, castor oil, coconut oil, cod liver oil, corn oil, cottonseed oil, evening primrose oil, fish oil, grape seed oil, mustard seed oil, olive oil, palm kernel oil, palm oil, peanut oil, rapeseed oil, safflower oil, sesame oil, shark liver oil, soybean oil, sunflower oil, walnut oil, wheat germ oil, avocado oil, bran oil, hydrogenated castor oil, hydrogenated coconut oil, hydrogenated cottonseed oil, hydrogenated palm oil, hydrogenated soybean oil, partially hydrogenated soybean oil, hydrogenated vegetable oil, caprylic/capric glycerides, fractionated triglycerides, glyceryl tricaprate, glyceryl tricaproate, glyceryl tricaprylate, glyceryl tricaprylate/caprate, glyceryl tricaprylate/caprate, glyceryl tricaprylate/caprate/laurate, glyceryl tricaprylate/caprate/linoleate, glyceryl tricaprylate/caprate/stearate, glyceryl trilaurate, glyceryl monolaurate, glyceryl behenate, glyceryl monolinoleate, glyceryl trilinolenate, glyceryl trioleate, glyceryl triundecanoate, glyceryl tristearate linoleic glycerides, saturated polyglycolized glycerides, synthetic medium chain triglycerides containing primarily $C_8$-$C_{12}$ fatty acid chains, medium chain triglycerides containing primarily $C_8$-$C_{12}$ fatty acid chains, long chain triglycerides containing primarily >$C_{12}$ fatty acid chains, modified triglycerides, fractionated triglycerides, and mixtures thereof.

Examples of mono and diglycerides which may be used in the present invention include glycerol mono- and diesters having fatty acid chains from 8 to 40 carbon atoms, including hydrolysed coconut oils (e.g. Capmul® MCM), hydrolysed corn oil (e.g. Maisine™35-1). In some embodiments, the monoglycerides and diglycerides are mono- or di-saturated fatty acid esters of glycerol having fatty acid chains of 8 to 18 carbon chain length (e.g. glyceryl monostearate, glyceryl distearate, glyceryl monocaprylate, glyceryl dicaprylate, glyceryl monocaprate and glyceryl dicaprate).

Suitable surfactants for use in the lipid formulations include propylene glycol mono- and di-esters of $C_8$-$C_{22}$ fatty acids, such as, but not limited to, propylene glycol monocaprylate, propylene glycol dicaprylate, propylene glycol monolaurate, sold under trade names such as Capryol® 90, Labrafac® PG, Lauroglycol® FCC, sugar fatty acid esters, such as, but not limited to, sucrose palmitate, sucrose laurate, surcrose stearate; sorbitan fatty acid esters such as, but not limited to, sorbitan laurate, sorbitan palmitate, sorbitan oleate; polyoxyethylene sorbitan fatty acid esters such as, but not limited to, polysorbate 20, polysorbate 40, polysorbate 60, and polysorbate 80, polysorbate 85; polyoxyethylene mono- and di-fatty acid esters including, but not limited to polyoxyl 40 stearate and polyoxyl40 oleate; a mixture of polyoxyethylene mono- and di-esters of $C_8$-$C_{22}$ fatty acids and glyceryl mono-, di-, and tri-esters of $C_8$-$C_{22}$ fatty acids as sold under tradenames such as Labrasol®, Gelucire® 44/14, Gelucire® 50/13, Labrafil®; polyoxyethylene castor oils compound such as, but not limited to, polyoxyl 35 castor oil, polyoxyl 40 hydrogenated castor oil, and polyoxyl 60 hydrogenated castor oil, as are sold under tradenames such as Cremophor®/Kolliphor EL, Cremophor®/Kolliphor® RH40, Cremophor®/Kolliphor® RH60; polyoxyethylene alkyl ether including but not limited to polyoxyl 20 cetostearyl ether, and polyoxyl 10 oleyl ether; DL-.alpha.-tocopheryl polyethylene glycol succinate as may be sold under the tradename; glyceryl mono-, di-, and tri-ester; a glyceryl mono-, di-, and tri-esters of $C_8$-$C_{22}$ fatty acid; a sucrose mono-, di-, and tri-ester; sodium dioctylsulfosuccinate; polyoxyethylene-polyoxypropylene copolymers such as, but not limited to poloxamer 124, poloxamer 188, poloxamer 407; polyoxyethyleneethers of $C_8$-$C_{22}$ fatty alcohols including, but not limited to polyoxyethylenelauryl alcohol, polyoxyethylenecetyl alcohol, polyoxyethylenestearyl alcohol, polyoxyethyleneoleyl alcohol as sold under tradenames such as Brij® 35, Brij® 58, Brij® 78Brij® 98, or a mixture of any two or more thereof.

A co-emulsifier, or co-surfactant, may be used in the formulation. A suitable co-emulsifier or co-surfactant may be a phosphoglyceride; a phospholipid, for example lecithin, or a free fatty acid that is liquid at room temperature, for example, iso-stearic acid, oleic acid, linoelic acid, linolenic acid, palmitic acid, stearic acid, lauric acid, capric acid, caprylic acid and caproic acid.

Suitable solvents/co-solvents include ethanol, propylene glycol, polyethylene glycol, diethylene glycol monoethyl ether and glycerol.

A polymer may also be used in the formulation to inhibit drug precipitation or to alter the rate of drug release. A range of polymers have been shown to impart these properties and are well known to those skilled in the art. Suitable polymers include hydroxypropylmethylcellulose, hydroxypropylmethylcellulose acetyl succinate, other cellulose-derived polymers such as methylcellulose; poly(meth)acrylates, such as the Eudragit series of polymers, including Eudragit E100, polyvinylpyrrolidone or others as described in e.g. Warren et al. *Mol. Pharmaceutics* 2013, 10, 2823-2848.

Formulations may be chosen specifically to provide for sustained release of the active in the gastrointestinal (GI) tract in order to control the rate of absorption. Many different approaches may be used to achieve these ends including the use of high melting point lipids that disperse/ erode slowly in the GI tract, or polymers that form a matrix that slowly erodes. These formulations may take the form of large monolithic dose forms or may be present as micro or nano-particulate matrices as described in, for example, in Mishra, Handbook of Encapsulation and Controlled Release, CRC Press, Boca Raton, (2016) ISBN 978-1-4822-3234-9, Wilson and Crowley Controlled Release in Oral Drug Delivery, Springer, N.Y., ISBN 978-1-4614-1004-1 (2011) or Wise, Handbook of Pharmaceutical Controlled Release Technology, Marcel Dekker, N.Y., ISBN 0-82467-0369-3 (2000).

Formulations may also contain materials commonly known to those skilled in the art to be included in lipid based formulations, including antioxidants, for example, butylated hydroxyanisole (BHA) or butylated hydroxytoluene (BHT) and solidifying agents such as microporous silica, for example magnesium alumino-metasilicate (Neusilin).

In another embodiment the compound(s) may be co-administered orally with an enzyme inhibitor to increase stability of the prodrug in the gastrointestinal tract or enterocyte. In certain embodiments it is envisaged that the enzyme inhibitor will inhibit pancreatic lipases, examples of which include, but are not limited to, Alli and Orlistat. In other embodiments it is envisaged that the enzyme inhibitor will inhibit cellular lipase enzymes such as monoacylglycerol lipase, an example of which includes, but is not limited to, JZL184 (4-nitrophenyl-4-[bis 1,3-benzodioxol-5-yl)(hydroxy)methyl]piperidine-1-carboxylate).

While the compounds as hereinbefore described, or pharmaceutically acceptable salts thereof, may be the sole active ingredient administered to the subject, the administration of other active ingredient(s) with the compound is within the scope of the invention. In one or more embodiments it is envisaged that a combination of two or more of the compounds of the invention will be administered to the subject.

The present invention also provides a pharmaceutical composition comprising a therapeutically effective amount of a compound as hereinbefore defined, or a pharmaceutically acceptable salt thereof, together with at least one pharmaceutically acceptable carrier or diluent.

The term "composition" is intended to include the formulation of an active ingredient with encapsulating material as carrier, to give a capsule in which the active ingredient (with or without other carrier) is surrounded by carriers.

As will be readily appreciated by those skilled in the art, the nature of the pharmaceutically acceptable carrier will depend on the nature of the condition and the mammal to be treated. It is believed that the choice of a particular carrier or delivery system could be readily determined by a person skilled in the art. In the preparation of any formulation containing the active compound care should be taken to ensure that the activity of the compound is not destroyed in the process and that the compound is able to reach its site of action without being destroyed. In some circumstances it may be necessary to protect the compound by means known in the art, such as, for example, micro encapsulation.

Those skilled in the art may readily determine appropriate formulations for the compounds of the present invention using conventional approaches. Identification of preferred pH ranges and suitable excipients, for example antioxidants, is routine in the art. Buffer systems are routinely used to provide pH values of a desired range and include carboxylic acid buffers for example acetate, citrate, lactate and succinate. A variety of antioxidants are available for such formulations including phenolic compounds such as BHT or vitamin E, reducing agents such as methionine or sulphite, and metal chelators such as EDTA.

Pharmaceutically acceptable vehicles and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

The compound(s) may also be administered with one or more additional therapeutic agents in combination. The combination may allow for separate, sequential or simultaneous administration of the compound(s) as hereinbefore described with the other active ingredient(s). The combination may be provided in the form of a pharmaceutical composition.

The term "combination", as used herein refers to a composition or kit of parts where the combination partners as defined above can be dosed dependently or independently or by use of different fixed combinations with distinguished amounts of the combination partners, i.e., simultaneously or at different time points. The combination partners can then, e.g., be administered simultaneously or chronologically staggered, that is at different time points and with equal or different time intervals for any part of the kit of parts. The ratio of the total amounts of the combination partners to be administered in the combination can be varied, e.g. in order to cope with the needs of a patient sub-population to be treated or the needs of the single patient which different needs can be due to age, sex, body weight, etc. of the patients.

It is especially advantageous to formulate the compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutically acceptable vehicle. The specification for the novel dosage unit forms of the invention are dictated by and directly dependent on (a) the unique characteristics of the active material and the particular therapeutic effect to be achieved, and (b) the limitations inherent in the art of compounding active materials for the treatment of disease in living subjects having a diseased condition in which bodily health is impaired as herein disclosed in detail.

As mentioned above the principal active ingredient may be compounded for convenient and effective administration in therapeutically effective amounts with a suitable pharmaceutically acceptable vehicle in dosage unit form. A unit dosage form can, for example, contain the principal active compound in amounts ranging from 0.25 µg to about 2000 mg. Expressed in proportions, the active compound may be present in from about 0.25 µg to about 2000 mg/mL of carrier. In the case of compositions containing supplementary active ingredients, the dosages are determined by reference to the usual dose and manner of administration of the said ingredients.

As used herein, the term "effective amount" refers to an amount of compound which, when administered according to a desired dosing regimen, provides the desired therapeutic activity. Dosing may occur once, or at intervals of minutes or hours, or continuously over any one of these periods. Suitable dosages may lie within the range of about 0.1 ng per kg of body weight to 1 g per kg of body weight per dosage. A typical dosage is in the range of 1 μg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage, such as up to 50 mg per kg of body weight per dosage.

The terms "treatment" and "treating" as used herein cover any treatment of a condition or disease in an animal, preferably a mammal, more preferably a human and includes the treatment of any disease or disorder in which increased testosterone levels are beneficial. The terms "prevention" and "preventing" as used herein cover the prevention or prophylaxis of a condition or disease in an animal, preferably a mammal, more preferably a human and includes preventing any disease or disorder in which increased testosterone levels are beneficial.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

The reference in this specification to any prior publication (or information derived from it), or to any matter which is known, is not, and should not be taken as an acknowledgment or admission or any form of suggestion that prior publication (or information derived from it) or known matter forms part of the common general knowledge in the field of endeavour to which this specification relates.

The invention will now be described with reference to the following non-limiting examples. The following examples are representative of the general formula (I) and provide detailed methods for preparing exemplary compounds of the present invention.

Example 1. Synthesis of Acid-Triglycerides from Acid Anhydrides 4-((1,3-Bis(palmitoyloxy)propan-2-yl)oxy)-4-oxobutanoic acid (iii)

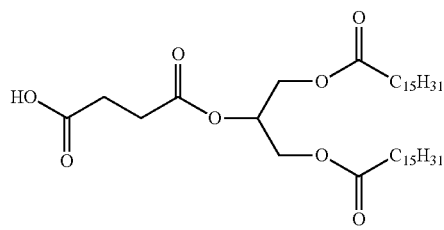

Succinic anhydride (iv) (25.4 mg, 0.254 mmol) and DMAP (15.5 mg, 0.127 mmol) were added to a solution of diglyceride ii (72.2 mg, 0.127 mmol) in pyridine (0.5 mL), $CH_2Cl_2$ (0.5 mL) and THF (0.5 mL) and the mixture stirred at rt for 17 hours. TLC analysis at this time showed the presence of unreacted diglyceride, so additional succinic anhydride (25.4 mg, 0.254 mmol) and DMAP (15.5 mg, 0.127 mmol) were added and the reaction heated at 40° C. for a further 22 hours. The mixture was cooled to rt, diluted with ethyl acetate (20 mL), washed with 1 M HCl (10 mL) and brine (2×30 mL), dried ($MgSO_4$) and concentrated under reduced pressure to give the crude product. Purification by silica gel chromatography (15% to 20% to 25% ethyl acetate/hexanes) gave acid-TG iii (77.0 mg, 91%) as a colourless solid.

$^1$H NMR (400 MHz, $CDCl_3$) δ 5.27 (m, 1H), 4.30 (dd, J=12.0, 4.3 Hz, 2H), 4.15 (dd, J=12.0, 5.8 Hz, 2H), 2.72-2.61 (m, 4H), 2.31 (t, J=7.6 Hz, 4H), 1.66-1.54 (m, 4H), 1.35-1.19 (m, 48H), 0.87 (t, J=6.9 Hz, 6H).

4-((1,3-Bis(palmitoyloxy)propan-2-yl)oxy)-3/2-methyl-4-oxobutanoic acid (iii)

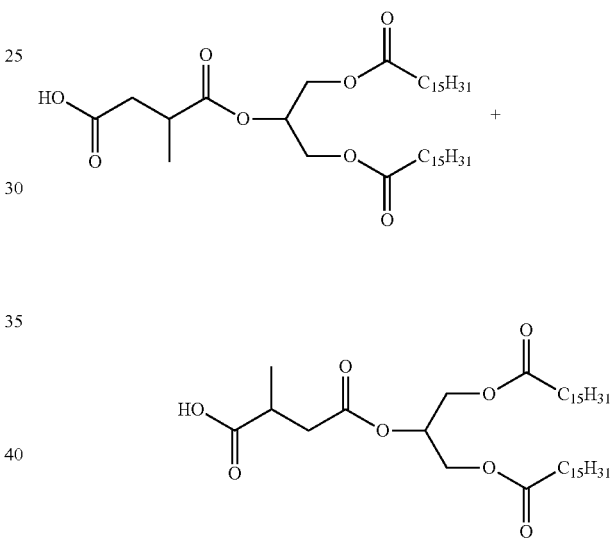

4-(Dimethylamino)pyridine (64.6 mg, 0.527 mmol) was added to a solution of diglyceride ii (200 mg, 0.351 mmol) and methylsuccinic anhydride (iv) (101 mg, 0.882 mmol) in pyridine/THF/$CH_2Cl_2$ (2.5 mL each) and the mixture stirred at rt for 22 hours. The reaction was diluted with ethyl acetate (40 mL), washed with 1 M HCl (30 mL) and brine (3×30 mL), dried ($MgSO_4$) and concentrated under reduced pressure to give crude acid-TG iii (~1:1 mixture of regioisomers, 240 mg, quant.) as a colourless solid that used in the next reaction without purification.

$^1$H NMR (400 MHz, $CDCl_3$) δ 5.31-5.24 (m, 1H), 4.34-4.27 (m, 2H), 4.21-4.10 (m, 2H), 3.00-2.90 (m, 1H), 2.82-2.72 (m, 1H), 2.52-2.43 (m, 1H), 2.37-2.28 (m, 4H), 1.67-1.55 (m, 4H), 1.46 (d, J=7.0 Hz, 3H), 1.36-1.17 (m, 48H), 0.88 (t, J=6.8 Hz, 6H). Note: integrations and multiplicities reflect the presence of a mixture of regioisomers.

Example 2. Synthesis of Acid-Triglycerides where $R^5$ is a Methyl Group a) 2-((4-((tert-Butyldiphenylsilyl)oxy)-2-methylbutanoyl)oxy)propane-1,3-diyl dipalmitate (vi)

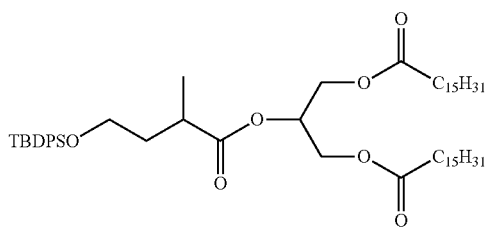

4-(Dimethylamino)pyridine (DMAP, 59.9 mg, 0.491 mmol) and EDC·HCl (235 mg, 1.23 mmol) were added to a solution of acid v (175 mg, 0.491 mmol) and 1,3-DG ii (293 mg, 0.515 mmol) in $CH_2Cl_2$ (8 mL) and the mixture stirred at rt for 16 hours. The reaction was diluted with $CH_2Cl_2$ (20 mL), silica gel was added and the mixture concentrated under reduced pressure. Purification by silica gel chromatography (3% to 10% ethyl acetate/hexanes) gave triglyceride vi (406 mg, 91%) as a colourless oil.

$^1$H NMR (400 MHz, $CDCl_3$) δ 7.67-7.63 (m, 4H), 7.45-7.34 (m, 6H), 5.25 (m, 1H), 4.30-4.22 (m, 2H), 4.15-4.08 (m, 2H), 3.69 (t, J=6.3 Hz, 2H), 2.75 (m, 1H), 2.27 (t, J=7.2 Hz, 2H), 2.25 (t, J=7.2 Hz, 2H), 1.99 (m, 1H), 1.64-1.55 (m, 5H), 1.32-1.20 (m, 48H), 1.14 (d, J=7.2 Hz, 3H), 1.04 (s, 9H), 0.88 (t, J=7.0 Hz, 6H).

b) 2-((4-Hydroxy-2-methylbutanoyl)oxy)propane-1,3-diyl dipalmitate (vii)

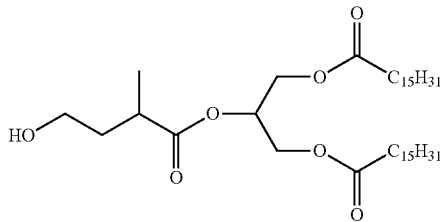

Tetrabutylammonium fluoride (TBAF, 1.0 M in THF, 810 µL, 0.810 µmol) and acetic acid (46.1 mL, 0.810 mmol) were added to a solution of TBDPS ether vi (406 mg, 0.447 mol) in THF (20 mL) at 0° C. and the mixture stirred at rt for three hours. The reaction was diluted with water (30 mL), extracted with ethyl acetate (3×20 mL), and the organic extracts washed with brine (30 mL), dried ($MgSO_4$) and concentrated under reduced pressure to give the crude product. Purification by silica gel chromatography (0% to 25% ethyl acetate/hexanes) gave alcohol vii (137 mg, 46%) as a colourless solid.

$^1$H NMR (400 MHz, $CDCl_3$) δ 5.27 (m, 1H), 4.39 (dd, J=12.0, 4.1 Hz, 1H), 4.32 (dd, J=11.9, 4.3 Hz, 1H), 4.16 (dd, J=12.0, 6.0 Hz, 1H), 4.12 (dd, J=12.0, 5.6 Hz, 1H), 3.74-3.63 (m, 2H), 2.66 (m, 1H), 2.316 (t, J=7.6 Hz, 2H), 2.309 (t, J=7.4 Hz, 2H), 1.91 (m, 1H), 1.70 (m, 1H), 1.63-1.58 (m, 4H), 1.34-1.25 (m, 48H), 1.19 (d, J=7.1 Hz, 3H), 0.88 (t, J=6.9 Hz, 6H).

c) 2-((2-Methyl-4-oxobutanoyl)oxy)propane-1,3-diyl dipalmitate (viii)

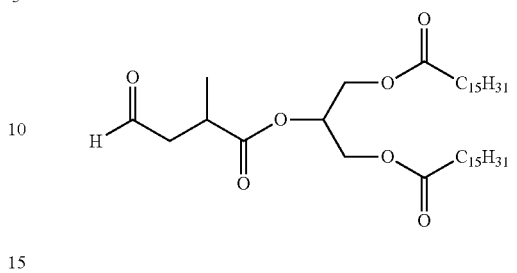

Pyridinium chlorochromate (PCC, 89.1 mg, 0.410 mmol) was added to a suspension of alcohol vii (137 mg, 0.205 mmol) and Celite (90 mg) in $CH_2Cl_2$ (12 mL) at 0° C. and the mixture stirred at rt for 2.5 hours. The reaction was filtered through a short pad of silica gel, eluting with 50% ethyl acetate/hexanes, and the filtrate concentrated under reduced pressure to give crude aldehyde viii (134 mg, quant.) as a yellow oil that was used without purification.

$^1$H NMR (400 MHz, $CDCl_3$) δ 9.75 (s, 1H), 5.27 (m, 1H), 4.30 (dd, J=12.0, 4.2 Hz, 2H), 4.16-4.09 (m, 2H), 2.99 (m, 1H), 2.89 (ddd, J=18.1, 7.8, 0.8 Hz, 1H), 2.55 (ddd, J=18.0, 5.5, 0.9 Hz, 1H), 2.32 (t, J=7.4 Hz, 2H), 2.30 (t, J=7.4 Hz, 2H), 1.64-1.58 (m, 4H), 1.33-1.25 (m, 48H), 1.22 (d, J=7.1 Hz, 3H), 0.88 (t, J=7.0 Hz, 6H).

d) 4-((1,3-Bis(palmitoyloxy)propan-2-yl)oxy)-3-methyl-4-oxobutanoic acid (iii)

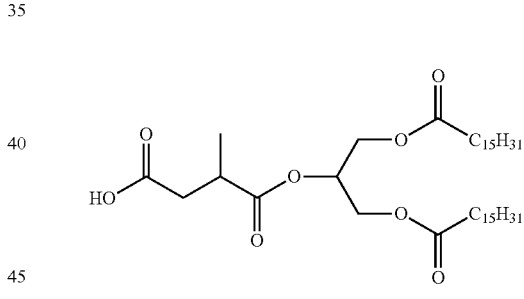

Potassium permanganate (65.4 mg, 0.410 µmol) was added to aldehyde viii (134 mg, 0.205 µmol) in acetone (7.5 mL) and water (2.5 mL) and the mixture stirred at rt for 19 hours. The reaction was diluted with water (25 mL), acidified to pH 2 using 1 M HCl, and the aqueous layer extracted with $CH_2Cl_2$ (3×20 mL). The combined organic extracts were washed with brine (30 mL), dried ($MgSO_4$) and concentrated under reduced pressure to give the crude product. Purification by silica gel chromatography (10% to 25% ethyl acetate/hexanes) gave acid iii (79.6 mg, 58%) as a colourless solid.

$^1$H NMR (400 MHz, $CDCl_3$) δ 5.27 (m, 1H), 4.32-4.27 (m, 2H), 4.18-4.12 (m, 2H), 2.92 (m, 1H), 2.78 (dd, J=16.9, 8.0 Hz, 1H), 2.46 (dd, J=16.9, 6.0 Hz, 1H), 2.304 (t, J=7.6 Hz, 2H), 2.297 (t, J=7.6 Hz, 2H), 1.62-1.56 (m, 4H), 1.31-1.19 (m, 51H), 0.88 (t, J=6.8 Hz, 6H).

Example 3. Synthesis of Compounds of the General Formula (III) Wherein $R^3$ is an Acetal Self-Immolative (ASI) Group 1,3-Bis(palmitoyloxy)propan-2-yl ((((8R,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl)oxy)methyl) succinate (12)

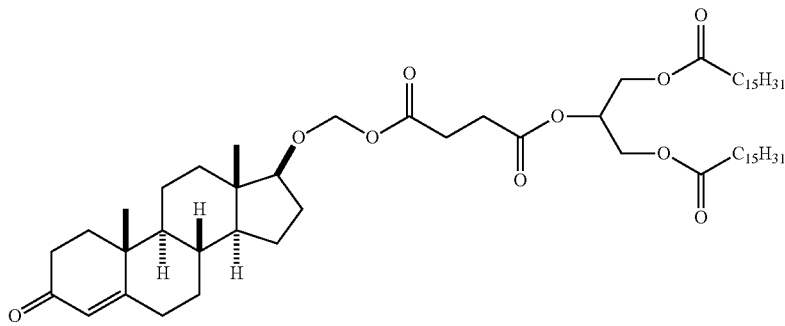

A solution of sulfuryl chloride (13.3 μL, 0.164 mmol) in $CH_2Cl_2$ (1 mL) was added to a solution of MTM ether ix (46.9 mg, 0.135 mmol) in $CH_2Cl_2$ (2 mL) at 0° C. and the mixture stirred at 0° C. for 30 minutes and then at rt for a further hour. The reaction was concentrated under a stream of $N_2$, co-evaporated from toluene (2×5 mL) and dried under reduced pressure. The crude residue was then re-dissolved in toluene (1.5 mL), added to a solution of acid iii (50.0 mg, 0.0747 mmol) and DBU (16.8 μL, 0.112 mmol) in toluene (1.5 mL) that had been pre-stirred for one hour, and the mixture stirred at rt for two hours. The reaction was diluted with $CH_2Cl_2$ (20 mL) and the organic phase washed with sat. aq. $NaHCO_3$ (20 mL) and brine (20 mL), dried ($MgSO_4$) and concentrated under reduced pressure to give the crude product. Purification by silica gel chromatography (10% to 25% ethyl acetate/hexanes with 0.5% $Et_3N$) gave Compound 12 (8.4 mg, 12%) as a pale yellow oil.

$^1$H NMR (400 MHz, $CDCl_3$) δ 5.73 (s, 1H), 5.34-5.23 (m, 3H), 4.30 (dd, J=11.9, 4.4 Hz, 2H), 4.15 (dd, J=11.9, 5.8 Hz, 2H), 3.54 (dd, J=8.3, 8.3 Hz, 1H), 2.65 (s, 4H), 2.48-2.24 (m, 8H), 2.09-1.99 (m, 2H), 1.92-1.80 (m, 2H), 1.74-1.36 (m, 9H), 1.35-1.21 (m, 49H), 1.19 (s, 3H), 1.17-0.91 (m, 5H), 0.88 (t, J=6.9 Hz, 6H), 0.80 (s, 3H).

ESI-HRMS: calcd. for $C_{59}H_{101}O_{10}$ [M+H$^+$] 969.7389; found 969.7409.

1-(1,3-Bis(palmitoyloxy)propan-2-yl) 4-((((8R,9S,10R,13S,14S,17S)-10,13-dimethyl-3-oxo-2,3,6,7,8,9,10,11,12,13,14,15,16,17-tetradecahydro-1H-cyclopenta[a]phen-anthren-17-yl)oxy)methyl) 2/3-methylsuccinate (13/14)

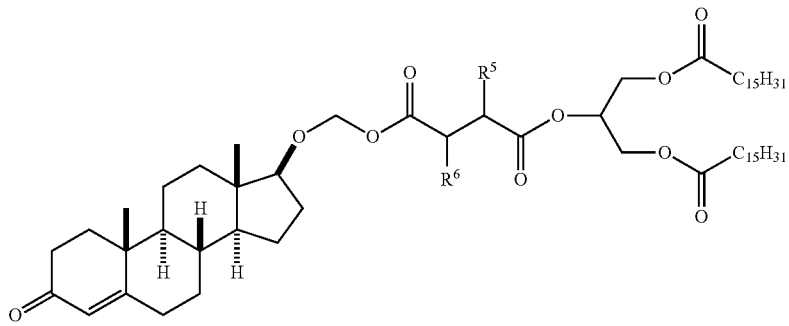

misture of $R^5$ = Me, $R^6$ = H
and $R^5$ = H, $R^6$ = Me

A solution of sulfuryl chloride (21.4 μL, 0.264 mmol) in $CH_2Cl_2$ (1.5 mL) was added to a solution of MTM ether ix (76.3 mg, 0.219 mmol) in $CH_2Cl_2$ (3 mL) at 0° C. and stirred at 0° C. for 30 minutes and then at rt for a further 45 minutes. The reaction was concentrated under a stream of $N_2$, co-evaporated from toluene (2×5 mL) and dried under reduced pressure. This crude residue was then re-dissolved in toluene (2.5 mL), added to a solution of acid iii (99.4 mg, 0.146 mmol) and DBU (32.8 μL, 0.220 mmol) in toluene (2.5 mL) that had been pre-stirred for 45 minutes, and the mixture stirred at rt for three hours. The reaction was diluted with ethyl acetate (20 mL) and the organic phase washed with sat. aq. $NaHCO_3$ (2×20 mL) and brine (2×20 mL), dried ($MgSO_4$) and concentrated under reduced pressure to give the crude product. Purification by silica gel chromatography (5% to 15% ethyl acetate/hexanes with 0.5% $Et_3N$) gave Compounds 13 and 14 (1:1 mixture of regioisomers, 74.2 mg, 52%) as a pale yellow oil.

$^1$H NMR (400 MHz, CDCl$_3$) δ 5.73 (s, 1H), 5.38-5.21 (m, 3H), 4.32-4.25 (m, 2H), 4.20-4.10 (m, 2H), 3.58-3.50 (m, 1H), 2.98-2.87 (m, 1H), 2.81-2.71 (m, 1H), 2.47-2.24 (m, 9H), 2.08-1.98 (m, 2H), 1.92-1.80 (m, 2H), 1.75-1.51 (m, 8H), 1.50-1.20 (m, 53H), 1.19 (s, 3H), 1.17-0.89 (m, 5H), 0.88 (t, J=7.0 Hz, 6H), 0.80 (s, 1.5H), 0.79 (s, 1.5H). Note: integrations and multiplicities reflect the presence of a 1:1 mixture of regioisomers, in addition to possible diastereoisomers.

1-(1,3-Bis(palmitoyloxy)propan-2-yl) 4-((((8R,9S,10R,13S,14S,17S)-10,13-dimethyl-3-oxo-2,3,6,7,8,9,10,11,12,13,14,15,16,17-tetradecahydro-1H-cyclopenta[a]phen-anthren-17-yl)oxy)methyl) 2-methylsuccinate (13)

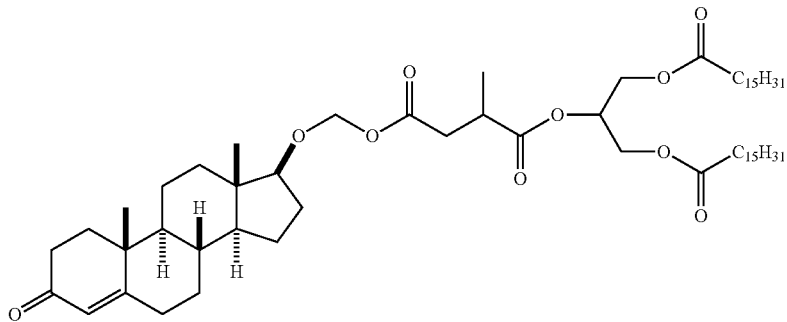

Prepared as above from the α-Methyl regioisomer of acid-TG iii.

$^1$H NMR (400 MHz, CDCl$_3$) δ 5.72 (s, 1H), 5.32-5.22 (m, 3H), 4.29/4.27 (each dd, J=12.0, 4.2 Hz, 2H), 4.17/4.14 (each dd, J=11.9, 6.0 Hz, 2H), 3.529/3.524 (each t, J=8.3 Hz, 1H), 2.93 (m, 1H), 2.75 (dd, J=16.8, 7.9 Hz, 1H), 2.49-2.23 (m, 9H), 2.08-1.96 (m, 2H), 1.91-1.79 (m, 2H), 1.71 (m, 1H), 1.67-1.51 (m, 8H), 1.49-1.07 (m, 51H), 1.22 (d, J=7.2 Hz, 3H), 1.18 (s, 3H), 1.06-0.90 (m, 3H), 0.87 (t, J=6.8 Hz, 6H), 0.79 (s, 3H). Note: doubled signals (eg: 4.29/4.27) reflect the presence of a mixture of diastereoisomers.

ESI-HRMS: calcd. for C$_{60}$H$_{102}$O$_{10}$Na [M+Na$^+$] 1005.7365; found 1005.7370.

Example 4. Synthesis of Compounds of the General Formula (III) Wherein R$^3$ is a Carboxy-Acetal or Carboxy-Methylacetal Self-Immolative (CASI or CMSI) Group a) Chloromethyl ((1S,4S)-4-(3,4-dichlorophenyl)-1,2,3,4-tetrahydronaphthalen-1-yl)(methyl)carbamate (xi)

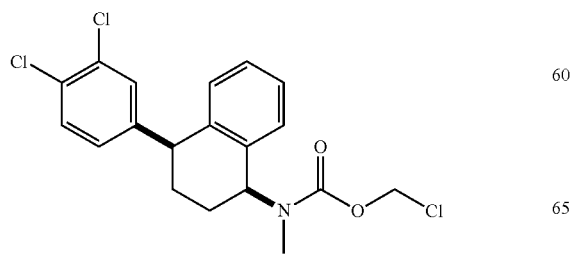

Chloromethyl chloroformate (25.9 μL, 0.292 mmol) and pyridine (41.3 μL, 0.511 mmol) were added to sertraline hydrochloride (50.0 mg, 0.146 mmol) in CH$_2$Cl$_2$ (4 mL) at 0° C. and the mixture stirred at 0° C. for 15 minutes and then at rt for one hour. The reaction was diluted with CH$_2$Cl$_2$ (20 mL) and the organic phase washed with sat. aq. NaHCO$_3$ (20 mL) and brine (20 mL), dried (MgSO$_4$) and concentrated under reduced pressure to give chloromethyl carbamate xi (58.2 mg, quant.) as a pale yellow oil that was used without purification.

$^1$H NMR (400 MHz, CDCl$_3$) δ 7.34 (d, J=8.3 Hz, 1H), 7.31-7.25 (m, 1H), 7.24-7.16 (m, 1H), 7.11-7.06 (m, 1H), 6.97 (dd, J=7.0, 2.0 Hz, 1H), 6.84-6.79 (m, 1H), 5.91-5.83 (m, 1H), 5.51 (dd, J=10.4, 6.5 Hz, 0.6H), 5.32 (dd, J=14.5, 6.1 Hz, 0.4H), 4.20 (dd, J=5.2, 2.9 Hz, 1H), 2.78 (s, 1.2H), 2.72 (s, 1.8H), 2.36-2.22 (m, 1H), 2.07-1.99 (m, 1H), 1.87-1.70 (m, 2H). Note: fractional integrations reflect the presence of a mixture of rotational isomers.

b) 1,3-Bis(palmitoyloxy)propan-2-yl (((((1S,4S)-4-(3,4-dichlorophenyl)-1,2,3,4-tetrahydronaphthalen-1-yl)(methyl)carbamoyl)oxy)methyl) succinate (1)

a2) 1-Chloroethyl ((1S,4S)-4-(3,4-dichlorophenyl)-1,2,3,4-tetrahydronaphthalen-1-yl)(methyl)carbamate (xi)

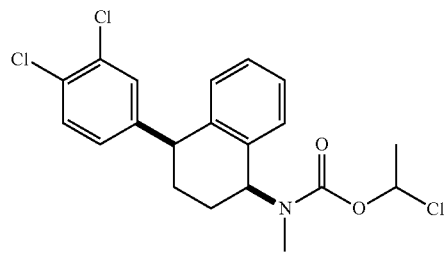

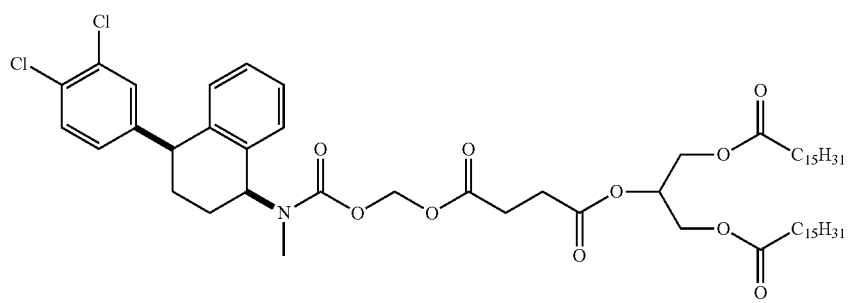

1,8-Diazabicyclo[5.4.0]undec-7-ene (DBU) (7.8 μL, 52.2 μmol) was added to a suspension of acid-TG iii (25.1 mg, 37.5 μmol), chloromethyl carbamate xi (13.0 mg, 32.6 mol) and tetrabutylammonium iodide (TBAI, 3.6 mg, 9.8 μmol) in toluene (1.2 mL) and the mixture heated at reflux for one hour. The reaction was cooled to rt, diluted with ethyl acetate (20 mL) and the organic phase washed with water and brine (20 mL each), dried (MgSO$_4$) and concentrated under reduced pressure to give the crude product. Silica gel chromatography (15% ethyl acetate/hexane) gave Compound 1 (29.0 mg, 86%) as a colourless oil.

$^1$H NMR (400 MHz, CDCl$_3$) δ 7.33 (d, J=8.3 Hz, 1H), 7.30-7.24 (m, 1H), 7.22-7.17 (m, 2H), 7.09 (d, J=2.0 Hz, 1H), 6.96 (d, J=7.3 Hz, 1H), 6.84-6.78 (m, 1H), 5.89-5.83 (m, 2H), 5.49 (dd, J=10.1, 6.6 Hz, 0.6H), 5.36-5.20 (m, 1.4H), 4.33-4.25 (m, 2H), 4.21-4.10 (m, 3H), 2.78-2.61 (m, 7H), 2.38-2.23 (m, 5H), 2.06-1.96 (m, 1H), 1.87-1.69 (m, 2H), 1.67-1.53 (m, 4H), 1.38-1.19 (m, 48H), 0.88 (t, J=6.9 Hz, 6H). Note: fractional integrations reflect the presence of a mixture of rotational isomers.

ESI-HRMS: calcd. for C$_{58}$H$_{89}$Cl$_2$NO$_{10}$Na [M+Na$^+$] 1052.5756; found 1052.5774.

1-Chloroethyl chloroformate (25.2 μL, 0.233 mmol) and pyridine (35.4 μL, 0.438 mmol) were added to sertraline hydrochloride (50.0 mg, 0.146 mmol) in CH$_2$Cl$_2$ (5 mL) at 0° C. and the mixture stirred at 0° C. for 30 minutes and then at rt for 19 hours. The reaction was diluted with CH$_2$Cl$_2$ (25 mL) and the organic phase washed with sat. aq. NaHCO$_3$ (20 mL) and brine (20 mL), dried (MgSO$_4$) and concentrated under reduced pressure to give the crude product. Purification by silica gel chromatography (15% ethyl acetate/hexanes with 0.5% Et$_3$N) gave chloroethyl carbamate xi (50.4 mg, 84%) as a colourless solid.

$^1$H NMR (400 MHz, CDCl$_3$) δ 7.34 (d, J=8.3 Hz, 1H), 7.31-7.24 (m, 1H), 7.24-7.16 (m, 2H), 7.13-7.04 (m, 1H), 7.00-6.94 (m, 1H), 6.85-6.77 (m, 1H), 6.75-6.64 (m, 1H), 5.54-5.46 (m, 0.6H), 5.41-5.33 (m, 0.4H), 4.20 (br s, 1H), 2.74/2.71/2.70 (each s, 3H), 2.36-2.24 (m, 1H), 2.09-1.97 (m, 1H), 1.90-1.71 (m, 5H). Note: fractional integrations and doubled signals reflect the presence of both rotational isomers and diastereoisomers.

b2) 1,3-Bis(palmitoyloxy)propan-2-yl (1-((((1S,4S)-4-(3,4-dichlorophenyl)-1,2,3,4-tetrahydronaphthalen-1-yl)(methyl)carbamoyl)oxy)ethyl) succinate (2)

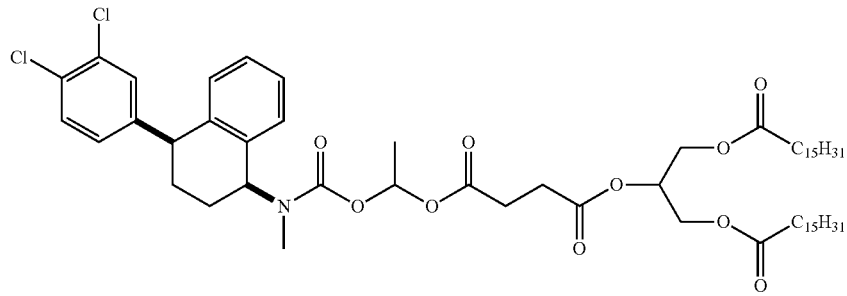

1,8-Diazabicyclo[5.4.0]undec-7-ene (DBU) (7.8 μL, 52.0 μmol) was added to a suspension of acid-TG iii (25.0 mg, 37.4 μmol), 1-chloroethyl carbamate xi (13.4 mg, 32.5 μmol) and tetrabutylammonium iodide (TBAI, 3.6 mg, 9.7 μmol) in toluene (1.2 mL) and the mixture heated at reflux for one hour. The reaction was cooled to rt, diluted with ethyl acetate (30 mL) and the organic phase washed with water and brine (20 mL each), dried (MgSO$_4$) and concentrated under reduced pressure to give the crude product. Silica gel chromatography (4% to 8% ethyl acetate/toluene) gave Compound 2 (19.7 mg, 58%) as a colourless oil.

$^1$H NMR (400 MHz, CDCl$_3$) δ 7.33 (d, J=8.3 Hz, 1H), 7.31-7.16 (m, 3H), 7.12-7.06 (m, 1H), 6.98-6.87 (m, 2H), 6.85-6.77 (m, 1H), 5.51-5.43 (m, 0.6H), 5.36-5.16 (m, 1.4H), 4.35-4.24 (m, 2H), 4.21-4.11 (m, 3H), 2.77-2.56 (m, 7H), 2.37-2.24 (m, 5H), 2.06-1.95 (m, 1H), 1.85-1.71 (m, 2H), 1.65-1.49 (m, 7H), 1.37-1.19 (m, 48H), 0.88 (t, J=6.8 Hz, 6H). Note: fractional integrations reflect the presence of both rotational isomers and diastereoisomers.

ESI-HRMS: calcd. for C$_{59}$H$_{91}$Cl$_2$NO$_{10}$Na [M+Na$^+$] 1066.5912; found 1066.5957.

The following carboxy-acetal or carboxy-methylacetal self-immolative containing compounds were prepared according to the above methods:

a3) Chloromethyl ((4aS,6R,7R,7aR,12bS)-3-(cyclopropylmethyl)-6-((S)-2-hydroxy-3,3-dimethylbutan-2-yl)-7-methoxy-1,2,3,4,5,6,7,7a-octahydro-4a,7-ethano-4,12-methanobenzofuro[3,2-e]isoquinolin-9-yl) carbonate (xi)

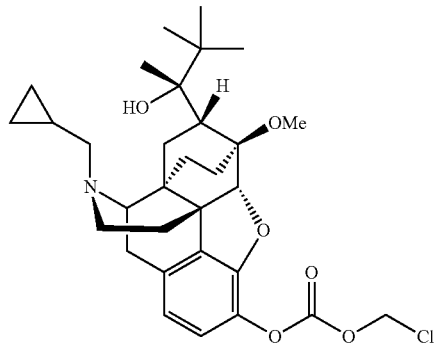

$^1$H NMR (400 MHz, CDCl$_3$): δ 6.88 (d, J=8.2 Hz, 1H), 6.61 (d, J=8.2 Hz, 1H), 5.88 (s, 1H), 5.82 (d, J=6.3 Hz, 1H), 5.72 (d, J=6.3 Hz, 1H), 4.47 (d, J=1.7 Hz, 1H), 3.48 (s, 3H), 3.06-2.98 (m, 2H), 2.89 (m, 1H), 2.63 (dd, J=11.9, 5.0 Hz, 1H), 2.40-2.23 (m, 4H), 2.12 (t, J=9.9 Hz, 1H), 2.03-1.79 (m, 3H), 1.71 (dd, J=12.9, 2.5 Hz, 1H), 1.35 (s, 3H), 1.28 (m, 2H), 1.06 (m, 1H), 1.03 (s, 9H), 0.81 (m, 1H), 0.66 (m, 1H), 0.57-0.41 (m, 2H), 0.16-0.08 (m, 2H).

b3) 1,3-Bis(palmitoyloxy)propan-2-yl ((((((4aS,6R,7R,7aR,12bS)-3-(cyclopropylmethyl)-6-((S)-2-hydroxy-3,3-dimethylbutan-2-yl)-7-methoxy-1,2,3,4,5,6,7,7a-octahydro-4a,7-ethano-4,12-methanobenzofuro[3,2-e]isoquinolin-9-yl)oxy)carbonyl)oxy)methyl) succinate (4)

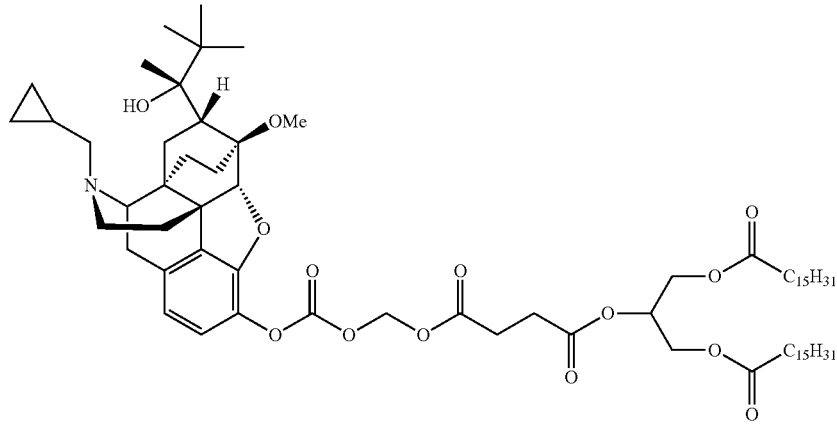

Compound 4 was prepared using an alternative method to that used above for compounds 1 and 2, described as follows. Silver carbonate (3.1 mg, 11.2 μmol) was added to acid-TG iii (12.9 mg, 19.3 μmol) in DMF (0.6 mL) and the mixture stirred at rt for one hour. The reaction was concentrated under reduced pressure to give a grey residue, to which was added chloromethyl carbonate xi (9.0 mg, 16.1 μmol) in toluene (0.6 mL) and TBAI (1.8 mg, 4.8 μmol) and the mixture heated at reflux for 1.5 hours. The reaction was cooled to rt, then diluted with ethyl acetate (30 mL). The organic phase was washed with water (25 mL) and brine (25 mL), dried (MgSO$_4$) and concentrated under reduced pressure to give the crude product. Silica gel chromatography (5% to 15% ethyl acetate/hexanes) gave Compound 4 (3.7 mg, 19%) as a colourless solid.

$^1$H NMR (400 MHz, CDCl$_3$) δ 6.88 (d, J=8.2 Hz, 1H), 6.60 (d, J=8.1 Hz, 1H), 5.86 (s, 1H), 5.82 (s, 2H), 5.27 (m, 1H), 4.46 (s, 1H), 4.30 (dd, J=12.0, 4.3 Hz, 2H), 4.15 (dd, J=12.0, 5.9 Hz, 2H), 3.49 (s, 3H), 3.06-2.98 (m, 2H), 2.89 (m, 1H), 2.73-2.60 (m, 5H), 2.39-2.22 (m, 8H), 2.12 (t, J=9.2 Hz, 1H), 2.01 (m, 1H), 1.93-1.80 (m, 2H), 1.75-1.49 (m, 5H), 1.35 (s, 3H), 1.34-1.20 (m, 49H), 1.05 (m, 1H), 1.03 (s, 9H), 0.88 (t, J=6.9 Hz, 6H), 0.80 (m, 1H), 0.66 (m, 1H), 0.56-0.44 (m, 2H), 0.16-0.09 (m, 2H).

ESI-HRMS: calcd. for C$_{70}$H$_{114}$NO$_{14}$[M+H$^+$] 1192.8234; found 1192.8244.

1,3-Bis(palmitoyloxy)propan-2-yl (1-(((((4aS,6R,7R,7aR,12bS)-3-(cyclopropylmethyl)-6-((S)-2-hydroxy-3,3-dimethylbutan-2-yl)-7-methoxy-1,2,3,4,5,6,7,7a-octahydro-4a,7-ethano-4,12-methanobenzofuro[3,2-e]isoquinolin-9-yl)oxy)carbonyl)oxy)ethyl) succinate (5)

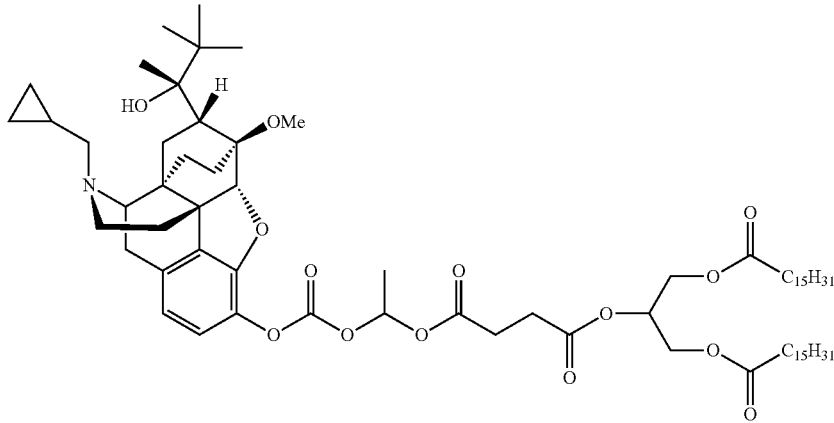

$^1$H NMR (400 MHz, CDCl$_3$) δ 6.88/6.87 (each d, J=8.2 Hz, 1H), 6.77 (m, 1H), 6.59 (d, J=8.2 Hz, 1H), 5.89/5.88 (each s, 1H), 5.25 (m, 1H), 4.46 (br s, 1H), 4.33-4.26 (m, 2H), 4.19-4.11 (m, 2H), 3.49/3.48 (each s, 3H), 3.06-2.98 (m, 2H), 2.89 (m, 1H), 2.74-2.57 (m, 5H), 2.38-2.20 (m, 8H), 2.12 (t, J=10.0 Hz, 1H), 1.98 (td, J=12.5, 5.5 Hz, 1H), 1.91-1.77 (m, 2H), 1.70 (dd, J=13.4, 2.9 Hz, 1H), 1.64-1.52 (m, 7H), 1.35 (s, 3H), 1.33-1.18 (m, 49H), 1.06 (m, 1H), 1.03 (s, 5H), 0.88 (t, J=6.9 Hz, 6H), 0.81 (m, 1H), 0.66 (m, 1H), 0.55-0.43 (m, 2H), 0.15-0.07 (m, 2H). Note: doubled signals reflect the presence of a mixture of diastereoisomers.

ESI-HRMS: calcd. for C$_{7t}$H$_{116}$NO$_{14}$ [M+H$^+$] 1206.8390; found 1206.8401.

1,3-Bis(palmitoyloxy)propan-2-yl (1-(((((8R,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl)oxy)carbonyl)oxy)ethyl) succinate (20)

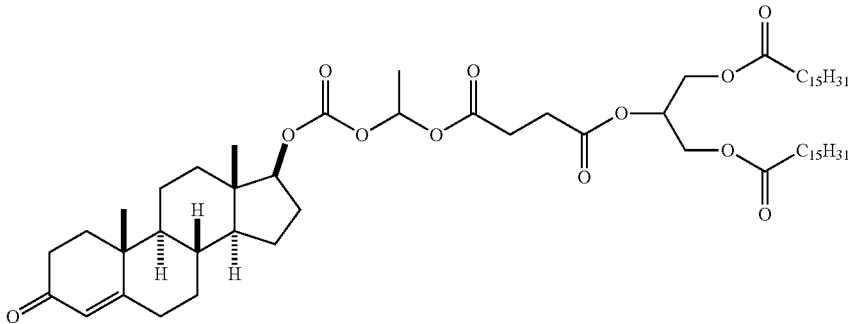

¹H NMR (400 MHz, CDCl₃) δ 6.75 (m, 1H), 5.73 (s, 1H), 5.25 (m, 1H), 4.53 (m, 1H), 4.34-4.26 (m, 2H), 4.18-4.11 (m, 2H), 2.73-2.58 (m, 4H), 2.48-2.15 (m, 9H), 2.02 (m, 1H), 1.91-1.82 (m, 2H), 1.78-1.55 (m, 8H), 1.521 (d, J=5.4 Hz, 1.5H), 1.517 (d, J=5.4 Hz, 1.5H), 1.47-1.20 (m, 52H), 1.19 (s, 3H), 1.11-0.90 (m, 3H), 0.88 (t, J=7.5 Hz, 6H), 0.86 (s, 3H). Note: doubled signals reflect the presence of a mixture of diastereoisomers.

ESI-HRMS: calcd. for C₆₁H₁₀₂O₁₂Na [M+Na⁺] 1049.7263; found 1049.7273.

Example 5. Synthesis of Compounds of the General Formula (III) Wherein R³ is a Trimethyl-Lock (TML) Self-Immolative Group a) 1,3-Bis(palmitoyloxy)propan-2-yl (2-(4-((tert-butyldimethylsilyl)oxy)-2-methylbutan-2-yl)-3,5-dimethylphenyl) succinate (xiv)

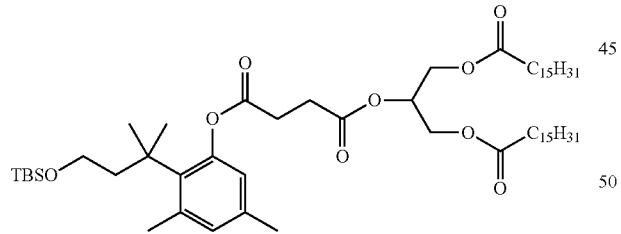

4-(Dimethylamino)pyridine (DMAP, 18.3 mg, 0.149 mmol) and EDC·HCl (71.6 mg, 0.374 mmol) were added to a solution of acid-TG iii (100 mg, 0.149 mmol) and phenol xiii (53.0 mg, 0.164 mmol) in CH₂Cl₂ (4 mL) and the mixture stirred at rt for 19 hours. The reaction was diluted with CH₂Cl₂ (10 mL), silica gel was added and the mixture concentrated under reduced pressure. Purification by silica gel chromatography (3% to 7.5% ethyl acetate/hexanes) gave TML triglyceride xiv (84.6 mg, 58%) as a colourless oil.

¹H NMR (400 MHz, CDCl₃) δ 6.80 (d, J=2.0 Hz, 1H), 6.55 (d, J=1.9 Hz, 1H), 5.29 (m, 1H), 4.31 (dd, J=11.9, 4.4 Hz, 2H), 4.16 (dd, J=12.0, 5.8 Hz, 2H), 3.51-3.44 (m, 2H), 2.85 (t, J=6.9 Hz, 2H), 2.75 (t, J=6.9 Hz, 2H), 2.51 (s, 3H), 2.30 (t, J=7.6 Hz, 4H), 2.22 (s, 3H), 2.06-1.99 (m, 2H), 1.65-1.56 (m, 4H), 1.46 (s, 6H), 1.37-1.20 (m, 48H), 0.88 (t, J=6.9 Hz, 6H), 0.84 (s, 9H), −0.03 (s, 6H).

b) 1,3-Bis(palmitoyloxy)propan-2-yl (2-(4-hydroxy-2-methylbutan-2-yl)-3,5-dimethylphenyl) succinate (xv)

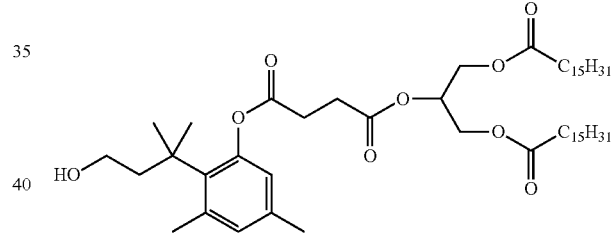

10-Camphorsulfonic acid (3.0 mg, 12.9 μmol) was added to TBS ether xiv (83.7 mg, 86.0 mmol) in CH₂Cl₂ (1 mL) and MeOH (1 mL) and the mixture stirred at rt for one hour. The reaction was diluted with water (10 mL) and the aqueous layer extracted with CH₂Cl₂ (3×10 mL). The combined organic extracts were washed with sat. aq. NaHCO₃ and brine (15 mL each), dried (MgSO₄) and concentrated under reduced pressure to give the crude product. Purification by silica gel chromatography (15% to 25% ethyl acetate/hexanes) gave alcohol xv (59.9 mg, 81%) as a colourless oil.

¹H NMR (400 MHz, CDCl₃) δ 6.81 (d, J=2.0 Hz, 1H), 6.56 (d, J=1.4 Hz, 1H), 5.28 (m, 1H), 4.30 (dd, J=12.0, 4.4 Hz, 2H), 4.17 (dd, J=12.0, 5.8 Hz, 2H), 3.51 (t, J=6.8 Hz, 2H), 2.88 (t, J=6.6 Hz, 2H), 2.75 (t, J=6.6 Hz, 2H), 2.52 (s, 3H), 2.29 (t, J=7.6 Hz, 4H), 2.22 (s, 3H), 2.05 (t, J=7.4 Hz, 2H), 1.65-1.57 (m, 4H), 1.50 (s, 6H), 1.37-1.20 (m, 48H), 0.88 (t, J=6.9 Hz, 6H).

c) 1,3-Bis(palmitoyloxy)propan-2-yl (3,5-dimethyl-2-(2-methyl-4-oxobutan-2-yl)phenyl) succinate (xvi)

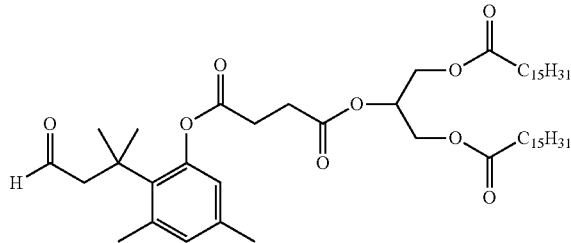

Pyridinium chlorochromate (PCC, 30.1 mg, 0.139 mmol) was added to a suspension of alcohol xv (59.9 mg, 0.0697 mmol) and Celite (30 mg) in $CH_2Cl_2$ (3 mL) at 0° C. and the mixture stirred at rt for two hours. The reaction was filtered through a short pad of silica gel, eluting with 50% ethyl acetate/hexanes, and the filtrate concentrated under reduced pressure to give crude aldehyde xvi (59.8 mg, quant.) as a yellow oil that was used without purification.

$^1$H NMR (400 MHz, $CDCl_3$) δ 9.54 (t, J=2.6 Hz, 1H), 6.84 (d, J=2.0 Hz, 1H), 6.60 (d, J=1.4 Hz, 1H), 5.28 (m, 1H), 4.30 (dd, J=12.0, 4.3 Hz, 2H), 4.16 (dd, J=12.0, 5.8 Hz, 2H), 2.86 (t, J=6.7 Hz, 2H), 2.83 (d, J=2.6 Hz, 2H), 2.75 (t, J=6.3 Hz, 2H), 2.53 (s, 3H), 2.30 (t, J=7.6 Hz, 4H), 2.23 (s, 3H), 1.64-1.58 (m, 4H), 1.56 (s, 3H), 1.55 (s, 3H), 1.32-1.22 (m, 48H), 0.88 (t, J=6.9 Hz, 6H).

d) 1,3-(2-((4-((1,3-bis(palmitoyloxy)propan-2-yl)oxy)-4-oxobutanoyl)oxy)-4,6-dimethylphenyl)-3-methylbutanoic acid (xvii)

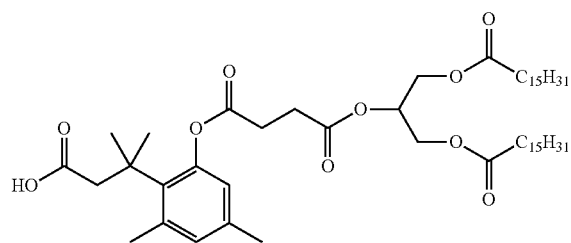

Potassium permanganate (12.2 mg, 76.7 µmol) was added to aldehyde xvi (59.8 mg, 69.7 mol) in acetone (2.4 mL) and water (0.8 mL) and the mixture stirred at rt for 17 hours. The reaction was diluted with water (10 mL), acidified to pH 2 using 1 M HCl, and the aqueous layer extracted with $CH_2Cl_2$ (3×15 mL). The combined organic extracts were washed with brine (30 mL), dried ($MgSO_4$) and concentrated under reduced pressure to give the crude product. Purification by silica gel chromatography (10% to 25% ethyl acetate/hexanes) gave acid xvii (30.4 mg, 50%) as a colourless solid.

$^1$H NMR (400 MHz, $CDCl_3$) δ 6.81 (d, J=1.6 Hz, 1H), 6.58 (d, J=1.4 Hz, 1H), 5.28 (m, 1H), 4.30 (dd, J=11.9, 4.4 Hz, 2H), 4.16 (dd, J=12.0, 5.8 Hz, 2H), 2.88 (t, J=6.6 Hz, 2H), 2.84 (s, 2H), 2.75 (t, J=6.6 Hz, 2H), 2.53 (s, 3H), 2.29 (t, J=7.6 Hz, 4H), 2.22 (s, 3H), 1.64-1.58 (m, 4H), 1.57 (s, 6H), 1.34-1.20 (m, 48H), 0.88 (t, J=6.8 Hz, 6H).

e) 1,3-Bis(palmitoyloxy)propan-2-yl (2-(4-(((8R,9S,10R,13S,14S,17S)-10,13-dimethyl-3-oxo-2,3,6,7,8,9,10,11,12,13,14,15,16,17-tetradecahydro-1H-cyclopenta[a]phenan-thren-17-yl)oxy)-2-methyl-4-oxobutan-2-yl)-3,5-dimethylphenyl) succinate (15)

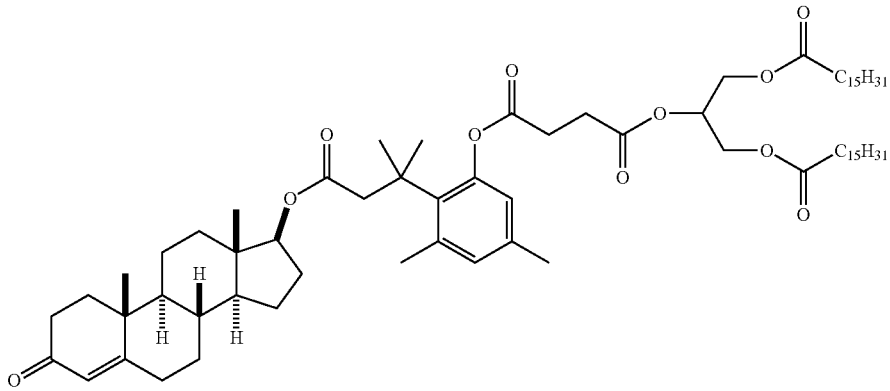

4-(Dimethylamino)pyridine (DMAP, 4.1 mg, 33.2 µmol), EDC·HCl (16.0 mg, 83.0 µmol) and testosterone (17.2 mg, 60.0 µmol) were added to a solution of acid xvii (29.0 mg, 33.2 µmol) in $CH_2Cl_2$ (1.2 mL) and the mixture stirred at rt for 19 hours. The reaction was diluted with $CH_2Cl_2$ (5 mL), silica gel was added and the mixture concentrated under reduced pressure. Purification by silica gel chromatography (12.5% to 20% ethyl acetate/hexanes) gave Compound 15 (15.0 mg, 40%) as a colourless solid.

$^1$H NMR (400 MHz, $CDCl_3$) δ 6.80 (d, J=2.0 Hz, 1H), 6.57 (d, J=1.9 Hz, 1H), 5.72 (s, 1H), 5.28 (m, 1H), 4.46 (dd, J=9.1, 7.3 Hz, 1H), 4.31 (dd, J=11.9, 4.4 Hz, 2H), 4.16 (dd, J=11.9, 5.8 Hz, 2H), 2.88 (t, J=6.7 Hz, 2H), 2.81 (d, J=11.4 Hz, 2H), 2.76 (t, J=6.9 Hz, 2H), 2.54 (s, 3H), 2.50-2.23 (m, 8H), 2.21 (s, 3H), 2.14-1.96 (m, 2H), 1.81 (m, 1H), 1.69 (m, 1H), 1.65-1.47 (m, 14H), 1.40-1.20 (m, 51H), 1.17 (s, 3H), 1.10-0.92 (m, 4H), 0.88 (t, J=6.9 Hz, 6H), 0.66 (s, 3H).

ESI-HRMS: calcd. for $C_{71}H_{115}O_{11}$ [M+H$^+$] 1143.8434; found 1143.8443.

The following trimethyl-lock self-immolative group containing compounds were prepared according to the above methods:

1,3-Bis(palmitoyloxy)propan-2-yl (2-(4-(((1S,4S)-4-(3,4-dichlorophenyl)-1,2,3,4-tetrahydronaphthalen-1-yl)(methyl)amino)-2-methyl-4-oxobutan-2-yl)-3,5-dimethylphenyl) succinate (3)

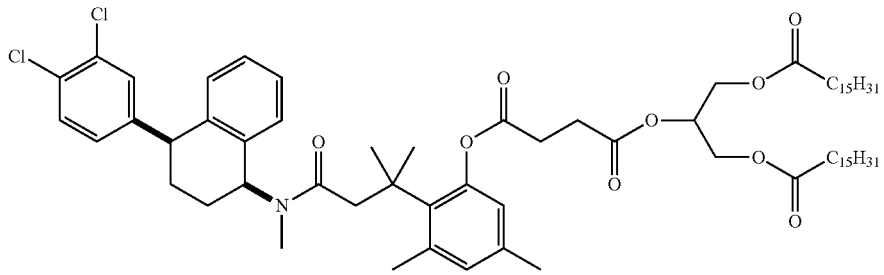

4-(Dimethylamino)pyridine (DMAP, 2.8 mg, 22.9 μmol), EDC·HCl (11.0 mg, 57.3 μmol) and triethylamine (8.0 μL, 57.3 μmol) were added to a solution of sertraline hydrochloride (10.2 mg, 29.8 μmol) and acid xvii (20.0 mg, 22.9 μmol) in CH$_2$Cl$_2$ (1 mL) and the mixture stirred at rt for 16 hours. The reaction was diluted with CH$_2$Cl$_2$ (5 mL), silica gel was added and the mixture concentrated under reduced pressure. Purification by silica gel chromatography (15% to 25% ethyl acetate/hexanes) gave Compound 3 (22.2 mg, 83%) as a colourless solid.

$^1$H NMR (400 MHz, CDCl$_3$) δ 7.32 (d, J=8.3 Hz, 0.7H), 7.31 (d, J=8.3 Hz, 0.3H), 7.25-7.11 (m, 2H), 7.08-7.02 (m, 1.3H), 6.97-6.85 (m, 1.7H), 6.83-6.79 (m, 1.7H), 6.73 (dd, J=8.3, 2.0 Hz, 0.3H), 6.60 (d, J=1.8 Hz, 0.7H), 6.57 (d, J=1.7 Hz, 0.3H), 5.88 (dd, J=10.5, 6.3 Hz, 0.7H), 5.24 (m, 1H), 4.96 (dd, J=10.9, 5.7 Hz, 0.3H), 4.32-4.25 (m, 2H), 4.20-4.10 (m, 3H), 3.09 (d, J=15.5 Hz, 0.7H), 3.01 (d, J=8.2 Hz, 0.3H), 2.92-2.73 (m, 4.3H), 2.70-2.64 (m, 3H), 2.60-2.56 (m, 3.7H), 2.29 (t, J=7.5 Hz, 4H), 2.23 (s, 2.1H), 2.21 (s, 0.9H), 2.21 (m, 1H), 1.95 (m, 1H), 1.69 (s, 2.1H), 1.66 (s, 0.9H), 1.62 (s, 3H), 1.70-1.52 (m, 6H), 1.34-1.20 (m, 48H), 0.88 (t, J=6.9 Hz, 6H). Note: fractional integrations reflect the presence of a mixture of rotational isomers.

ESI-HRMS: calcd. for C$_{69}$H$_{103}$Cl$_2$NO$_9$Na [M+Na$^+$] 1182.6902; found 1182.6904.

1,3-Bis(palmitoyloxy)propan-2-yl (2-(4-(((4aS,6R,7R,7aR,12bS)-3-(cyclopropylmethyl)-6-((S)-2-hydroxy-3,3-dimethylbutan-2-yl)-7-methoxy-1,2,3,4,5,6,7,7a-octahydro-4a,7-ethano-4,12-methanobenzofuro[3,2-e]isoquinolin-9-yl)oxy)-2-methyl-4-oxobutan-2-yl)-3,5-dimethylphenyl) succinate (6)

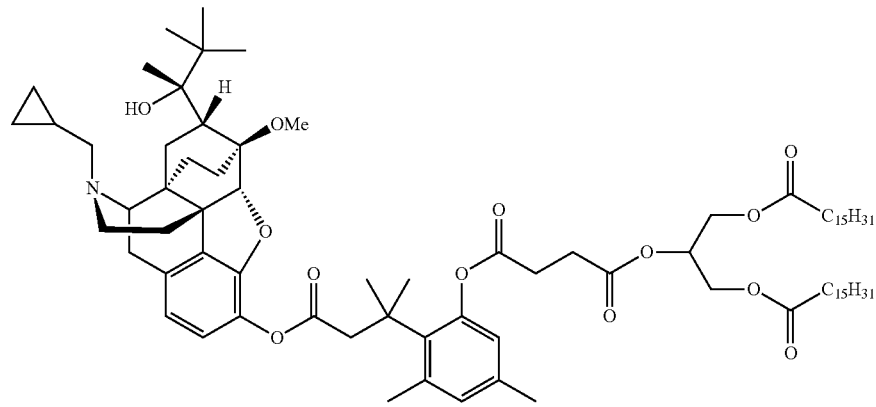

$^1$H NMR (400 MHz, CDCl$_3$) δ 6.80 (d, J=1.9 Hz, 1H), 6.61-6.57 (m, 2H), 6.53 (d, J=8.1 Hz, 1H), 5.90 (s, 1H), 5.28 (m, 1H), 4.39 (s, 1H), 4.30 (dd, J=11.9, 4.4 Hz, 2H), 4.16 (dd, J=11.9, 5.8 Hz, 2H), 3.37 (s, 3H), 3.06 (ABq, 2H), 3.01-2.81 (m, 5H), 2.76 (t, J=6.7 Hz, 2H), 2.60 (dd, J=11.6, 4.8 Hz, 1H), 2.55 (s, 3H), 2.29 (t, J=7.6 Hz, 4H), 2.37-2.18 (m, 4H), 2.21 (s, 3H), 2.10 (t, J=9.8 Hz, 1H), 1.95 (td, J=12.6, 5.4 Hz, 1H), 1.89-1.74 (m, 2H), 1.71-1.51 (m, 11H), 1.33 (s, 3H), 1.45-1.14 (m, 49H), 1.02 (s, 9H), 0.88 (t, J=6.9 Hz, 6H), 0.83-0.61 (m, 2H), 0.54-0.42 (m, 2H). 0.14-0.07 (m, 2H).

ESI-HRMS: calcd. for C$_{81}$H$_{128}$NO$_{13}$ [M+H$^+$] 1322.9380; found 1322.9404.

Example 6. Synthesis of Compounds of the General Formula (III) Wherein R$^3$ is a p-Hydroxybenzyl (PHB) Carbonyl Self-Immolative Group a) 1,3-Bis(palmitoyloxy)propan-2-yl (4-(((tert-butyldimethylsilyl)oxy)methyl)-phenyl) succinate (xxi)

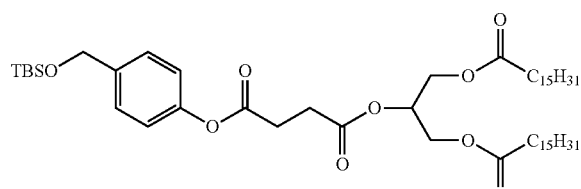

4-(Dimethylamino)pyridine (DMAP, 48.0 mg, 0.393 mmol) and EDC·HCl (123 mg, 0.639 mmol) were added to a solution of acid-TG iii (200 mg, 0.300 mmol) and phenol xx (93.1 mg, 0.391 mmol) in CH$_2$Cl$_2$ (15 mL) and the mixture stirred at rt for 21 hours. The reaction was diluted with CH$_2$Cl$_2$ (15 mL), silica gel was added and the mixture concentrated under reduced pressure. Purification by silica gel chromatography (5% to 15% ethyl acetate/hexanes) gave PHB triglyceride xxi (202 mg, 76%) as a colourless oil.

$^1$H NMR (400 MHz, CDCl$_3$) δ 7.34-7.29 (m, 2H), 7.07-7.02 (m, 2H), 5.30 (m, 1H), 4.72 (s, 2H), 4.31 (dd, J=12.0, 4.3 Hz, 2H), 4.16 (dd, J=12.0, 5.9 Hz, 2H), 2.88 (t, J=6.9 Hz, 2H), 2.76 (t, J=6.5 Hz, 2H), 2.29 (t, J=7.6 Hz, 4H), 1.63-1.55 (m, 4H), 1.33-1.20 (m, 48H), 0.94 (s, 9H), 0.88 (t, J=6.9 Hz, 6H), 0.09 (s, 6H).

b) 1,3-Bis(palmitoyloxy)propan-2-yl (4-(hydroxymethyl)phenyl) succinate (xxii)

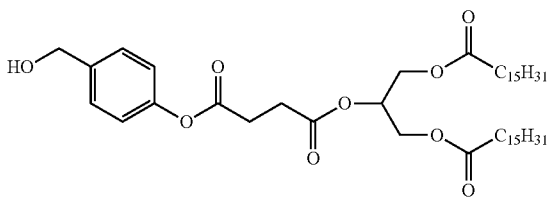

10-Camphorsulfonic acid (8.0 mg, 0.0344 μmol) was added to TBS ether xxi (181 mg, 0.203 μmol) in CH$_2$Cl$_2$ (2.5 mL) and MeOH (2.5 mL) and the mixture stirred at rt for 3.5 hours. The reaction was diluted with CH$_2$Cl$_2$ (30 mL) and the organic phase washed with sat. aq. NaHCO$_3$ (2×20 mL) and brine (20 mL), dried (MgSO$_4$) and concentrated under reduced pressure to give the crude product. Purification by silica gel chromatography (10% to 25% ethyl acetate/hexanes) gave alcohol xxii (128 mg, 81%) as a colourless solid.

$^1$H NMR (400 MHz, CDCl$_3$) δ 7.40-7.35 (m, 2H), 7.11-7.06 (m, 2H), 5.30 (m, 1H), 4.69 (d, J=5.9 Hz, 2H), 4.31 (dd, J=12.0, 4.3 Hz, 2H), 4.16 (dd, J=12.0, 5.9 Hz, 2H), 2.92-2.86 (m, 2H), 2.79-2.73 (m, 2H), 2.29 (t, J=7.6 Hz, 4H), 1.64-1.55 (m, 4H), 1.34-1.19 (m, 48H), 0.88 (t, J=6.9 Hz, 6H).

c) 1,3-Bis(palmitoyloxy)propan-2-yl (4-((((4-nitrophenoxy)carbonyl)oxy)methyl)-phenyl) succinate (xxiii)

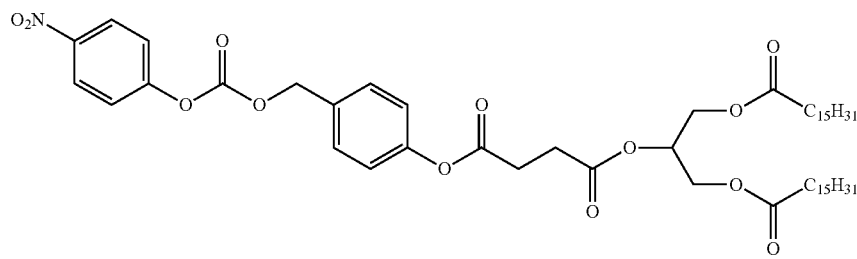

4-Nitrophenyl chloroformate (8.4 mg, 41.6 μmol) and pyridine (3.8 μL, 47.0 μmol) were added to alcohol xxii (20.0 mg, 25.8 μmol) in CH$_2$Cl$_2$ (2 mL) at 0° C. and the mixture stirred at 0° C. for 30 minutes and then at rt for 4.5 hours. The reaction was diluted with CH$_2$Cl$_2$ (30 mL) and the organic phase washed with sat. aq. NaHCO$_3$ and brine (3×25 mL each), dried (MgSO$_4$) and concentrated under reduced pressure to give the crude product. Purification by silica gel chromatography (10% to 20% ethyl acetate/hexanes) gave PNP carbonate xxiii (15.7 mg, 65%) as a colourless solid.

$^1$H NMR (400 MHz, CDCl$_3$) δ 8.31-8.25 (m, 2H), 7.48-7.43 (m, 2H), 7.41-7.36 (m, 2H), 7.17-7.11 (m, 2H), 5.29 (m, 1H), 5.28 (s, 2H), 4.32 (dd, J=12.0, 4.3 Hz, 2H), 4.17 (dd, J=12.0, 5.8 Hz, 2H), 2.93-2.87 (m, 2H), 2.79-2.73 (m, 2H), 2.30 (t, J=7.6 Hz, 4H), 1.63-1.51 (m, 4H), 1.34-1.18 (m, 48H), 0.88 (t, J=6.9 Hz, 6H).

d) 1,3-Bis(palmitoyloxy)propan-2-yl (4-((((((8R,9S, 10R,13S,14S,17S)-10,13-dimethyl-3-oxo-2,3,6,7,8, 9,10,11,12,13,14,15,16,17-tetradecahydro-1H-cyclopenta[a]phen-anthren-17-yl)oxy)carbonyl)oxy) methyl)phenyl) succinate (16)

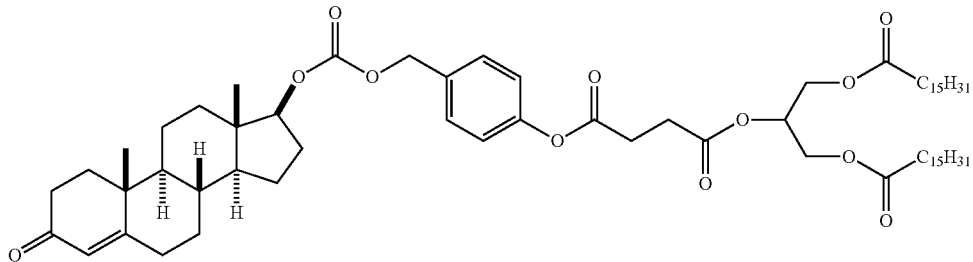

4-(Dimethylamino)pyridine (DMAP, 21.3 mg, 0.174 μmol) and DIPEA (7.1 μL, 0.0406 mmol) were added to a solution of testosterone (48.0 mg, 0.166 μmol) and PNP carbonate xxiii (127 mg, 0.135 μmol) in $CH_2Cl_2$ (10 mL) and the mixture stirred at rt for five days. The reaction was diluted with $CH_2Cl_2$ (20 mL), washed with 1 M HCl, water and brine (20 mL each), dried ($MgSO_4$) and concentrated under reduced pressure to give the crude product. Purification by silica gel chromatography (5% ethyl acetate/toluene) gave Compound 16 (20.4 mg, 14%) as a colourless solid.

$^1$H NMR (400 MHz, $CDCl_3$) δ 7.42-7.37 (m, 2H), 7.12-7.05 (m, 2H), 5.73 (s, 1H), 5.29 (m, 1H), 5.12 (s, 2H), 4.52 (t, J=8.4 Hz, 1H), 4.31 (dd, J=12.0, 4.3 Hz, 2H), 4.16 (dd, J=12.0, 5.9 Hz, 2H), 2.89 (t, J=6.7 Hz, 2H), 2.76 (t, J=6.7 Hz, 2H), 2.47-2.34 (m, 3H), 2.29 (t, J=7.6 Hz, 4H), 2.34-2.16 (m, 2H), 2.02 (m, 1H), 1.89-1.80 (m, 2H), 1.74-1.53 (m, 8H), 1.47-1.19 (m, 51H), 1.18 (s, 3H), 1.10-0.92 (m, 4H), 0.88 (t, J=6.9 Hz, 6H), 0.85 (s, 3H).

ESI-HRMS: calcd. for $C_{66}H_{105}O_{12}$ [M+H$^+$] 1089.7601; found 1089.7617.

Example 7. Synthesis of Compounds of the General Formula (III) Wherein $R^3$ is a Flipped-Ester Self Immolative (FSI) Group a) (8R,9S,10R,13S,14S,17S)-10,13-Dimethyl-3-oxo-2,3,6,7,8,9,10,11,12,13,14,15-16,17-tetradecahydro-1H-cyclopenta[a]phenanthren-17-yl 4-bromobutanoate (xxvi)

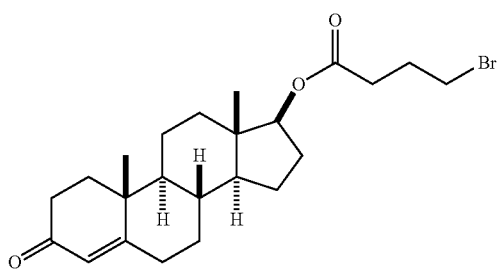

4-(Dimethylamino)pyridine (DMAP, 15.5 mg, 0.130 mmol) and DCC (43.8 mg, 0.210 mmol) were added to a solution of testosterone (29.9 mg, 0.100 mmol) and 4-bromobutyric acid (xxv) (21.0 mg, 0.130 mmol) in $CH_2Cl_2$ (3 mL) and the mixture stirred at rt for 24 hours. Another 0.6 eq. of acid, 1 eq. of DCC, 0.6 eq. of DMAP were added and the mixture was stirred at rt for a further two days. The reaction was diluted with $CH_2Cl_2$ (10 mL), silica gel was added and the mixture concentrated under reduced pressure. Purification by silica gel chromatography (25% ethyl acetate/hexanes) gave bromide xxvi (26.7 mg, 59%) as a colourless solid.

$^1$H NMR (400 MHz, $CDCl_3$) δ 5.73 (s, 1H), 4.62 (dd, J=9.1, 7.9 Hz, 1H), 3.47 (t, J=6.5 Hz, 2H), 2.50 (td, J=7.1, 1.0 Hz, 2H), 2.47-2.23 (m, 4H), 2.22-2.13 (m, 3H), 2.06-1.99 (m, 1H), 1.85 (m, 1H), 1.78 (m, 1H), 1.74-1.63 (m, 2H), 1.61-1.53 (m, 2H), 1.52-1.32 (m, 3H), 1.23-1.15 (m, 1H), 1.19 (s, 3H) 1.11-0.91 (m, 3H), 0.83 (s, 3H).

b) 1,3-Bis(palmitoyloxy)propan-2-yl (4-(((8R,9S, 10R,13S,14S,17S)-10,13-dimethyl-3-oxo-2,3,6,7,8, 9,10,11,12,13,14,15,16,17-tetradecahydro-1H-cyclopenta[a]phenanthren-17-yl)oxy)-4-oxobutyl) succinate (17)

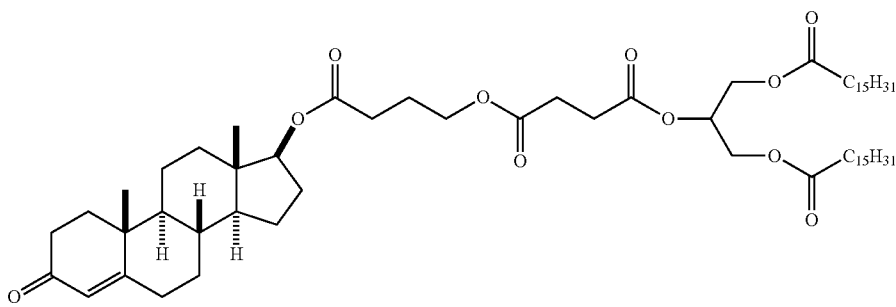

1,8-Diazabicyclo[5.4.0]undec-7-ene (DBU) (9.9 μL, 66.2 μmol) was added to a suspension of acid-TG iii (30.9 mg, 46.2 μmol) and bromide xxvi (18.3 mg, 41.8 μmol) toluene (1.5 mL) and the mixture heated at reflux for 21 hours. The reaction was cooled to rt, then diluted with ethyl acetate (20 mL). The organic phase was washed with water (10 mL) and brine (10 mL), dried ($MgSO_4$) and concentrated under reduced pressure to give the crude product. Silica gel chromatography (15% to 25% ethyl acetate/hexane) gave Compound 17 (21.6 mg, 50%) as a colourless solid.

$^1$H NMR (400 MHz, $CDCl_3$) δ 5.73 (s, 1H), 5.26 (m, 1H), 4.62 (dd, J=9.1, 7.9 Hz, 1H), 4.30 (dd, J=11.9, 4.4 Hz, 2H), 4.15 (dd, J=11.9, 5.8 Hz, 2H), 4.13 (t, J=6.5 Hz, 2H), 2.69-2.58 (m, 4H), 2.47-2.25 (m, 9H), 2.19 (m, 1H), 2.07-1.91 (m, 3H), 1.85 (m, 1H), 1.78 (m, 1H), 1.75-1.45 (m, 9H), 1.44-1.21 (m, 59H), 1.19 (s, 3H), 1.16-0.91 (m, 5H), 0.88 (t, J=6.9 Hz, 6H), 0.83 (s, 3H).

ESI-HRMS: calcd. for $C_{62}H_{104}O_{11}Na$ [M+Na$^+$] 1047.7471; found 1047.7460.

The following flipped-ester self-immolative group containing compounds were prepared according to the above methods:

1,3-Bis(palmitoyloxy)propan-2-yl (5-(((8R,9S,10R, 13S,14S,17S)-10,13-dimethyl-3-oxo-2,3,6,7,8,9,10, 11,12,13,14,15,16,17-tetradecahydro-1H-cyclopenta [a]phenanthren-17-yl)oxy)-5-oxopentyl) succinate (18)

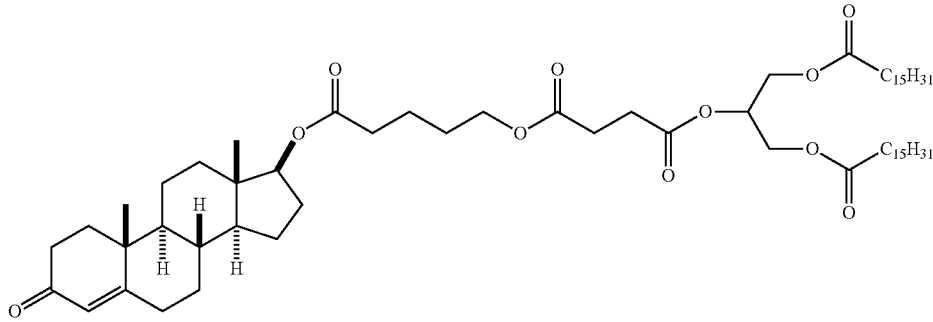

$^1$H NMR (400 MHz, CDCl$_3$) δ 5.73 (s, 1H), 5.26 (m, 1H), 4.61 (dd, J=9.1, 7.9 Hz, 1H), 4.29 (dd, J=11.9, 4.4 Hz, 2H), 4.15 (dd, J=11.9, 5.8 Hz, 2H), 4.10 (t, J=6.0 Hz, 2H), 2.68-2.58 (m, 4H), 2.47-2.25 (m, 10H), 2.18 (m, 1H), 2.02 (ddd, J=13.3, 4.9, 3.3 Hz, 1H), 1.85 (m, 1H), 1.77 (m, 1H), 1.74-1.45 (m, 13H), 1.44-1.21 (m, 50H), 1.19 (s, 3H), 1.18-0.91 (m, 4H), 0.88 (t, J=6.9 Hz, 6H), 0.83 (s, 3H).

ESI-HRMS: calcd. for C$_{63}$H$_{107}$O$_{11}$Na [M+Na$^+$] 1061.7627; found 1061.7654.

1-(1,3-Bis(palmitoyloxy)propan-2-yl) 4-(5-(((8R,9S, 10R,13S,14S,17S)-10,13-dimethyl-3-oxo-2,3,6,7,8, 9,10,11,12,13,14,15,16,17-tetradecahydro-1H-cyclo-penta[a]phenanthren-17-yl)oxy)-5-oxopentyl) 2-methylsuccinate (19)

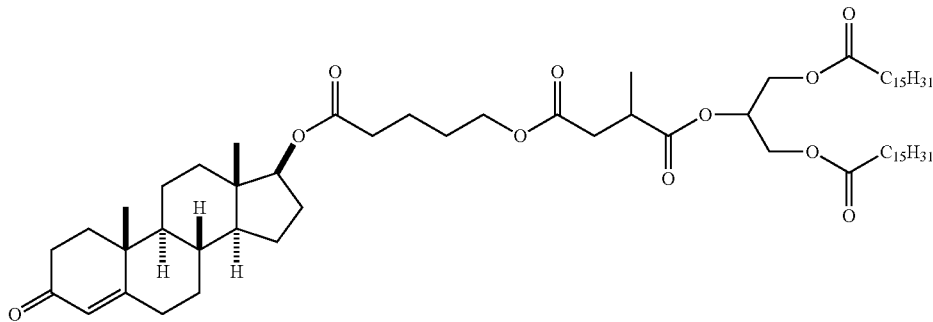

$^1$H NMR (400 MHz, CDCl$_3$) δ 5.73 (s, 1H), 5.26 (m, 1H), 4.61 (dd, J=9.1, 7.9 Hz, 1H), 4.33-4.24 (m, 2H), 4.21-4.04 (m, 4H), 2.91 (m, 1H), 2.76/2.72 (each dd, J=13.9, 7.9 Hz, 1H), 2.47-2.26 (m, 11H), 2.18 (m, 1H), 2.02 (m, 1H), 1.84 (m, 1H), 1.77 (m, 1H), 1.74-1.44 (m, 13H), 1.43-1.14 (m, 51H), 1.223/1.214 (each d, J=7.2 Hz, 3H), 1.19 (s, 3H), 1.11-0.92 (m, 3H), 0.88 (t, J=6.9 Hz, 6H), 0.83 (s, 3H). Note: doubled signals reflect the presence of a mixture of diastereoisomers.

ESI-HRMS: calcd. for C$_6$H$_{109}$O$_{11}$ [M+H$^+$] 1053.7964; found 1053.7984.

1,3-Bis(palmitoyloxy)propan-2-yl (5-(((4aS,6R,7R,7aR,12bS)-3-(cyclopropylmethyl)-6-((S)-2-hydroxy-3,3-dimethylbutan-2-yl)-7-methoxy-1,2,3,4,5,6,7,7a-octahydro-4a,7-ethano-4,12-methanobenzofuro[3,2-e]isoquinolin-9-yl)oxy)-5-oxopentyl) succinate (7)

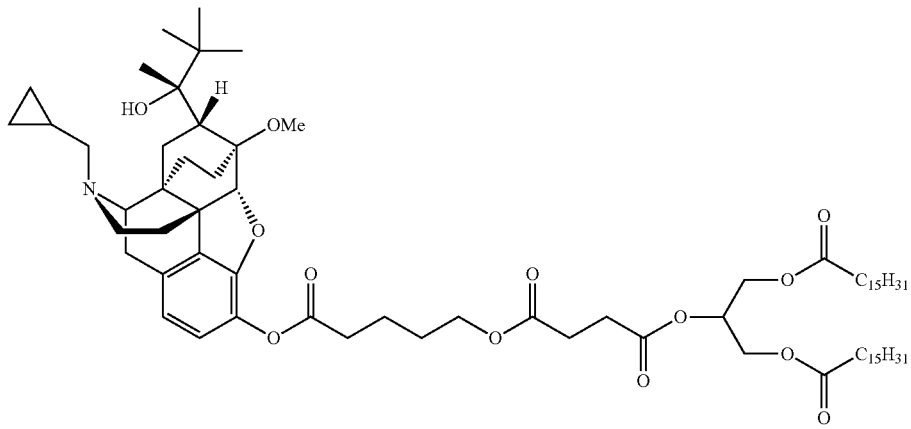

$^1$H NMR (400 MHz, CDCl$_3$) δ 6.77 (d, J=8.1 Hz, 1H), 6.59 (d, J=8.1 Hz, 1H), 5.88 (s, 1H), 5.26 (m, 1H), 4.42 (d, J=1.6 Hz, 1H), 4.29 (dd, J=11.9, 4.4 Hz, 2H), 4.15 (dd, J=12.0, 5.8 Hz, 2H), 4.11 (t, J=6.0 Hz, 2H), 3.45 (s, 3H), 3.02 (d, J=13.5 Hz, 1H), 2.99 (s, 1H), 2.88 (m, 1H), 2.67-2.54 (m, 7H), 2.38-2.22 (m, 8H), 2.11 (t, J=10.1 Hz, 1H), 1.97 (td, J=12.7, 5.6 Hz, 1H), 1.91-1.84 (m, 2H), 1.82-1.68 (m, 5H), 1.65-1.57 (m, 4H), 1.35 (s, 3H), 1.35-1.19 (m, 49H), 1.05 (m, 1H), 1.03 (s, 9H), 0.88 (t, J=6.9 Hz, 6H), 0.84-0.76 (m, 1H), 0.75-0.63 (m, 1H), 0.55-0.43 (m, 2H), 0.17-0.08 (m, 2H).

ESI-HRMS: calcd. for C$_{73}$H$_{120}$NO$_{13}$ [M+H$^+$] 1218.8754; found 1218.8775.

1-(1,3-Bis(palmitoyloxy)propan-2-yl) 4-(5-(((4aS,6R,7R,7aR,12bS)-3-(cyclopropylmethyl)-6-((S)-2-hydroxy-3,3-dimethylbutan-2-yl)-7-methoxy-1,2,3,4,5,6,7,7a-octahydro-4a,7-ethano-4,12-methanobenzofuro[3,2-e]isoquinolin-9-yl)oxy)-5-oxopentyl) 2-methylsuccinate (8)

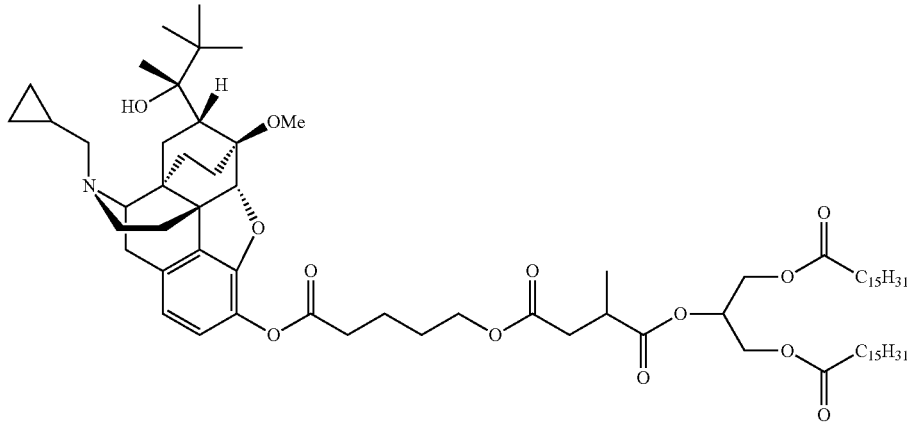

¹H NMR (400 MHz, CDCl₃) δ 6.77 (d, J=8.1 Hz, 1H), 6.59 (d, J=8.1 Hz, 1H), 5.88 (s, 1H), 5.26 (m, 1H), 4.42 (d, J=1.5 Hz, 1H), 4.32-4.24 (m, 2H), 4.20-4.06 (m, 4H), 3.45 (s, 3H), 3.02 (d, J=13.3 Hz, 1H), 2.99 (s, 1H), 2.96-2.84 (m, 2H), 2.74 (ddd, J=16.6, 13.4, 8.0 Hz, 1H), 2.66-2.53 (m, 3H), 2.46-2.21 (m, 9H), 2.11 (t, J=9.9 Hz, 1H), 1.97 (td, J=12.5, 5.6 Hz, 1H), 1.92-1.67 (m, 7H), 1.65-1.56 (m, 4H), 1.35 (s, 3H), 1.34-1.17 (m, 49H), 1.222 (d, J=7.2 Hz, 1.5H), 1.116 (d, J=7.2 Hz, 1.5H), 1.05 (m, 1H), 1.03 (s, 9H), 0.88 (t, J=6.8 Hz, 6H), 0.80 (m, 1H), 0.67 (m, 1H), 0.55-0.42 (m, 2H), 0.15-0.08 (m, 2H).

ESI-HRMS: calcd. for $C_{74}H_{122}NO_{13}$ [M+H⁺] 1232.8911; found 1232.8925.

1,3-Bis(palmitoyloxy)propan-2-yl (5-((1-(isopropylamino)-3-(4-(2-methoxyethyl)-phenoxy)propan-2-yl)oxy)-5-oxopentyl) succinate (9)

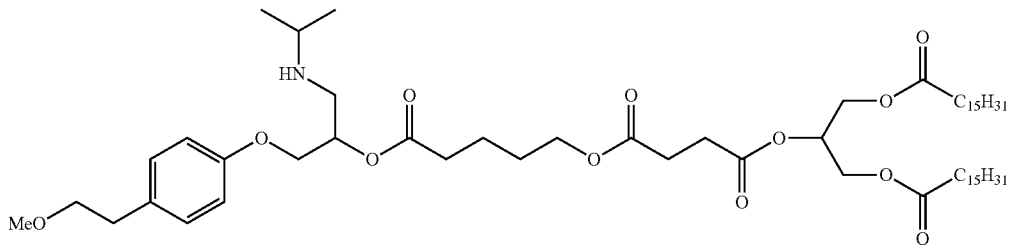

Trifluoroacetic acid (TFA, 6.1 µL, 82.2 µmol) was added to Boc-protected prodrug xxvii (9.2 mg, 8.2 µmol) in CH₂Cl₂ (1.2 mL) at 0° C. and the mixture stirred at rt for 21 hours. The reaction was concentrated under a stream of N₂ gas to give the crude product. Silica gel chromatography (1% to 3.5% methanol/CH₂Cl₂) gave Compound 9 (6.8 mg, 81%) as a pale yellow oil.

¹H NMR (400 MHz, CDCl₃) δ 7.13 (d, J=8.6 Hz, 2H), 6.84-6.77 (m, 2H), 5.38 (m, 1H), 5.24 (m, 1H), 4.28 (dd, J=11.9, 4.5 Hz, 2H), 4.18-4.10 (m, 4H), 4.06 (t, J=5.7 Hz, 2H), 3.55 (t, J=7.0 Hz, 2H), 3.34 (s, 3H), 3.38-3.24 (m, 3H), 2.81 (t, J=7.0 Hz, 2H), 2.66-2.56 (m, 4H), 2.48-2.35 (m, 2H), 2.31 (t, J=7.6 Hz, 4H), 1.69-1.54 (m, 8H), 1.32 (d, J=6.4 Hz, 6H), 1.37-1.19 (m, 48H), 0.88 (t, J=6.9 Hz, 6H).

ESI-HRMS: calcd. for $C_{59}H_{104}NO_{12}$ [M+H⁺] 1018.7553; found 1018.7568.

Example 8. Synthesis of Compounds of the General Formula (IV) Wherein the Pharmaceutical Agent is Mycophenolic Acid (MPA)

a) 1-(1,3-Bis(palmitoyloxy)propan-2-yl) 5-(chloromethyl) 3-methylpentanedioate (xviii)

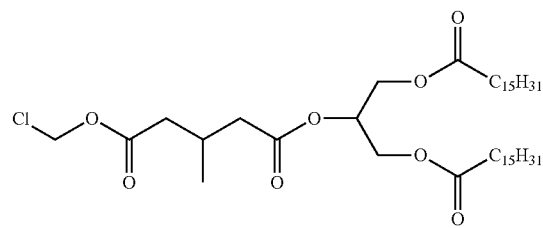

A mixture of acid-TG iii (75.0 mg, 0.108 mmol), N,N-dimethylformamide (DMF, one drop) and SOCl₂ (78.0 µL, 1.08 mmol) was heated at reflux for 45 minutes and then cooled to rt. The reaction was concentrated under reduced pressure, and then co-evaporated three times from toluene (3 mL each) and dried under reduced pressure. The resulting acid chloride was re-dissolved in CH₂Cl₂ (1 mL) and added dropwise to anhydrous ZrCl₄ (25.1 mg, 0.108 mmol) in CH₂Cl₂ (0.5 mL), stirred at rt for 15 minutes and then cooled to 0° C. 1,3,5-Trioxane (9.7 mg, 0.108 mmol) was added and the mixture stirred at rt for 20 hours. The reaction was diluted with CH₂Cl₂ (15 mL) and the organic phase washed with water and brine (15 mL each), dried (MgSO₄) and concentrated under reduced pressure to give the crude product. Purification by silica gel chromatography (5% to 12.5% ethyl acetate/hexanes) gave chloromethyl ester xxviii (19.2 mg, 24%) as a yellow oil.

¹H NMR (400 MHz, CDCl₃) δ 5.72-5.67 (m, 2H), 5.27 (m, 1H), 4.31 (dd, J=11.9, 4.2 Hz, 2H), 4.13 (dd, J=12.0, 6.1 Hz, 2H), 2.53-2.34 (m, 5H), 2.31 (t, J=7.6 Hz, 4H), 1.67-1.53 (m, 4H), 1.37-1.19 (m, 48H), 1.05 (d, J=6.5 Hz, 3H), 0.88 (t, J=6.9 Hz, 6H).

b) (E)-1-(((6-(4-(Allyloxy)-6-methoxy-7-methyl-3-oxo-1,3-dihydroisobenzofuran-5-yl)-4-meth-ylhex-4-enoyl)oxy)methyl) 5-(1,3-bis(palmitoyloxy)propan-2-yl) 3-methylpentanedioate (xxxi)

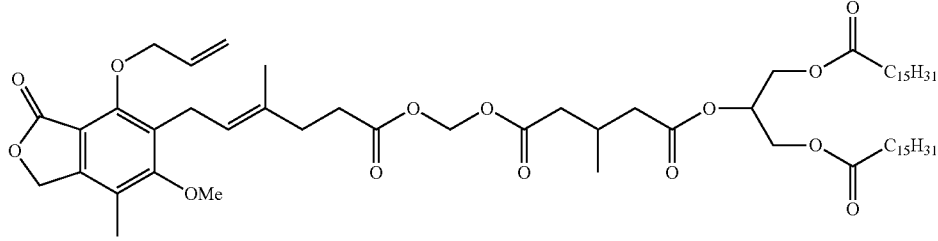

1,8-Diazabicyclo[5.4.0]undec-7-ene (DBU) (6.9 μL, 45.9 μmol) was added to a suspension of MPA(OA11) xxx (12.9 mg, 35.7 μmol) and chloromethyl ester xxviii (19.0 mg, 25.5 μmol) and TBAI (4.7 mg, 12.7 μmol) in toluene (0.8 mL) and the mixture heated at 80° C. for two hours. The reaction was cooled to rt, then diluted with ethyl acetate (20 mL). The organic phase was washed with water and brine (20 mL each), dried (MgSO$_4$) and concentrated under reduced pressure to give the crude product. Silica gel chromatography (15% to 20% ethyl acetate/hexane) gave protected prodrug xxxi (16.7 mg, 61%) as a colourless solid.

$^1$H NMR (400 MHz, CDCl$_3$) δ 6.09 (m, 1H), 5.69 (s, 2H), 5.36 (m, 1H), 5.31-5.22 (m, 2H), 5.18 (td, J=6.7, 1.2 Hz, 1H), 5.13 (s, 2H), 4.78 (dt, J=5.9, 1.2 Hz, 2H), 4.292/4.288 (each dd, J=11.9, 4.3 Hz, 2H), 4.13 (dd, J=11.9, 5.9 Hz, 2H), 3.76 (s, 3H), 3.41 (d, J=6.7 Hz, 2H), 2.50-2.37 (m, 5H), 2.34-2.23 (m, 8H), 2.18 (s, 3H), 1.77 (s, 3H), 1.64-1.56 (m, 4H), 1.35-1.18 (m, 48H), 1.02 (d, J=6.4 Hz, 3H), 0.87 (t, J=6.9 Hz, 6H). Note: doubled signals reflect the presence of a mixture of diastereoisomers.

c) (E)-1-(1,3-Bis(palmitoyloxy)propan-2-yl) 5-(((6-(4-hydroxy-6-methoxy-7-methyl-3-oxo-1,3-dihydroisobenzofuran-5-yl)-4-methylhex-4-enoyl)oxy)methyl) 3-methyl-pentanedioate (10)

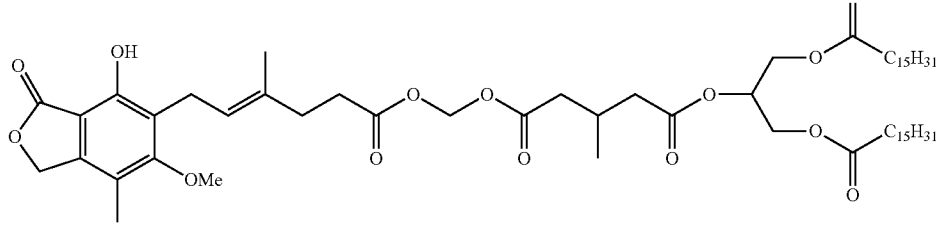

1,3-Dimethylbarbituric acid (4.9 mg, 31.2 μmol) and Pd(PPh$_3$)$_4$ (5.4 mg, 4.7 μmol) were added to allyl ether xxxi (16.7 mg, 15.6 μmol) in CH$_2$Cl$_2$ (0.5 mL) and the mixture stirred at rt for two hours. The reaction mixture was directly applied to a short pad of silica gel and eluted with 50% ethyl acetate/hexanes. The eluent was concentrated under reduced pressure to give the crude product, which was purified by silica gel chromatography (5% to 10% ethyl acetate/toluene) to give Compound 10 (10.1 mg, 63%) as a colourless solid.

$^1$H NMR (400 MHz, CDCl$_3$) δ 7.68 (s, 1H), 5.70 (s, 2H), 5.30-5.21 (m, 2H), 5.20 (s, 2H), 4.296/4.291 (each dd, J=11.9, 4.3 Hz, 2H), 4.13 (dd, J=11.9, 6.0 Hz, 2H), 3.76 (s, 3H), 3.38 (d, J=6.9 Hz, 2H), 2.49-2.38 (m, 5H), 2.34-2.25 (m, 8H), 2.15 (s, 3H), 1.79 (s, 3H), 1.66-1.54 (m, 4H), 1.35-1.19 (m, 48H), 1.02 (d, J=6.4 Hz, 3H), 0.88 (t, J=6.9 Hz, 6H). Note: doubled signals reflect the presence of a mixture of diastereoisomers.

ESI-HRMS: calcd. for C$_{59}$H$_{97}$O$_{14}$ [M+H$^+$] 1029.6873; found 1029.6890.

The following compounds of general formula (IV) were prepared according to the above methods:

a2) 1-(1,3-Bis(palmitoyloxy)propan-2-yl) 5-(1-chloroethyl) 3-methylpentanedioate (xxviii)

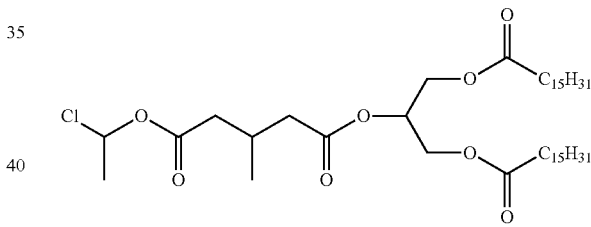

A mixture of acid-TG iii (120 mg, 0.172 mmol), N,N-dimethylformamide (DMF, one drop) and SOCl$_2$ (125 μL, 1.72 mmol) was heated at reflux for 1.25 hours and then cooled to rt. The reaction was concentrated under reduced pressure, and then co-evaporated three times from toluene (3 mL each) and dried under reduced pressure. The resulting acid chloride was re-dissolved in CH$_2$Cl$_2$ (1.5 mL), added dropwise to anhydrous ZnCl$_2$ (23.5 mg, 0.172 mmol) in CH$_2$Cl$_2$ (0.5 mL) at 0° C. and stirred at 0° C. for five minutes. Paraldehyde (45.6 μL, 0.344 μmol) was added and the mixture stirred at 0° C. for 10 minutes and at rt for one hour. The reaction was diluted with $CH_2Cl_2$ (20 mL) and the organic phase washed with water and brine (20 mL each), dried ($MgSO_4$) and concentrated under reduced pressure to give the crude product. Purification by silica gel chromatography (5% to 15% ethyl acetate/hexanes) gave 1-chloroethyl ester xxviii (14.9 mg, 11%) as a yellow oil.

b2) (E)-1-(1,3-Bis(palmitoyloxy)propan-2-yl) 5-(1-((6-(4-hydroxy-6-methoxy-7-methyl-3-oxo-1,3-dihydroisobenzofuran-5-yl)-4-methylhex-4-enoyl)oxy)ethyl) 3-methylpentanedioate (11)

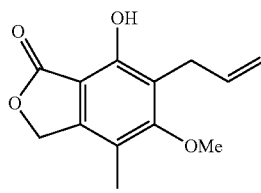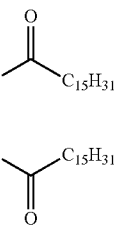

$^1$H NMR (401 MHz, $CDCl_3$) δ 7.68 (s, 1H), 6.80 (q, J=5.4 Hz, 1H), 5.29-5.21 (m, 2H), 5.20 (s, 2H), 4.32-4.26 (m, 2H), 4.132/4.127 (each dd, J=11.9, 6.0 Hz, 2H), 3.76 (s, 3H), 3.38 (d, J=6.9 Hz, 2H), 2.48-2.35 (m, 5H), 2.32-2.18 (m, 8H), 2.15 (s, 3H), 1.79 (s, 3H), 1.64-1.54 (m, 4H), 1.41 (d, J=5.4 Hz, 3H), 1.36-1.18 (m, 48H), 1.01 (d, J=6.4 Hz, 3H), 0.88 (t, J=6.9 Hz, 6H). Note: doubled signals reflect the presence of a mixture of diastereoisomers.

ESI-HRMS: calcd. for $C_{60}H_{99}O_{14}Na$ [M+Na$^+$] 1065.6849; found 1065.6879.

Example 9. Lymphatic Transport Studies in Rats

In order to assess the lymphatic transport of the compounds of the invention in rats, the mesenteric lymph duct of the rats was cannulated to allow continual collection of mesenteric lymph. Lipid formulations containing the compound of interest were then administered to the animals. The lymph was collected and drug concentrations in the lymph were subsequently quantified.

Lipid-based formulations of the compounds of the invention or control compounds were prepared as previously described (Trevaskis, N. L. et al., Pharmaceutical Research, 2005, 22(11), 1863-1870). Briefly, approximately 2 mg of the compound (1.5 mg for Compound 19 and 0.05 mg for Compounds 6 and 7), 40 mg oleic acid and 25 mg Tween 80 were mixed in a glass vial until equilibrated (gentle heat (below 50° C.) may be applied for a short period). An aqueous phase consisting of 5.6 mL phosphate buffered saline (PBS, pH 7.4) was subsequently added to the lipid phase and the formulation emulsified by ultrasonication with a ultrasonic processor equipped with a 3.2-mm microprobe tip running at an amplitude of 240 μm and a frequency of 20 kHz for 2 min at room temperature. Compound concentrations in all formulations were verified using HPLC-MS-MS.

Male Sprague-Dawley (SD) rats were selected for the lymphatic transport studies where the pharmaceutical agent was mycophenolic acid (MPA), sertraline (SER) or Buprenorphine (BUP). Female SD rats were selected for studies where the pharmaceutical agent was testosterone. This was to eliminate the potential for the relatively high and variable levels of endogenous testosterone in male rats interfering with the quantification of exogenously dosed testosterone. Rats (220-320 g) were maintained on a standard diet and fasted overnight with free access to water prior to experiments. Anaesthetised rats were placed on a heated pad at 37° C. and cannulas were inserted into the duodenum (for formulation administration and rehydration), mesenteric lymph duct (for lymph collection) and carotid artery (for blood collection) as previously described (Edwards et al. Advanced Drug Delivery Reviews 2001, 50(1), 45-60). Post-surgery, rats were re-hydrated for 0.5 h via intraduodenal infusion of normal saline at 2.8 mL/h. The lipid formulations were infused into the duodenum at 2.8 mL/h for 2 h after which, normal saline was infused at 2.8 mL/h for the remainder of the experiment. Lymph was continuously collected for up to 8 h into pre-weighed Eppendorf tubes containing 10 μL of 1,000 IU/mL heparin. The collection tubes were changed hourly and lymph flow was measured gravimetrically. Aliquots of hourly lymph samples were stored at −80° C. prior to assay.

Drug concentration in lymph is expressed as total drug and includes free drug and drug associated with different glycerides. This is assayed by hydrolysis of lymph (to liberate drug from any re-esterified glycerides) prior to assessment of free drug.

Transport of compounds into lymph during each hourly collection period was calculated from the product of the volume of lymph collected and the measured concentrations in lymph.

As shown in FIG. 1 and Table 4, the lymphatic transport Compound 12, having an acetal self-immolative group (ASI), Compound 15, having a trimethyl-lock (TML) self immolative group and Compound 17, having a (4-carbon) flipped-ester self immolative group (FSI-4) was 1.9%, 3.2% and 5.2% (of administered dose), respectively. This is lower than the straight chain counterpart testosterone-succinic acid-TG (Compound 21, 13.4%), with Compound 12 decreasing to the level of the currently marketed testosterone prodrug testosterone undecanoate (TU). The reduction in lymphatic transport of the prodrug containing the self immolative is likely due to poor stability of the monoglyceride form of the prodrugs in the gastrointestinal tract (as described in Example 11 below and shown in FIG. 9), or potentially due to reduced efficiency of re-esterification of the monoglyceride form in enterocytes. The order of stability of the monoglyceride forms of Compound 21, Compound 12 and Compound 17 (i.e., Compound 21-monoglyceride>Compound 17-monoglyceride>Compound 12-monoglceride) is consistent with the rank of the lymphatic transport of these three prodrugs (i.e., Compound 21>Compound 17>Compound 12).

Inclusion of a methyl group on the carbon alpha or beta to the glyceride unit increases the stability of the monoglyceride intermediates of the prodrugs. For example, to address the stability issue for Compound 12, a methyl protecting group was included in the compound to form Compounds 13 and 14 (the compounds were used as a mixture of Compounds 13 and 14). As is evident from FIG. 1 and Table 4, the inclusion of a methyl protecting group significantly enhanced the lymphatic transport for Compounds 13 and 14 compared to Compound 12. This is consistent with an increased stability under GI digesting conditions (see FIG. 9). The lymphatic transport for Compound 19 (containing a 5-carbon flipped-ester self immolative group [FSI-5] with a methyl branch) was 9.6% (of administered dose). This is also higher than that for a similar compound, Compound 17 (containing a FSI-4 self immolative group) but lacking the methyl group.

TABLE 4

Lymphatic transport of total compound (% of administered dose) following intraduodenal infusion to anaesthetised, mesenteric lymph-duct cannulated rats (data are presented as mean ± SEM when n ≥ 3 or mean ± range when n = 2).

| Compound | Transport of total TST derivatives in lymph (% of dose) | Fold increase (compared with control group dosed with TU) |
|---|---|---|
| Testosterone (n = 3) | Below LOQ* | 0 |
| TU (n = 4) | 1.9 ± 0.3 | 1.0 |
| 21 (n = 4) | 13.4 ± 1.7 | 7.2 |
| 12 (n = 3) | 1.9 ± 0.4 | 1.0 |
| 13/14 (n = 3) | 8.0 ± 2.5 | 4.2 |
| 15 | 3.2 ± 0.4 | 1.7 |
| 17 (n = 2) | 5.2 ± 0.0 | 2.8 |
| 19 | 9.6 ± 2.2 | 5.1 |

Figure 4:
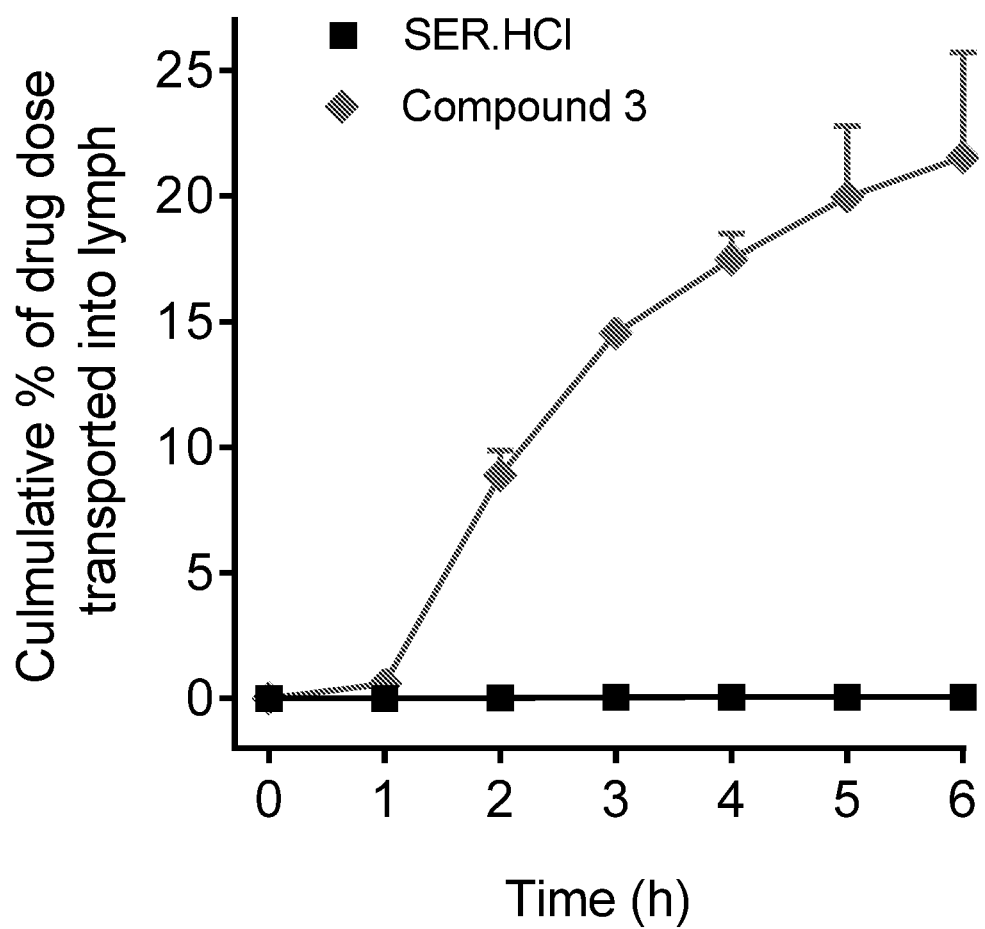
FIG. 4: Graphical representation of the cumulative lymphatic transport of total sertraline (SER) related derivatives (% of administered dose) versus time in anaesthetised, mesenteric lymph duct cannulated male SD rats following intraduodenal infusion of SER hydrochloride (SER·HCl) and Compound 3.

*Concentrations of testosterone in lymph samples were below the limit of quantification As shown in FIG. 4 and Table 5, the lymphatic transport of Compound 3, having a TML self-immolative group, was 21.5% (of administered dose). In contrast, the lymphatic transport of the parent drug sertraline (SER) was only 0.05% (of administered dose) following administration of the parent drug SER·HCl.

TABLE 5

Lymphatic transport of total compound (% of administered dose) following intraduodenal infusion to anaesthetised, mesenteric lymph-duct cannulated rats (data are presented as mean ± SEM when n ≥ 3 or as single value when n = 1).

| Compound | Transport of total TST derivatives in lymph (% of dose) | Fold increase (compared with control group dosed with parent drug) |
|---|---|---|
| SER · HCl (n = 1) | 0.05 | 1.0 |
| 3 (n = 3) | 21.5 ± 4.2 | 422 |

Figure 6:
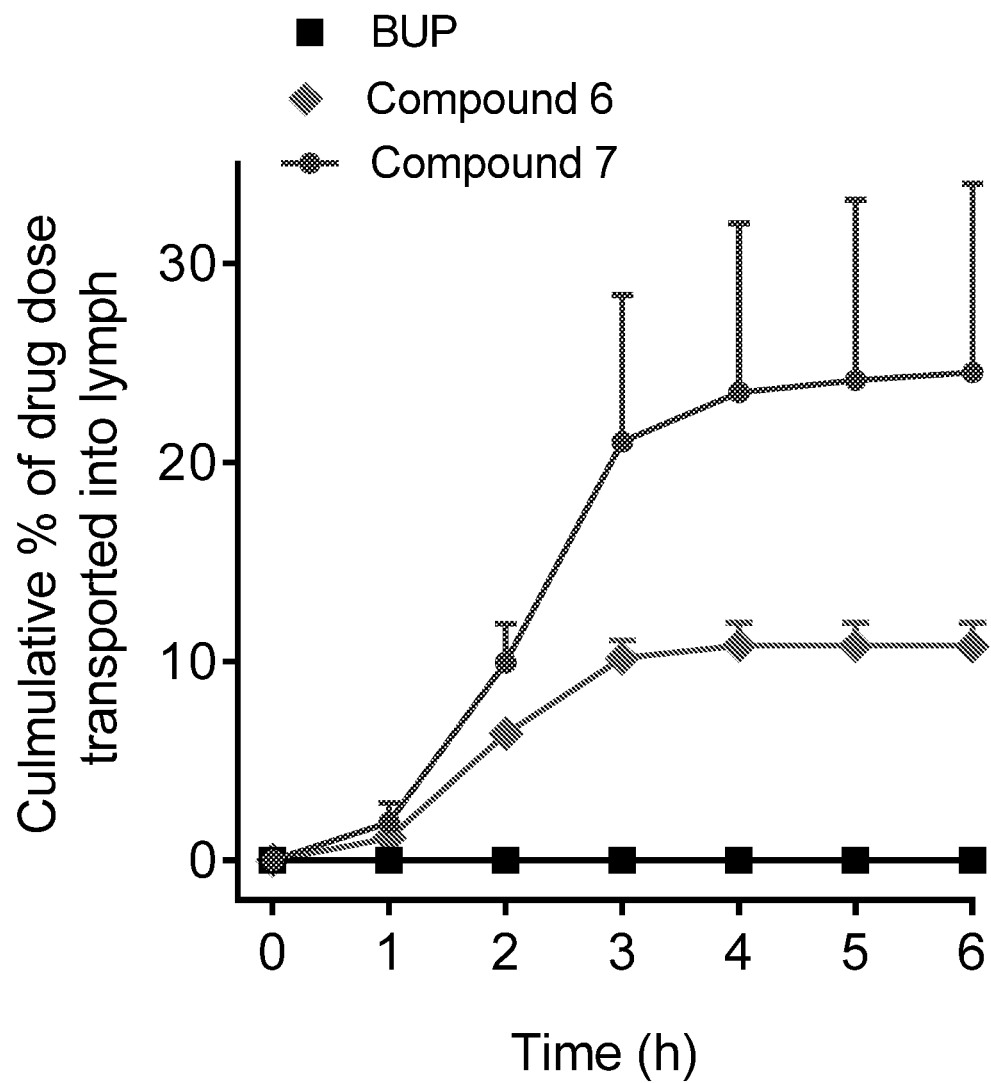
FIG. 6: Graphical representation of the cumulative lymphatic transport of total buprenorphine (BUP) related derivatives (% of administered dose) versus time in anaesthetised, mesenteric lymph duct cannulated male SD rats following intraduodenal infusion of BUP, Compound 6, and Compound 7.

As shown in FIG. 6 and Table 4, the lymphatic transport of Compound 6, having a TML self-immolative group, and Compound 7, having a (5-carbon) flipped-ester self immolative group (FSI-5), was 10.8% and 24.5% (of administered dose). In contrast the lymphatic transport of parent drug buprenorphine (BUP) was extremely low, only 0.01% (of administered dose) following administration of BUP.

TABLE 6

Lymphatic transport of total compound (% of administered dose) following intraduodenal infusion to anaesthetised, mesenteric lymph-duct cannulated rats (data are presented as mean ± SEM when n ≥ 3 or mean ± range when n = 2).

| Compound | Transport of total TST derivatives in lymph (% of dose) | Fold increase (compared with control group dosed with parent drug) |
|---|---|---|
| BUP (n = 2) | 0.01 ± 0.008 | 1.0 |
| 6 (n = 3) | 10.8 ± 1.2 | 1296 |
| 7 (n = 2) | 24.5 ± 9.4 | 2950 |

Figure 8:
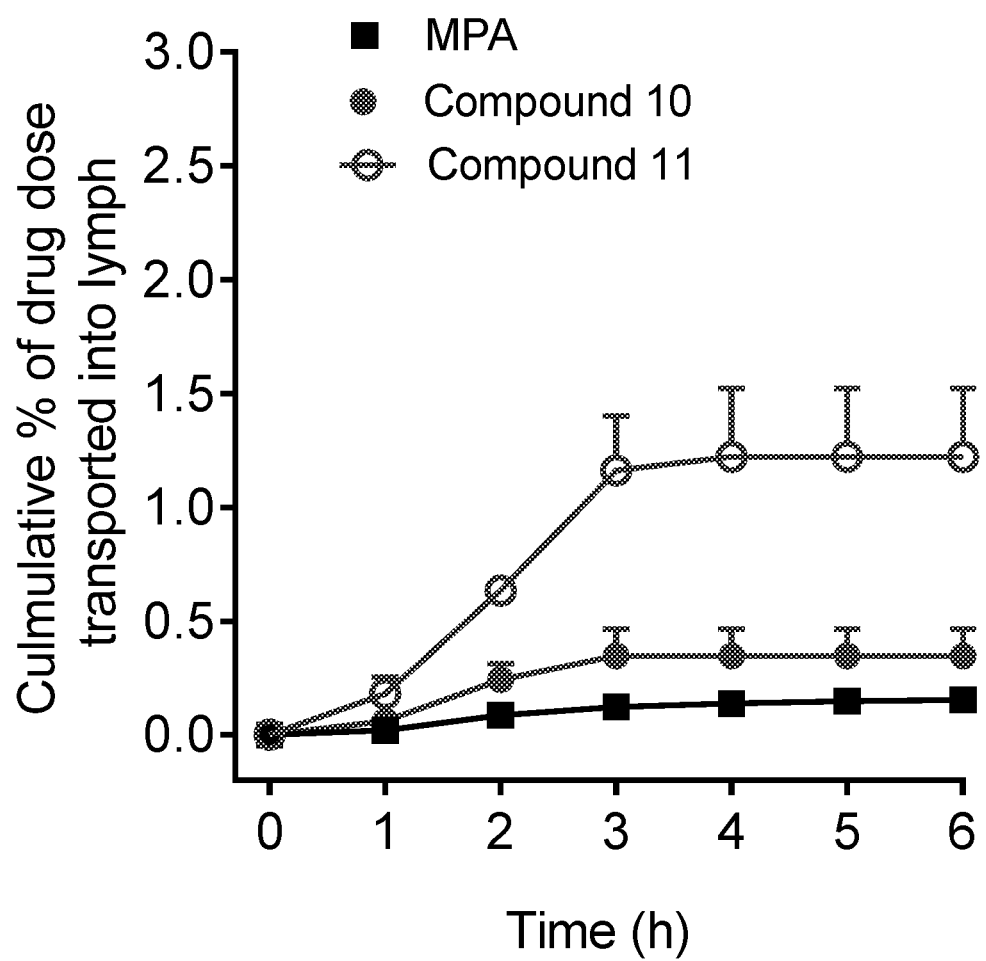
FIG. 8: Graphical representation of the cumulative lymphatic transport of total mycophenolic acid (MPA) related derivatives (% of administered dose) versus time in anaesthetised, mesenteric lymph duct cannulated male SD rats following intraduodenal infusion of MPA, Compound 10, and Compound 11.

As shown in FIG. 8 and Table 7, the lymphatic transport of Compound 10, having a acetal self-immolative (ASI) group and Compound 11 having a methylacetal self-immolative (MASI) group, was 0.35% and 1.22% (of administered dose). In contrast, the lymphatic transport of parent drug mycophenolic acid (MPA) was only 0.17% (of administered dose) following administration of the parent drug MPA.

TABLE 7

Lymphatic transport of total compound (% of administered dose) following intraduodenal infusion to anaesthetised, mesenteric lymph-duct cannulated rats (data are presented as mean ± SEM when n ≥ 3 or mean ± range when n = 2).

| Compound | Transport of total TST derivatives in lymph (% of dose) | Fold increase (compared with control group dosed with parent drug) |
|---|---|---|
| MPA (n = 5) | 0.17 ± 0.05 | 1.0 |
| 10 (n = 3) | 0.35 ± 0.12 | 2.1 |
| 11 (n = 3) | 1.22 ± 0.30 | 7.3 |

Example 10. Pharmacokinetic (PK) Studies in Rats

In order to assess the oral bioavailability of the compounds of the invention, pharmacokinetic studies were conducted using the following procedure. The day before drug administration, female (for testosterone related studies) or male (for SER and BUP related studies) Sprague-Dawley rats (220-320 g) were anaesthetised and the carotid artery was cannulated. The rats were then allowed to regain consciousness and fasted overnight prior to the commencement of experiments with free access to water. The next morning, formulations containing parent compounds or prodrugs were administered via oral gavage and blood samples were collected from the carotid artery cannula from −5 min up to 24 h post dosing and centrifuged at 5000 rpm for 5 min to separate plasma. During the blood sample collection period the rats had free access to water but remained fasted for a further 8 h following drug administration. Plasma samples were stored at −80° C. prior to assay by HPLC-MS-MS. In this case, samples were assayed for free drug (i.e. non-glyceride associated drug) and were not hydrolysed prior to assay (as was the case with the lymph samples). This data therefore reflects drug that is transported into the lymph and then liberated from the re-esterified drug-glyceride complex in the systemic circulation.

As previously described triglyceride prodrugs employing a short linker between the pharmaceutical agent testosterone and the glyceride unit (e.g., succinic acid, Compound 21) are limited by poor drug release in the systemic circulation (see Scriba, G. K. E., Arch. Pharm. (Weinheim). 1995, 328, (3), 271-276; and Scriba, G. K. E. et al., J. Pharm. Pharmacol.

Figure 2:
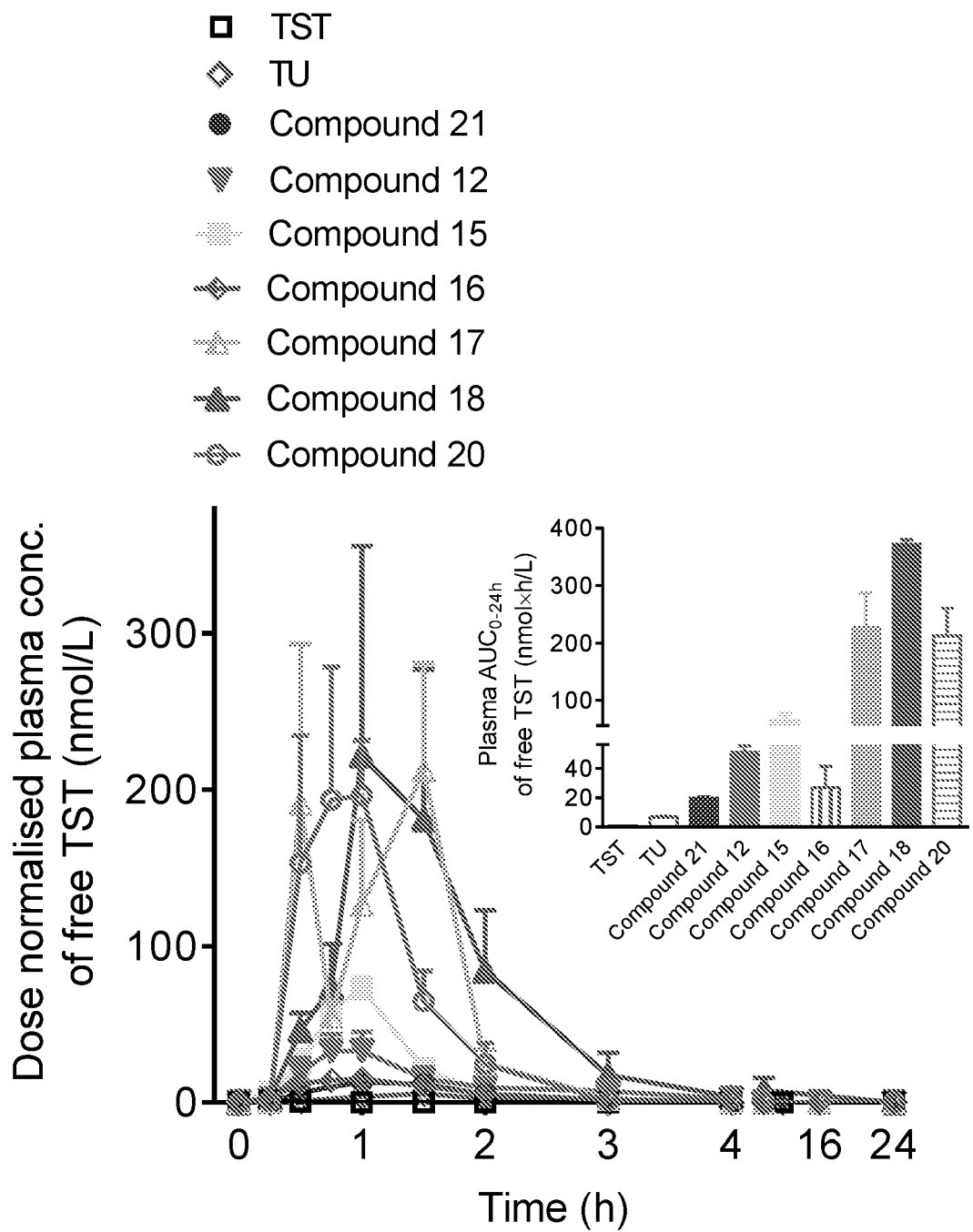
FIG. 2: Graphical representation of the dose-normalised testosterone plasma concentrations following oral gavage of testosterone, testosterone undecanoate (TU), Compound 12, Compound 15, Compound 16, Compound 17, Compound 18, Compound 20 and Compound 21 to conscious, carotid artery cannulated female SD rats.
Figure 3:
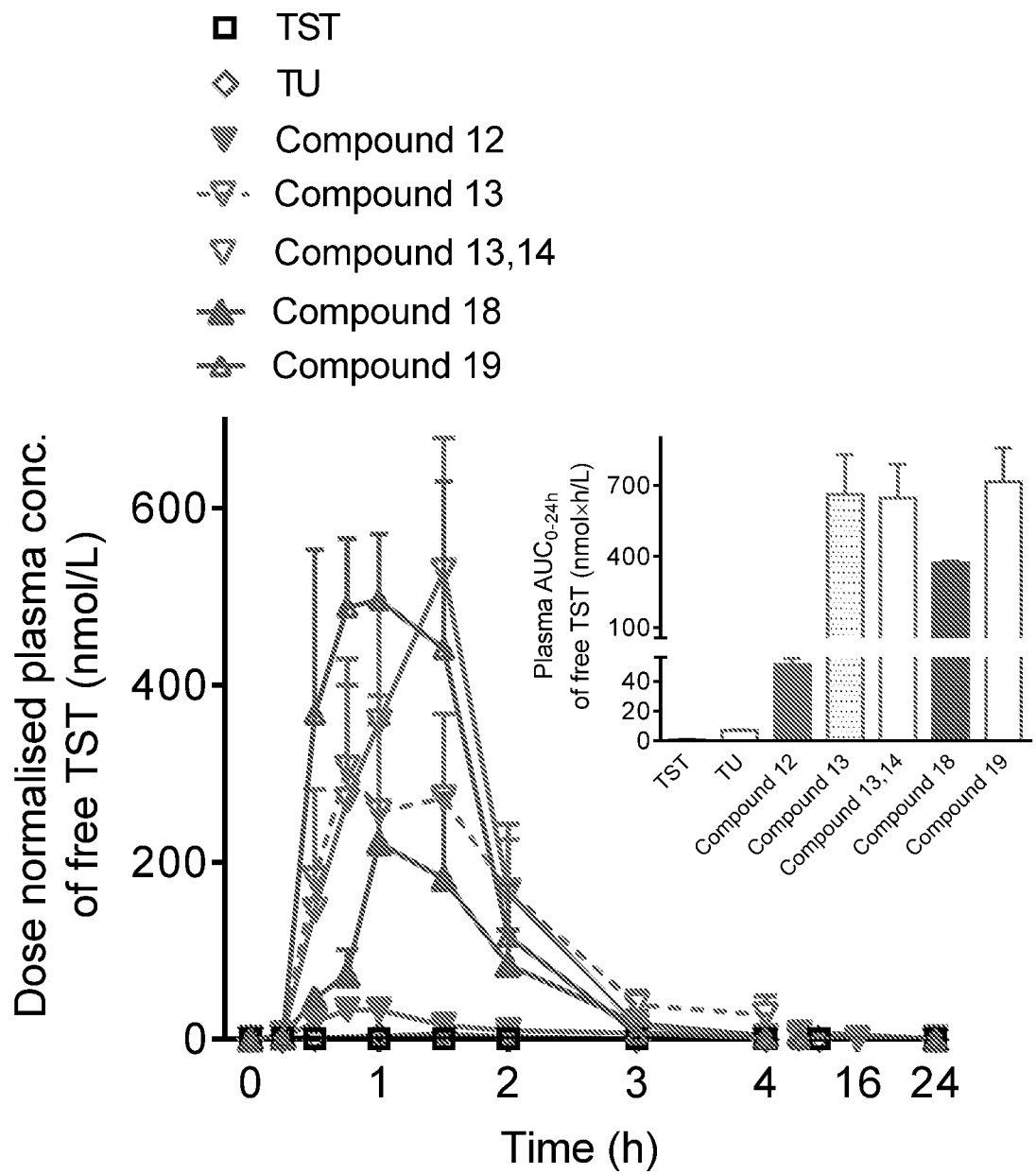
FIG. 3: Graphical representation of the dose-normalised testosterone plasma concentrations following oral gavage of testosterone, testosterone undecanoate (TU), Compound 12, Compound 13, Compounds 13/14, Compound 18 and Compound 19 to conscious, carotid artery cannulated female SD rats.

1995, 47, (11), 945-948)). As shown in FIG. 2 and Table 8 below, addition of a self-immolative group to the linker increases the systemic exposure of pharmaceutical agent, thereby avoiding first pass metabolism of the agent and increasing its oral bioavailability, even when combined with the previously dismissed succinic acid linker.

FIG. 2 illustrates dose-normalized testosterone plasma concentrations following oral gavage of testosterone formulations to conscious, carotid artery cannulated female SD rats. Formulations contained 1 mg of TU or TST, or approximately 2 mg of compounds of the invention containing testosterone dispersed in 40 mg oleic acid, 25 mg Tween 80 and 2 ml PBS. Doses are normalized to a 2 mg/kg equivalent dose of testosterone. Data are shown as mean±SEM. The embedded figure is the plot of the dose-normalized plasma $AUC_{0-24\,h}$ (nmol×h/L) of testosterone in the form of a bar graph.

Table 8 shows the pharmacokinetic parameters of the parent testosterone following oral administration of Compounds 12 to 20 or 21. In all cases where there are no methyl group inclusion in the short chain linker (Compounds 12, 15-18 or 20), the systemic exposure of testosterone was greater than that for Compound 21 (~1.4-18 fold increase) or the commercial product TU (~4-54 fold increase). Although the lymphatic transport of Compound 12 and Compound 17 was relatively low (FIG. 1 and Table 4), the systemic exposure of parent testosterone was still much higher following oral administration of both prodrugs. This suggests that the self immolative group facilitates conversion of the prodrug to the parent drug in the systemic circulation.

TABLE 8

Pharmacokinetic parameters after oral administration of the compound to conscious carotid artery cannulated SD female rats (doses are normalized to a 2 mg/kg equivalent testosterone dose and data are presented as mean ± SEM).

| Compound | Cmax (nmol/L) | Tmax (h) | $AUC_{0-24\,h}$ (nmol × h/L) | $AUC_{0-24\,h}$ fold increase compared with TU group |
|---|---|---|---|---|
| Testosterone (n = 3) | 1.1 ± 0.3 | 0.25 ± 0.0 | 0.5 ± 0.2 | 0.076 |
| TU (n = 4) | 5.6 ± 0.5 | 1.5 ± 0.0 | 6.8 ± 0.4 | 1.0 |
| 21 (n = 4) | 13.7 ± 0.7 | 1.1 ± 0.1 | 19.6 ± 0.8 | 2.9 |
| 12 (n = 4) | 39.1 ± 11.0 | 1.1 ± 0.3 | 51.1 ± 4.1 | 7.5 |
| 13/14 (n = 4) | 568.5 ± 154.9 | 1.4 ± 0.1 | 645.3 ± 144.9 | 94.6 |
| 13 (n = 4) | 414.4 ± 89.3 | 1.2 ± 0.2 | 661.6 ± 169.2 | 97 |
| 15 (n = 3) | 73.1 ± 4.2 | 1.0 ± 0.0 | 65.5 ± 6.8 | 9.6 |
| 16 (n = 3) | 16.6 ± 1.0 | 0.8 ± 0.1 | 26.9 ± 8.4 | 3.9 |
| 17 (n = 4) | 213.3 ± 70.8 | 1.1 ± 0.3 | 226.8 ± 60.2 | 33.2 |
| 18 (n = 4) | 333.5 ± 342.6 | 1.1 ± 0.2 | 371.9 ± 8.1 | 54.5 |
| 19 (n = 3) | 694.9 ± 26.6 | 1.0 ± 0.3 | 716.1 ± 86.4 | 105 |
| 20 (n = 4) | 271.9 ± 65.1 | 0.8 ± 0.1 | 212.3 ± 48.5 | 31.1 |

The utility of the prodrugs can be further enhanced by increasing the lymphatic transport of the prodrugs. Inclusion of a methyl group on the carbon alpha or beta to the esters at either end of the short chain linker is able to increase the stability of the monoglyceride intermediates of the prodrugs, thus enabling increased lymphatic transport. The in vitro digestion and lymphatic transport results of Compound 12 versus Compounds 13/14 (see FIG. 9, FIG. 1 and Table 4) support the suggestion and show significantly enhanced stability for Compounds 13/14 under simulated intestinal conditions. Consistent with the increase in lymphatic transport of Compounds 13/14 and the potential for the self-immolative group to promote systemic release of testosterone from the prodrug, systemic exposure of testosterone after administration of Compounds 13/14 or Compound 13 alone is ~13 fold higher than Compound 12, and 95-97 fold higher than TU (Table 8). In addition, inclusion of a methyl group to the short chain linker in the case of the FSI prodrug also enhanced the bioavailability of testosterone. Thus the systemic exposure of testosterone after administration of Compound 19 is 1.9 fold higher than Compound 18 and 105 fold higher than TU (Table 8).

Figure 5:
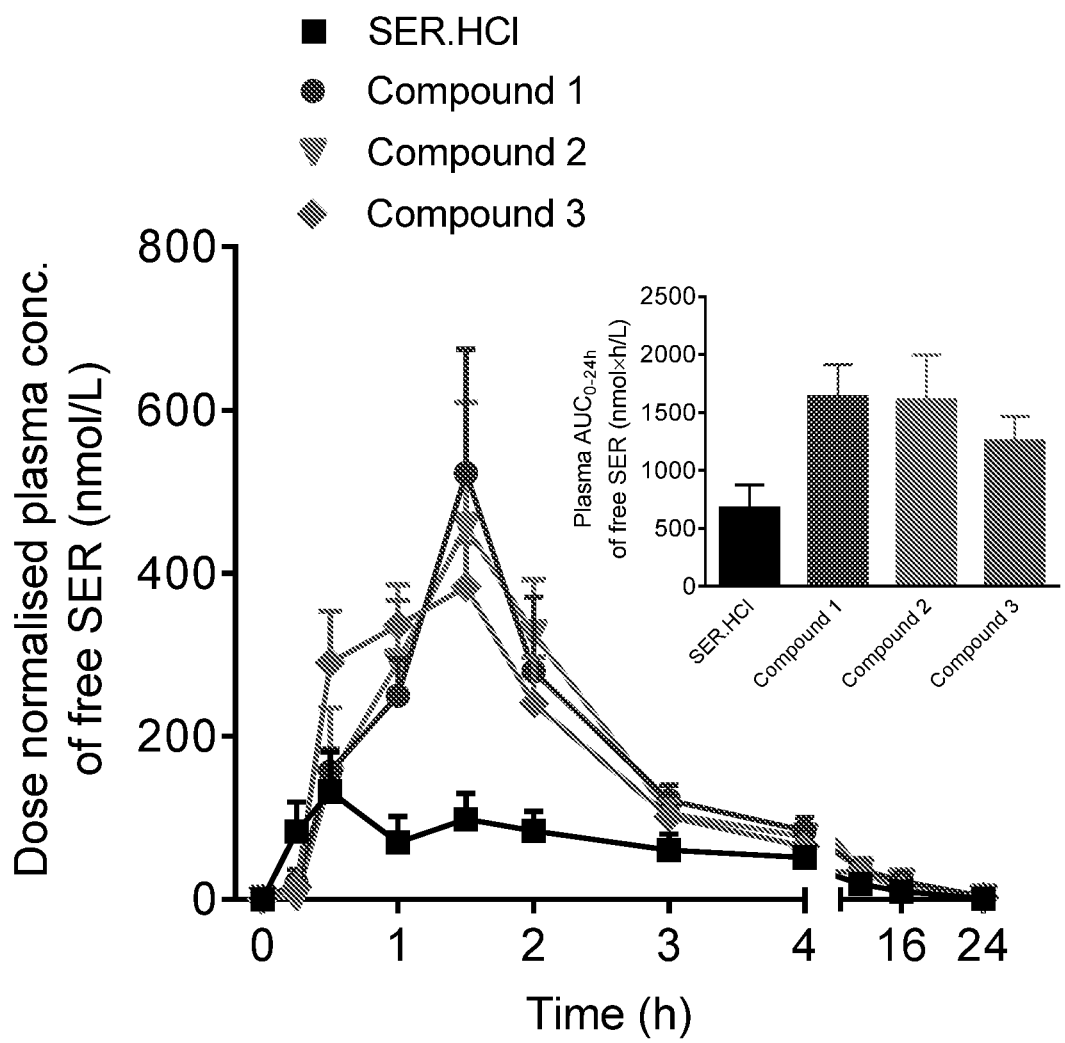
FIG. 5: Graphical representation of the dose-normalised sertraline (SER) plasma concentrations following oral gavage of SER hydrochloride (SER·HCl), Compound 1, Compound 2, and Compound 3.

FIG. 5 illustrates dose-normalized SER plasma concentrations following oral gavage of formulations to conscious, carotid artery cannulated male SD rats. In the SER parent drug control group, the formulation contained 0.7 mg of SER·HCl dissolved in 2 ml water. Prodrug formulations contained 2 mg of compounds of the invention containing SER dispersed in 40 mg oleic acid, 25 mg Tween 80 and 2 ml PBS. Doses are normalized to a 2 mg/kg equivalent dose of SER. Data are shown as mean±SEM. The embedded figure is the plot of the dose-normalized plasma $AUC_{0-24\,h}$ (nmol×h/L) of SER in the form of a bar graph.

The pharmacokinetic parameters of SER following administration of SER·HCl, Compound 1, 2 and 3 are shown in Table 9. In all cases systemic exposure of SER after administration of the prodrugs was greater than that for SER·HCl (2-3 folder increase). This suggests that the prodrugs are transported lymphatically (as exemplified by Compound 3 in FIG. 4 and Table 5) and the self immolative group facilitates conversion of the prodrug to the parent drug in the systemic circulation.

TABLE 9

Pharmacokinetic parameters after oral administration of SER related compounds to conscious carotid artery cannulated SD male rats (doses are normalized to a 2 mg/kg equivalent SER dose and data are presented as mean ± SEM).

| Compound | Cmax (nmol/L) | Tmax (h) | $AUC_{0-24\,h}$ (nmol × h/L) | $AUC_{0-24\,h}$ fold increase compared with SER · HCl group |
|---|---|---|---|---|
| SER · HCl (n = 3) | 132.6 ± 48.1 | 0.5 ± 0.0 | 678.2 ± 194.5 | 1.0 |
| 1 (n = 3) | 929.4 ± 439.2 | 1.0 ± 0.0 | 2021.2 ± 420.6 | 3.0 |
| 2 (n = 3) | 797.9 ± 198.6 | 1.67 ± 0.17 | 2068.2 ± 212.8 | 3.0 |
| 3 (n = 3) | 594.1 ± 86.5 | 1.33 ± 0.17 | 1436.9 ± 144.6 | 2.1 |

Figure 7:
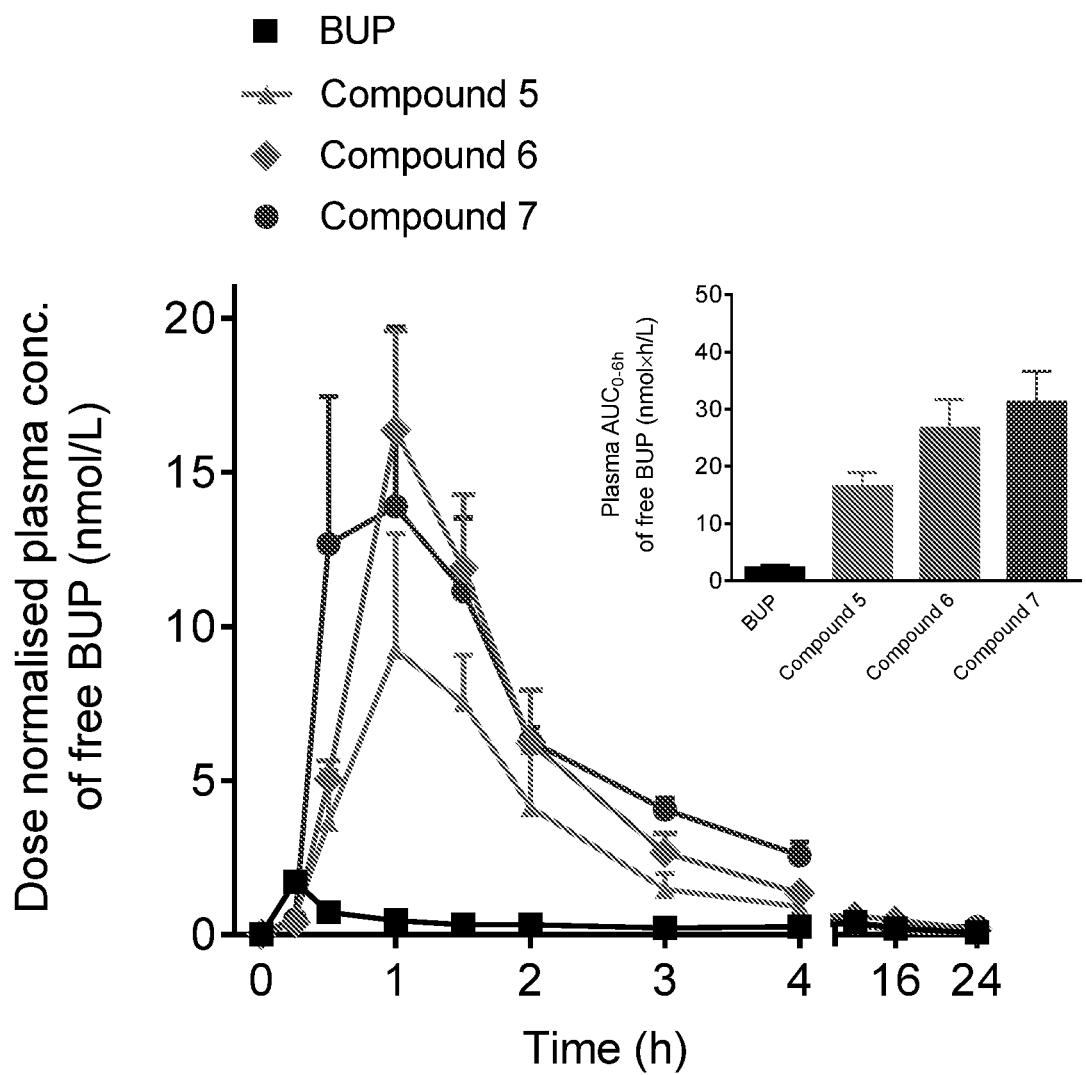
FIG. 7: Graphical representation of the dose-normalised buprenorphine (BUP) plasma concentrations following oral gavage of BUP, Compound 5, Compound 6, and Compound 7.

FIG. 7 illustrates dose-normalized BUP plasma concentrations following oral gavage of formulations to conscious, carotid artery cannulated male SD rats. In the BUP parent drug control group, the formulation contained 0.02 mg of BUP dissolved in 2 ml of 0.1% acetic acid aqueous solution. Prodrug formulations contained 0.05 mg of compounds of the invention containing BUP dispersed in 40 mg oleic acid, 25 mg Tween 80 and 2 ml PBS. Doses are normalized to a 0.06 mg/kg equivalent dose of BUP. Data are shown as mean±SEM. The embedded figure is the plot of the dose-normalized plasma $AUC_{0-6\,h}$ (nmol×h/L) of BUP in the form of a bar graph.

The pharmacokinetic parameters of BUP following administration of BUP, Compound 5, 6, and 7 are shown in Table 10. In all cases systemic exposure of BUP after administration of compounds of the invention was greater than that for BUP (7-14 folder increase). This suggests that the prodrugs are transported lymphatically (as exemplified by Compound 6 and 7 in FIG. 6 and Table 6) and the self immolative group facilitates conversion of the prodrug to the parent drug in the systemic circulation.

TABLE 10

Pharmacokinetic parameters after oral administration of BUP related compounds to conscious carotid artery cannulated SD male rats (doses are normalized to a 0.06 mg/kg equivalent BUP dose and data are presented as mean ± SEM).

| Compound | Cmax (nmol/L) | Tmax (h) | $AUC_{0\text{-}6\,h}$* (nmol × h/L) | Fold increase compared with BUP group |
|---|---|---|---|---|
| BUP (n = 4) | 1.73 ± 0.23 | 0.3 ± 0.0 | 2.27 ± 0.44 | 1.0 |
| 5 (n = 3) | 9.80 ± 1.95 | 1.2 ± 0.2 | 16.4 ± 2.5 | 7.3 |
| 6 (n = 3) | 16.4 ± 3.2 | 1.0 ± 0.0 | 26.7 ± 5.0 | 11.8 |
| 7 (n = 6) | 17.3 ± 5.2 | 1.3 ± 0.2 | 31.2 ± 5.4 | 13.8 |

*Truncated AUCs ($AUC_{0\text{-}6\,h}$) rather than $AUC_{0\text{-}24\,h}$ were used due to the presence of a second peak in the BUP plasma concentration versus time profile following administration of the parent drug. The second peak most likely reflects enterohepatic recycling of BUP.

Example 11. In Vitro Hydrolysis of Compounds by Porcine Pancreatin Lipase

In vitro hydrolysis of testosterone prodrugs was performed via incubation with porcine pancreatic lipase. Briefly, pancreatic lipase solution was prepared prior to the hydrolysis experiment by dispersion of 1 g porcine pancreatin in 5 ml of lipolysis buffer. The suspension was mixed well and centrifuged at 3500 rpm for 15 minutes at 5° C. to provide a supernatant. An amount of 1000 ml of lipolysis buffer was prepared with 0.474 g of tris-maleate (2 mM), 0.206 g of $CaCl_2 \cdot H_2O$ (1.4 mM) and 8.775 g of NaCl (150 mM) adjusted with NaOH to pH 6.5. To assess the potential for prodrug hydrolysis in the intestine, 20 μl of prodrug solution (1 mg/ml dissolved in acetonitrile), 900 μl of simulated intestinal micellar solution [prepared with 0.783 g of NaTDC (3 mM) and 0.291 g of phosphatidyl choline (0.75 mM) in 500 ml lipolysis buffer] and 100 μl of enzyme solution were incubated at 37° C. 20 μl samples of the incubation solution were taken at 0, 5, 10, 15, 30, 60, 90, 120 and 180 minutes post incubation and added to 180 μl of ACN to stop lipolysis. The mixture was vortexed and centrifuged at 5000 rpm for 5 minutes to precipitate proteins prior to analysis. The supernatant was analysed by HPLC-MS for residual compound concentrations, and the potential products of compound hydrolysis were analysed.

On incubation with digestive enzymes, the monoglycerides forms of the prodrugs are formed very rapidly. The stability in simulated intestinal conditions is therefore better assessed by the stability of the monoglycerides form that is generated by the initial digestion process. The monoglycerides form must remain intact to be absorbed and re-esterified in the enterocyte prior to entry into the lymphatics. Stability profiles of the monoglyceride forms of Compound 12, Compounds 15-17 and Compound 20 (n=2-3 for each group) during in vitro incubation with freshly prepared porcine pancreatic lipase are compared with that of non-self immolative containing Compound 21 (n=3) in FIG. 9. The data show that inclusion of the acetal (ASI), flipped ester (FSI), carboxy(methylacetal) (CMSI) or p-hydroxybenzyl carbonyl (PHB) self-immolative group results in significantly decreased luminal stability of MG forms of the prodrugs. However, the tri-methyl lock self immolative group appears to have no effect on the luminal stability as the monoglyceride form of Compound 15 is similarly stable to that of Compound 21.

Figure 9:
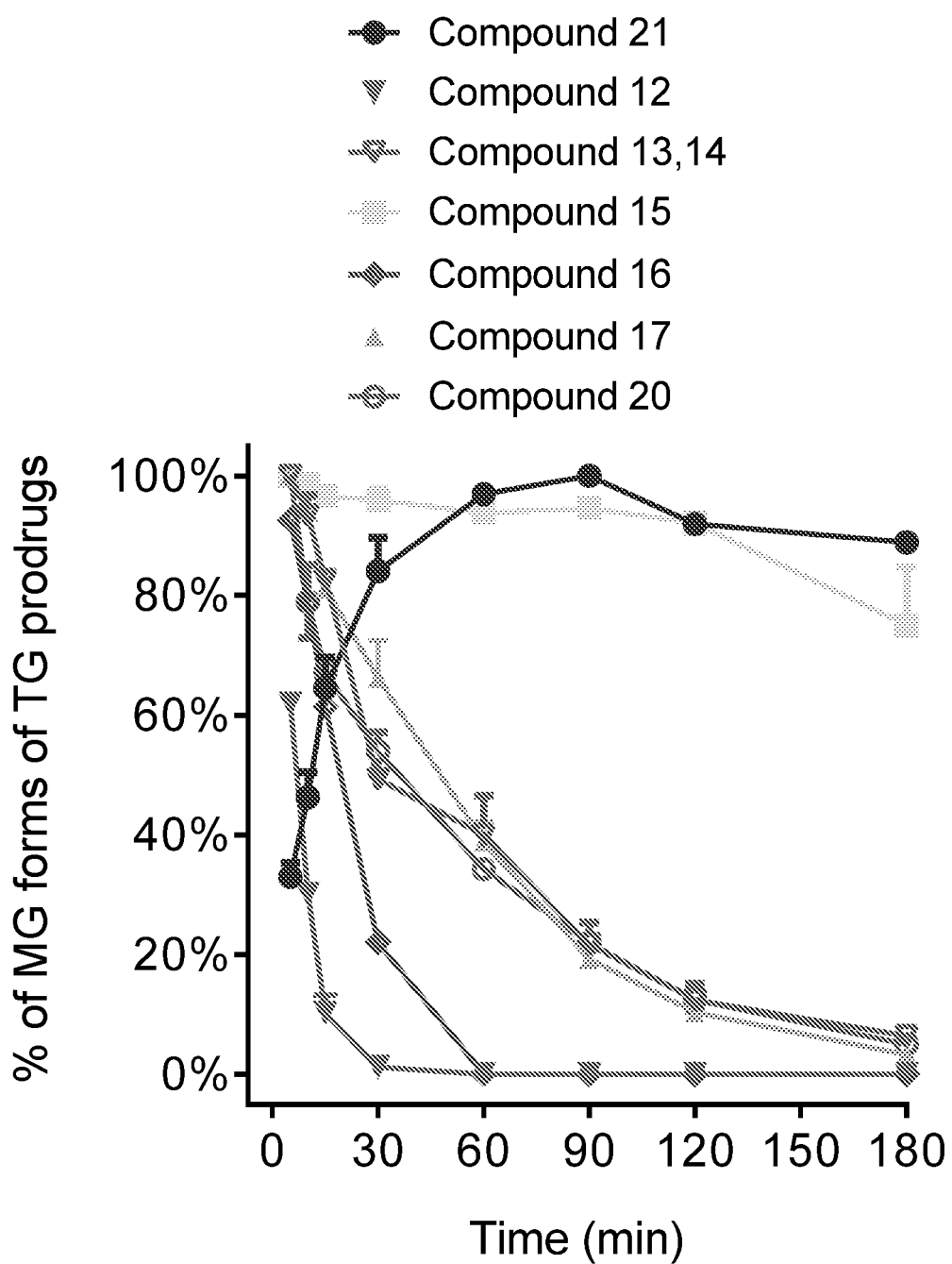
FIG. 9: Graphical representation of the stability profiles of the monoglyceride forms of Compound 12, Compound 13/14, Compound 15, Compound 16, Compound 17, Compound 20 and Compound 21 during in vitro incubation with porcine pancreatic lipase.

FIG. 9 also provides evidence of the ability of methyl substitution to improve the luminal stability of testosterone prodrug containing an acetal self immolative linker (where the acetal group usually reduces luminal stability). As shown in the figure, the monoglyceride form of Compound 12 was labile in the in vitro lipolysis assay. In contrast, the mixture of alpha and beta methyl substituted Compounds 13/14 were much more stable. The enhanced stability of the methyl substituted ASI prodrug is most likely responsible for the significant increases in in vivo lymphatic transport as well as increases in testosterone exposure testosterone in the systemic circulation after oral administration.

Example 12. In Vitro Release of MPA from Prodrugs in Lymph Supplemented with Lipoprotein Lipase In order to probe the release of free MPA from TG prodrugs in the lymphatics (the active site of MPA is in lymphocytes that are enriched in the lymphatic system), MPA prodrugs were incubated with rat lymph supplemented with lipoprotein lipase (LPL, 200 unit/ml). LPL is a key enzyme required for the hydrolysis of lipoprotein associated TG in normal physiological conditions and is therefore expected to be a key contributor to lipolysis of the re-esterified Drug-TG construct in plasma, largely via liberation of FAs in the sn-1 and the sn-3 position of the TG-mimetic, prior to drug release from the 2' positon via esterase hydrolysis. LPL is tethered to lymphocytes or lymphatic/vascular endothelial cells under physiological conditions. In the current in vitro studies, rat lymph was therefore supplemented with LPL to better reflect the in vivo situation. To start hydrolysis, 10 μl of LPL solution (10,000 unit/ml) was added to a mixture of 10 μl of prodrug solution (1 mg/ml dissolved in acetonitrile) and 500 μl of blank Sprague Dawley rat lymph. The solution was incubated at 37° C. Samples (20 μl) of the incubation solution were taken at 0, 5, 10, 15, 30, 60, 90, 120 and 180 minutes post incubation and added to 980 μl of 9:1 (v/v) ACN-water to stop lipolysis. The mixture was vortexed and centrifuged at 4500 g for 5 minutes to precipitate proteins prior to analysis. The supernatant was analysed by HPLC-MS/MS for MPA concentrations.

Figure 10:
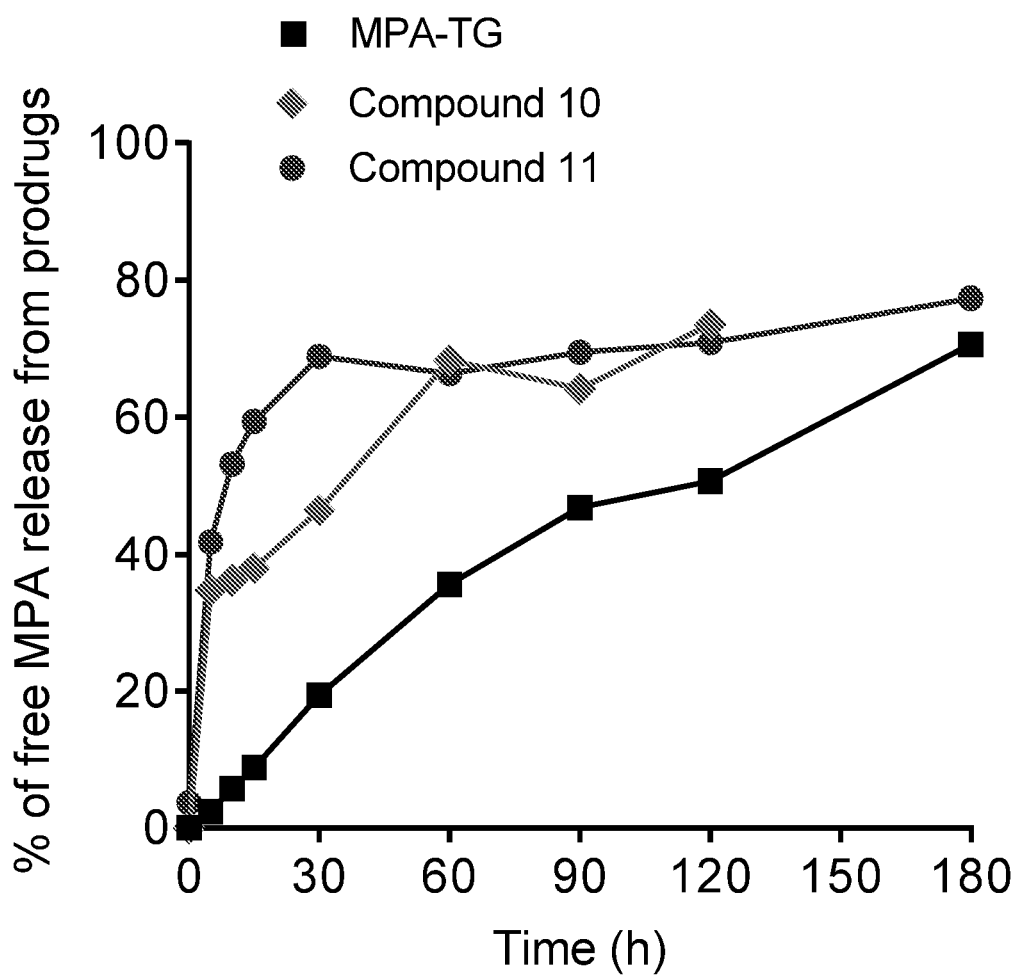
FIG. 10: Graphical representation of the release of MPA from 1,3-dipalmitoylglycerol mycophenolate (MPA-TG), Compound 10 and Compound 11.

As shown in FIG. 10 (n=1 for each prodrug), on incubation with LPL supplemented rat lymph, the release of the pharmacologically active MPA from Compound 10 and Compound 11 were very rapid. The rate of parent MPA release from these two SI group-containing prodrugs was much higher than that from MPA-TG, a prodrug without SI group. The data show that inclusion of the acetal (ASI) or methylacetal (MASI) self-immolative group results in significantly enhanced release of the parent compounds and thus provides opportunities for targeted delivery of therapeutic agents to active sites in the lymphatic system.

We claim:

1. A compound of the formula (I):

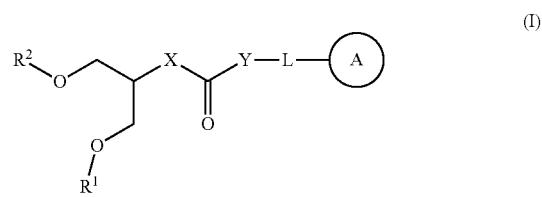

wherein

R[1] and R[2] independently represent H, or a residue of a $C_2$-$C_{28}$ fatty acid;

—X— is selected from —O—, —NH— and —S—;

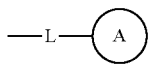

represents a pharmaceutical agent;

-L- is —X'—;

—Y— represents an optionally substituted —$C_1$-$C_2$alkylC(O)$R^3$— group or a —$C_2$alkenylC(O)$R^3$— or —$C_2$alkynylC(O)$R^3$— group;

$R^3$ is a self-immolative group;

X' is O, S, N($R^4$) or N(H)S(O)$_2$; and $R^4$ is H or $C_1$-$C_4$alkyl; or, pharmaceutically acceptable salts thereof.

2. A compound according to claim 1, wherein $R^3$ is selected from:

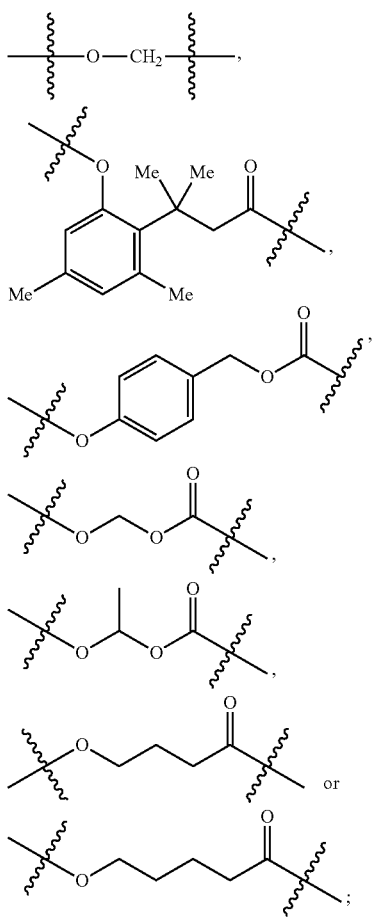

wherein ～ denotes the point of attachment with the residue of a pharmaceutical agent and with the —Y— group.

3. A compound according to claim 1, wherein the pharmaceutical agent is one that exhibits greater than 50% first pass metabolism.

4. A compound according to claim 1, wherein the pharmaceutical agent is selected from testosterone, mycophenolic acid, estrogen, morphine, raloxifene, alphaxolone, atorvastatin, buprenorphine, pentazocine, propranolol, L-DOPA, midazolam, lidocaine, chlorpromazine, amitriptyline, nortriptyline, isosorbidedinitrate, oxprenolol, labetalol, verapamil, salbutamol, epitiostanol, melphalan or lovastatin.

5. A compound according to claim 1, wherein the pharmaceutical agent is testosterone and the compound is represented by the formula (V):

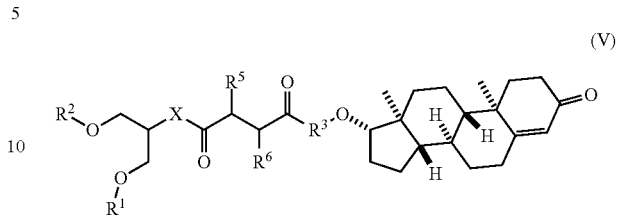

wherein $R^1$, $R^2$, $R^3$, and X are as defined in claim 1, and $R^5$ and $R^6$ are individually selected from hydrogen and $C_1$-$C_4$alkyl; or pharmaceutically acceptable salts thereof.

6. A compound according to claim 5, wherein $R^5$ is methyl and $R^6$ is hydrogen.

7. A compound according to claim 5, wherein $R^5$ is hydrogen and $R^6$ is methyl.

8. A compound according to claim 5, wherein X is oxygen.

9. A compound according to claim 5, wherein $R^1$ and $R^2$ are residues of palmitic acid.

10. A compound according to claim 1, wherein X is oxygen.

11. A compound according to claim 1, wherein $R^1$ and $R^2$ are residues of palmitic acid.

12. A compound according to claim 1, wherein the pharmaceutical agent is selected from non-steroidal anti-inflammatory medications (NSAIDS), COX-2 inhibitors, corticosteroid anti-inflammatory medications, anti-malarial medications, cyclophosphamide, nitrosoureas, platinum, methotrexate, azathioprine, mercaptopurine, fluorouracil, dactinomycin, anthracyclines, mitomycin C, bleomycin, mithramycin, drugs acting on immunophilins, sulfasalazine, leflunomide, mycophenolate, opioids, fingolimod, myriocin, chlorambucil, doxorubicin, nelarabine, cortisone, dexamethasone, prednisone, pralatrexate, vinblastine, bortezomib, thiotepa, nelarabine, daunorubicin hydrochloride, clofarabine, cytarabine, dasatinib, imatinib mesylate, ponatinib hydrochloride, vincristine sulfate, bendamustine hydrochloride, fludarabine phosphate, bosutinib, nilotinib, omacetaxine mepesuccinate, anastrozole, capecitabine, letrozole, paclitaxel, gemcitabine, fulvestrant, tamoxifen, lapatinib, toremifene, ixabepilone, eribulin, albendazole, ivermectin, diethylcarbamazine, albendazole, doxycycline, closantel, maraviroc, enfuvirtide, deoxythymidine, zidovudine, stavudine, didanosine, zalcitabine, abacavir, lamivudine, emtricitabine, tenofovir, nevirapine, delavirdine, efavirenz, rilpivirine, raltegravir, elvitegravir, lopinavir, indinavir, nelfinavir, amprenavir, ritonavir, acyclovir, immunosuppressants and pharmaceutically active peptides.

13. A compound according to claim 1, wherein $R^1$ and $R^2$ independently represent a residue of a $C_2$-$C_{28}$ fatty acid.

14. A compound according to claim 1, wherein —Y— represents an optionally substituted —$C_1$-$C_2$alkylC(O)$R^3$—.

15. A compound according to claim 1, wherein —Y— represents a —$C_1$-$C_2$alkylC(O)$R^3$— group optionally substituted with methyl.

16. A compound according to claim 1, wherein:

R$^1$ and R$^2$ independently represent a residue of a C$_2$-C$_{28}$ fatty acid;

—X— is —O—; and

—Y— represents an optionally substituted —C$_1$-C$_2$alkylC(O)R$^3$— group.

17. A compound according to claim 16, wherein R$^3$ is selected from:

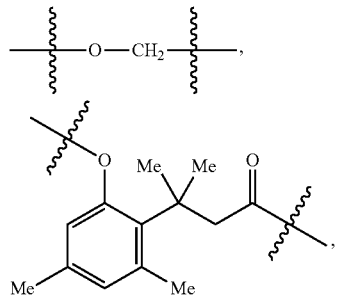

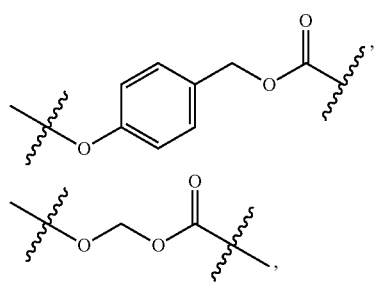

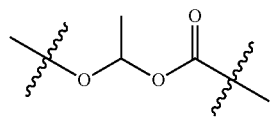

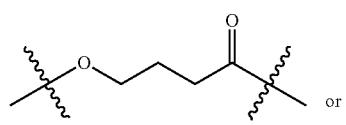

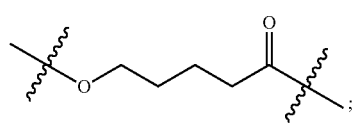

wherein $\sim\!\sim$ denotes the point of attachment with the residue of a pharmaceutical agent and with the —Y— group.

18. A compound according to claim 16, wherein the pharmaceutical agent is selected from testosterone, mycophenolic acid, cyclosporine, tacrolimus, sirolimus, celecoxib, rofecoxib, estrogen, morphine, tetrahydrocannabinol, cannabidiol, metoprolol, raloxifene, alphaxolone, atorvastatin, buprenorphine, pentazocine, propranolol, L-DOPA, lidocaine, chlorpromazine, amitriptyline, nortriptyline, oxprenolol, labetalol, salbutamol, epitiostanol, melphalan or lovastatin.

19. A compound according to claim 1, represented by the formula (II):

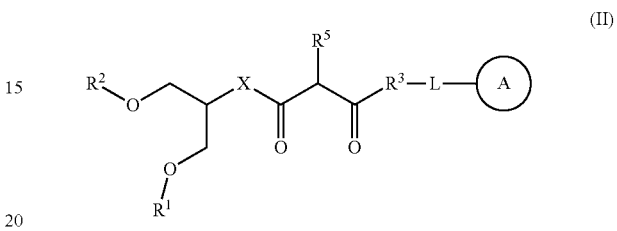

wherein

R$^1$, R$^2$, R$^3$, R$^4$, X, X', and

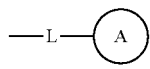

are as defined in claim 1; and

R$^5$ is selected from hydrogen and C$_1$-C$_4$alkyl; or pharmaceutically acceptable salts thereof.

20. A compound according to claim 1, represented by the formula (III):

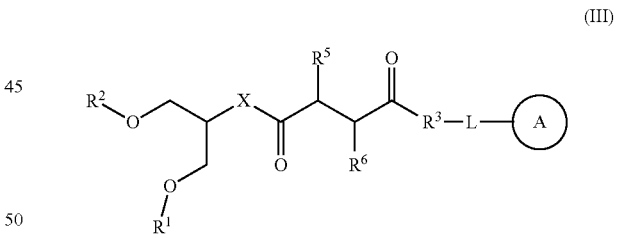

wherein R$^1$, R$^2$, R$^3$, R$^4$, X, X', and

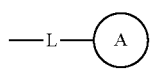

are as defined in claim 1; and

R$^5$ and R$^6$ are individually selected from hydrogen and C$_1$-C$_4$alkyl; or pharmaceutically acceptable salts thereof.

21. A compound according to claim 1, wherein the compound is selected from those compounds listed in Table 1A and Table 3A:

TABLE 1A

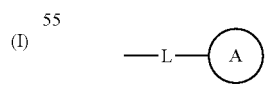

| Compound No. | R¹ & R² | X | R⁵ | R⁶ | R³ | L | A |
|---|---|---|---|---|---|---|---|
| 1 | $C(O)C_{15}H_{31}$ | O | H | H | CASI[1] | NMethyl | Sertraline |
| 2 | $C(O)C_{15}H_{31}$ | O | H | H | CMSI[2] | NMethyl | Sertraline |
| 3 | $C(O)C_{15}H_{31}$ | O | H | H | TML[3] | NMethyl | Sertraline |
| 4 | $C(O)C_{15}H_{31}$ | O | H | H | CASI | O | Buprenorphine |
| 5 | $C(O)C_{15}H_{31}$ | O | H | H | CMSI | O | Buprenorphine |
| 6 | $C(O)C_{15}H_{31}$ | O | H | H | TML | O | Buprenorphine |
| 7 | $C(O)C_{15}H_{31}$ | O | H | H | FSI-5[4] | O | Buprenorphine |
| 8 | $C(O)C_{15}H_{31}$ | O | Methyl | H | FSI-5 | O | Buprenorphine |
| 9 | $C(O)C_{15}H_{31}$ | O | H | H | FSI-5 | O | Metoprolol |

[1] CASI = a carboxyacetal self-immolative group;
[2] CMSI = a carboxy(methylacetal) self-immolative group;
[3] TML = a trimethyl lock self-immolative group;
[4] FSI-5 = a flipped ester self-immolative group liberating pharmaceutical agent A via loss of a 5-carbon lactone;

TABLE 3A

| Compound No. | R¹ | R² | X | R⁵ | R⁶ | R³ |
|---|---|---|---|---|---|---|
| 12 | $C(O)C_{15}H_{31}$ | $C(O)C_{15}H_{31}$ | O | H | H | ASI[1] |
| 13 | $C(O)C_{15}H_{31}$ | $C(O)C_{15}H_{31}$ | O | Methyl | H | ASI |
| 14 | $C(O)C_{15}H_{31}$ | $C(O)C_{15}H_{31}$ | O | H | Methyl | ASI |
| 15 | $C(O)C_{15}H_{31}$ | $C(O)C_{15}H_{31}$ | O | H | H | TML[2] |
| 16 | $C(O)C_{15}H_{31}$ | $C(O)C_{15}H_{31}$ | O | H | H | PHB[3] |
| 17 | $C(O)C_{15}H_{31}$ | $C(O)C_{15}H_{31}$ | O | H | H | FSI-4[4] |
| 18 | $C(O)C_{15}H_{31}$ | $C(O)C_{15}H_{31}$ | O | H | H | FSI-5[5] |
| 19 | $C(O)C_{15}H_{31}$ | $C(O)C_{15}H_{31}$ | O | Methyl | H | FSI-5 |
| 20 | $C(O)C_{15}H_{31}$ | $C(O)C_{15}H_{31}$ | O | H | H | CMSI[6] |

[1] ASI = an acetal self-immolative group;
[2] TML = a trimethyl lock self-immolative group;
[3] PHB = a p-hydroxybenzylcarbonyl self-immolative group;
[4] FSI-4 = a flipped ester self-immolative group liberating testosterone via loss of a 4-carbon lactone;
[5] FSI-5 = a flipped ester self-immolative group liberating testosterone via loss of a 5-carbon lactone;
[6] CMSI = a carboxy(methylacetal) self-immolative group.

22. A compound of the formula (I):

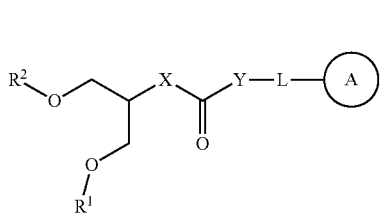

(I)

wherein $R^1$ and $R^2$ independently represent H, or a residue of a $C_2$-$C_{28}$ fatty acid;

—X— is —O—;

—L— represents a pharmaceutical agent;

-L- is —X'—;

—Y— represents an optionally substituted —$C_1$-$C_2$alkyl$C(O)R^3$— group or a —$C_2$alkenyl$C(O)R^3$— or —$C_2$alkynyl$C(O)R^3$— group;

$R^3$ is a self-immolative group; and

X' is O; or pharmaceutically acceptable salts thereof.

23. The compound according to claim 22 wherein $R^3$ is selected from:

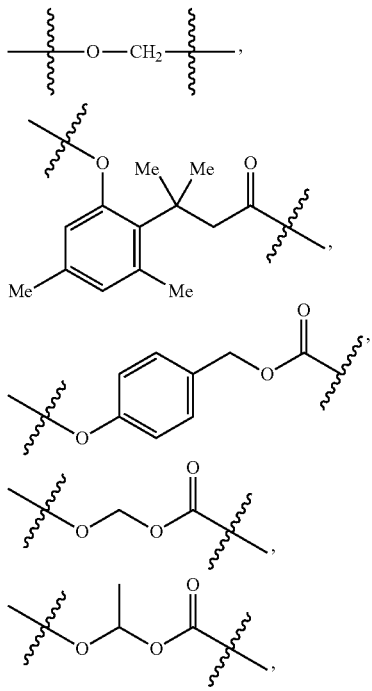

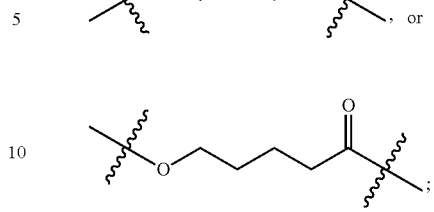

wherein ∼∼ denotes the point of attachment with the residue of a pharmaceutical agent and with the —Y— group.

24. A pharmaceutical composition comprising a therapeutically effective amount of a compound according to claim 1, or pharmaceutically acceptable salts thereof, together with at least one pharmaceutically acceptable carrier or diluent.

25. A pharmaceutical composition comprising a therapeutically effective amount of a compound according to claim 5, or pharmaceutically acceptable salts thereof, together with at least one pharmaceutically acceptable carrier or diluent.

26. A pharmaceutical composition comprising a therapeutically effective amount of a compound according to claim 16, or pharmaceutically acceptable salts thereof, together with at least one pharmaceutically acceptable carrier or diluent.

* * * * *